US007541164B2

(12) United States Patent
Schilling et al.

(10) Patent No.: US 7,541,164 B2
(45) Date of Patent: *Jun. 2, 2009

(54) MAMMALIAN CELL CULTURE PROCESSES FOR PROTEIN PRODUCTION

(75) Inventors: Bernhard M. Schilling, Syracuse, NY (US); Linda Matlock, Parish, NY (US); Stephen G. Zegarelli, North Syracuse, NY (US); William V. Burnett, Fayetteville, NY (US); Christoph E. Joosten, Manlius, NY (US); Jonathan D. Basch, East Syracuse, NY (US); Sivakesava Sakhamuri, Syracuse, NY (US); Steven S. Lee, Manlius, NY (US)

(73) Assignee: Bristol-Myers Squibb Company, Princeton, NJ (US)

( * ) Notice: Subject to any disclaimer, the term of this patent is extended or adjusted under 35 U.S.C. 154(b) by 188 days.

This patent is subject to a terminal disclaimer.

(21) Appl. No.: 10/742,564

(22) Filed: Dec. 18, 2003

(65) Prior Publication Data
US 2005/0019859 A1    Jan. 27, 2005

Related U.S. Application Data

(60) Provisional application No. 60/436,101, filed on Dec. 23, 2002.

(51) Int. Cl.
*C12N 5/06* (2006.01)
*A61K 39/395* (2006.01)
*A61K 38/00* (2006.01)

(52) U.S. Cl. .................. 435/70.1; 435/41; 424/143.1; 424/185.1; 530/388.22; 530/387.3

(58) Field of Classification Search .............. 435/41, 435/70.1, 70.3, 395, 325; 530/395
See application file for complete search history.

(56) References Cited

U.S. PATENT DOCUMENTS

| | | | |
|---|---|---|---|
| 4,357,422 A | 11/1982 | Giard et al. |
| 4,994,387 A | 2/1991 | Levine et al. |
| 5,132,223 A | 7/1992 | Levine et al. |
| 5,318,898 A | 6/1994 | Israel |
| 5,348,877 A | 9/1994 | McKenna et al. |
| 5,434,131 A | 7/1995 | Linsley et al. |
| 5,521,288 A | 5/1996 | Brady et al. |
| 5,545,722 A | 8/1996 | Naka |
| 5,580,756 A | 12/1996 | Brady et al. |
| 5,637,481 A | 6/1997 | Ledbetter et al. |
| 5,705,364 A | 1/1998 | Etcheverry et al. |
| 5,721,121 A | 2/1998 | Etcheverry et al. |
| 5,728,580 A | 3/1998 | Shuler et al. |
| 5,736,506 A | 4/1998 | Naka |
| 5,770,197 A | 6/1998 | Brady et al. |
| 5,773,253 A | 6/1998 | Linsley et al. |
| 5,844,095 A | 12/1998 | Linsley et al. |
| 5,851,795 A | 12/1998 | Linsley et al. |
| 5,851,800 A | 12/1998 | Adamson et al. |
| 5,883,223 A | 3/1999 | Gray |
| 5,885,579 A | 3/1999 | Brady et al. |
| 5,885,796 A | 3/1999 | Brady et al. |
| 5,916,560 A | 6/1999 | Aruffo et al. |
| 5,968,510 A | 10/1999 | Brady et al. |
| 5,976,833 A | 11/1999 | Furukawa et al. |
| 5,977,318 A | 11/1999 | Brady et al. |
| 6,090,914 A | 7/2000 | Linsley et al. |
| 6,352,694 B1 | 3/2002 | June et al. |
| 6,444,792 B1 | 9/2002 | Gray et al. |
| 6,534,055 B1 | 3/2003 | June et al. |
| 6,641,809 B1 | 11/2003 | Brady et al. |

(Continued)

FOREIGN PATENT DOCUMENTS

WO    WO 90/05541    5/1990

(Continued)

OTHER PUBLICATIONS

Kaufmann et al. (1999) Influence of low temperature on productivity, proteome and protein phosphorylation of CHO cells. Biotechnol Bioeng. vol. 63, No. 5, pp. 573-582.*
Huang et al. (2007) A microfluidic system for automatic cell culture, J. Micromech. Microeng., vol. 17, pp. 1266-1274.*
Kaufmann, H. et al., "Influence of Low Temperature on Productivity Proteome and Protein Phosphorylation of CHO Cells", Biotechnology and Bioengineering, vol. 63(5), pp. 573-582 (1999).
Horvath, B. et al., "Temperature shift optimization in fed-batch mammalian cell culture", Abstracts of Papers American Chemical Society, vol. 221(1-2), pp. BIOT 150 (2001).

*Primary Examiner*—Jon P Weber
*Assistant Examiner*—Samuel W Liu
(74) *Attorney, Agent, or Firm*—Nickki L. Parlet; Audrey F. Sher

(57) ABSTRACT

The present invention describes methods and processes for the production of proteins, particularly glycoproteins, by animal cell or mammalian cell culture, preferably, but not limited to, fed-batch cell cultures. In one aspect, the methods comprise at least two temperature shifts performed during the culturing period, in which the temperature is lower at the end of the culturing period than at the time of initial cell culture. Throughout their duration, the culturing processes of the invention involving two or more downward shifts in temperature sustain a high viability of the cultured cells, and can yield an increased end titer of protein product, and a high quality of protein product, as determined, e.g., by sialic acid content of the produced protein. In another aspect, the methods comprise the delayed addition of polyanionic compound during the culturing period. The delayed addition of polyanionic compound sustains a high viability of the cultured cells, and can extend the growth phase, delay the onset of the death phase, and arrest the death phase.

18 Claims, 14 Drawing Sheets

U.S. PATENT DOCUMENTS

| | | |
|---|---|---|
| 6,685,941 B1 | 2/2004 | Thompson et al. |
| 6,719,972 B1 | 4/2004 | Gribben et al. |
| 6,750,334 B1 | 6/2004 | Gray et al. |
| 6,830,937 B1 | 12/2004 | Brady et al. |
| 6,951,752 B2 | 10/2005 | Reiter et al. |
| 2001/0053361 A1 | 12/2001 | Thompson et al. |
| 2002/0031510 A1 | 3/2002 | Larsen et al. |
| 2002/0039577 A1 | 4/2002 | Todderud et al. |
| 2002/0115214 A1 | 8/2002 | June et al. |
| 2002/0182211 A1* | 12/2002 | Peach et al. ............ 424/143.1 |
| 2003/0007968 A1 | 1/2003 | Adams et al. |
| 2003/0022836 A1 | 1/2003 | Larsen et al. |
| 2003/0083246 A1 | 5/2003 | Cohen et al. |
| 2003/0219863 A1 | 11/2003 | Peach et al. |
| 2004/0014171 A1 | 1/2004 | Peach et al. |
| 2004/0022787 A1 | 2/2004 | Cohen et al. |

FOREIGN PATENT DOCUMENTS

| | | |
|---|---|---|
| WO | WO 93/19767 | 10/1993 |
| WO | WO 94/28912 | 12/1994 |
| WO | WO 95/33770 | 12/1995 |
| WO | WO 97/28267 | 8/1997 |
| WO | WO 98/08934 | 3/1998 |
| WO | WO 99/61650 | 12/1999 |
| WO | WO 00/36092 | 6/2000 |
| WO | WO 00/65070 | 11/2000 |
| WO | WO 01/92337 | 12/2001 |
| WO | WO 2004/058944 | 7/2004 |
| WO | WO 2005/016266 | 2/2005 |

* cited by examiner

```
ATGGGTGTACTGCTCACACAGAGGACGCTGCTCAGTCTGGTCCTTGCACTCCTGTTTCCA    -19
M--G--V--L--L--T--Q--R--T--L--L--S--L--V--L--A--L--L--F--P--    -7

AGCATGGCGAGCATGGCAATGCACGTGGCCCAGCCTGCTGTGGTACTGGCCAGCAGCCGA    +42
S--M--A--S--M--A--M--H--V--A--Q--P--A--V--V--L--A--S--S--R--   +14
                      +1

GGCATCGCTAGCTTTGTGTGTGAGTATGCATCTCCAGGCAAAGCCACTGAGGTCCGGGTG   +102
G--I--A--S--F--V--C--E--Y--A--S--P--G--K--A--T--E--V--R--V--   +34

ACAGTGCTTCGGCAGGCTGACAGCCAGGTGACTGAAGTCTGTGCGGCAACCTACATGATG   +162
T--V--L--R--Q--A--D--S--Q--V--T--E--V--C--A--A--T--Y--M--M--   +54

GGGAATGAGTTGACCTTCCTAGATGATTCCATCTGCACGGGCACCTCCAGTGGAAATCAA   +222
G--N--E--L--T--F--L--D--D--S--I--C--T--G--T--S--S--G--N--Q--   +74

GTGAACCTCACTATCCAAGGACTGAGGGCCATGGACACGGGACTCTACATCTGCAAGGTG   +282
V--N--L--T--I--Q--G--L--R--A--M--D--T--G--L--Y--I--C--K--V--   +94

GAGCTCATGTACCCACCGCCATACTACCTGGGCATAGGCAACGGAACCCAGATTTATGTA   +342
E--L--M--Y--P--P--P--Y--Y--L--G--I--G--N--G--T--Q--I--Y--V--   +114

ATTGATCCAGAACCGTGCCCAGATTCTGATCAGGAGCCCAAATCTTCTGACAAAACTCAC   +402
I--D--P--E--P--C--P--D--S--D--Q--E--P--K--S--S--D--K--T--H--   +134

ACATCCCCACCGTCCCCAGCACCTGAAACTCCTGGGTGGATCGTCAGTCTTCCTCTTCCCC   +462
T--S--P--P--S--P--A--P--E--L--L--G--G--S--S--V--F--L--F--P--   +154

CCAAAACCCAAGGACACCCTCATGATCTCCCGGACCCCTGAGGTCACATGCGTGGTGGTG   +522
P--K--P--K--D--T--L--M--I--S--R--T--P--E--V--T--C--V--V--V--   +174

GACGTGAGCCACGAAGACCCTGAGGTCAAGTTCAACTGGTACGTGGACGGCGTGGAGGTG   +582
D--V--S--H--E--D--P--E--V--K--F--N--W--Y--V--D--G--V--E--V--   +194

CATAATGCCAAGACAAAGCCGCGGGAGGAGCAGTACAACAGCACGTACCGGGTGGTCAGC   +642
H--N--A--K--T--K--P--R--E--E--Q--Y--N--S--T--Y--R--V--V--S--   +214

GTCCTCACCGTCCTGCACCAGGACTGGCTGAATGGCAAGGAGTACAAGTGCAAGGTCTCC   +702
V--L--T--V--L--H--Q--D--W--L--N--G--K--E--Y--K--C--K--V--S--   +234

AACAAAGCCCTCCCAGCCCCCATCGAGAAAACCATCTCCAAAGCCAAAGGGCAGCCCCGA   +762
N--K--A--L--P--A--P--I--E--K--T--I--S--K--A--K--G--Q--P--R--   +254

GAACCACAGGTGTACACCCTGCCCCCATCCCGGGATGAGCTGACCAAGAACCAGGTCAGC   +822
E--P--Q--V--Y--T--L--P--P--S--R--D--E--L--T--K--N--Q--V--S--   +274

CTGACCTGCCTGGTCAAAGGCTTCTATCCCAGCGACATCGCCGTGGAGTGGGAGAGCAAT   +882
L--T--C--L--V--K--G--F--Y--P--S--D--I--A--V--E--W--E--S--N--   +294

GGGCAGCCGGAGAACAACTACAAGACCACGCCTCCCGTGCTGGACTCCGACGGCTCCTTC   +942
G--Q--P--E--N--N--Y--K--T--T--P--P--V--L--D--S--D--G--S--F--   +314

TTCCTCTACAGCAAGCTCACCGTGGACAAGAGCAGGTGGCAGCAGGGGAACGTCTTCTCA  +1002
F--L--Y--S--K--L--T--V--D--K--S--R--W--Q--Q--G--N--V--F--S--   +334

TGCTCCGTGATGCATGAGGCTCTGCACAACCACTACACGCAGAAGAGCCTCTCCCTGTCT  +1062
C--S--V--M--H--E--A--L--H--N--H--Y--T--Q--K--S--L--S--L--S--   +354

CCGGGTAAATGA
P--G--K--*
```

FIG. 3

```
ATGGGTGTACTGCTCACACAGAGGACGCTGCTCAGTCTGGTCCTTGCACTCCTGTTTCCA        -19
M--G--V--L--L--T--Q--R--T--L--L--S--L--V--L--A--L--L--P--P--        -7

AGCATGGCGAGCATGGCAATGCACGTGGCCCAGCCTGCTGTGGTACTGGCCAGCAGCCGA        +42
S--M--A--S--M--A--M--H--V--A--Q--P--A--V--V--L--A--S--S--R--        +14
                   +1

GGCATCGCTAGCTTTGTGTGTGAGTATGCATCTCCAGGCAAATATACTGAGGTCCGGGTG        +102
G--I--A--S--F--V--C--E--Y--A--S--P--G--K--Y--T--E--V--R--V--        +34

ACAGTGCTTCGGCAGGCTGACAGCCAGGTGACTGAAGTCTGTGCGGCAACCTACATGATG        +162
T--V--L--R--Q--A--D--S--Q--V--T--E--V--C--A--A--T--Y--M--M--        +54

GGGAATGAGTTGACCTTCCTAGATGATTCCATCTGCACGGGCACCTCCAGTGGAAATCAA        +222
G--N--E--L--T--F--L--D--D--S--I--C--T--G--T--S--S--G--N--Q--        +74

GTGAACCTCACTATCCAAGGACTGAGGGCCATGGACACGGGACTCTACATCTGCAAGGTG        +282
V--N--L--T--I--Q--G--L--R--A--M--D--T--G--L--Y--I--C--K--V--        +94

GAGCTCATGTACCCACCGCCATACTACGAGGGCATAGGCAACGGAACCCAGATTTATGTA        +342
E--L--M--Y--P--P--P--Y--Y--E--G--I--G--N--G--T--Q--I--Y--V--        +114

ATTGATCCAGAACCGTGCCCAGATTCTGATCAGGAGCCCAAATCTTCTGACAAAACTCAC        +402
I--D--P--E--P--C--P--D--S--D--Q--E--P--K--S--S--D--K--T--H--        +134

ACATCCCCACCGTCCCCAGCACCTGAACTCCTGGGGGGATCGTCAGTCTTCCTCTTCCCC        +462
T--S--P--P--S--P--A--P--E--L--L--G--G--S--S--V--F--L--F--P--        +154

CCAAAACCCAAGGACACCCTCATGATCTCCCGGACCCCTGAGGTCACATGCGTGGTGGTG        +522
P--K--P--K--D--T--L--M--I--S--R--T--P--E--V--T--C--V--V--V--        +174

GACGTGAGCCACGAAGACCCTGAGGTCAAGTTCAACTGGTACGTGGACGGCGTGGAGGTG        +582
D--V--S--H--E--D--P--E--V--K--F--N--W--Y--V--D--G--V--E--V--        +194

CATAATGCCAAGACAAAGCCGCGGGAGGAGCAGTACAACAGCACGTACCGTGTGGTCAGC        +642
H--N--A--K--T--K--P--R--E--E--Q--Y--N--S--T--Y--R--V--V--S--        +214

GTCCTCACCGTCCTGCACCAGGACTGGCTGAATGGCAAGGAGTACAAGTGCAAGGTCTCC        +702
V--L--T--V--L--H--Q--D--W--L--N--G--K--E--Y--K--C--K--V--S--        +234

AACAAAGCCCTCCCAGCCCCCATCGAGAAAACCATCTCCAAAGCCAAAGGGCAGCCCCGA        +762
N--K--A--L--P--A--P--I--E--K--T--I--S--K--A--K--G--Q--P--R--        +254

GAACCACAGGTGTACACCCTGCCCCCATCCCGGGATGAGCTGACCAAGAACCAGGTCAGC        +822
E--P--Q--V--Y--T--L--P--P--S--R--D--E--L--T--K--N--Q--V--S--        +274

CTGACCTGCCTGGTCAAAGGCTTCTATCCCAGCGACATCGCCGTGGAGTGGGAGAGCAAT        +882
L--T--C--L--V--K--G--F--Y--P--S--D--I--A--V--E--W--E--S--N--        +294

GGGCAGCCGGAGAACAACTACAAGACCACGCCTCCCGTGCTGGACTCCGACGGCTCCTTC        +942
G--Q--P--E--N--N--Y--K--T--T--P--P--V--L--D--S--D--G--S--F--        +314

TTCCTCTACAGCAAGCTCACCGTGGACAAGAGCAGGTGGCAGCAGGGGAACGTCTTCTCA        +1002
F--L--Y--S--K--L--T--V--D--K--S--R--W--Q--Q--G--N--V--F--S--        +334

TGCTCCGTGATGCATGAGGCTCTGCACAACCACTACACGCAGAAGAGCCTCTCCCTGTCT        +1062
C--S--V--M--H--E--A--L--H--N--H--Y--T--Q--K--S--L--S--L--S--        +354

CCGGGTAAATGA
P--G--K--*
```

FIG. 4

ONCOSTATIN M SIGNAL PEPTIDE

```
M   G   V   L   L   T   Q   R   T   L   L   S   L   V   L
ATG GGT GTA CTG CTC ACA CAG AGG ACG CTC CTC AGT CTG GTC CTT   45

-|  +|
A   L   L   F   P   S   M   A   S   M   A   N   H   V   A
GCA CTC CTG TTT CCA AGC ATG GCG AGC ATG GCA ATG CAC GTG GCC   90

Q   P   A   V   V   L   A   S   S   R   G   I   A   S   F
CAG CCT GCT GTG GTA CTG GCC AGC AGC CGA GGC ATC GCC AGC TTT   135

V   C   E   Y   A   S   P   G   K   A   T   E   V   R   V
GTG TGT GAG TAT GCA TCT CCA GGC AAA GCC ACT GAG GTC CGG GTG   180

T   V   L   R   Q   A   D   S   Q   V   T   E   V   C   A
ACA GTG CTT CGG CAG GCT GAC AGC CAG GTG ACT GAA GTC TGT GCG   225

A   T   Y   M   M   G   N   E   L   T   F   L   D   D   S
GCA ACC TAC ATG ATG GGG AAT GAG TTG ACC TTC CTA GAT GAT TCC   270

I   C   T   G   T   S   S   G   N   Q   V   N   L   T   I
ATC TGC ACG GGC ACC TCC AGT GGA AAT CAA GTG AAC CTC ACT ATC   315

Q   G   L   R   A   M   D   T   G   L   Y   I   C   K   V
CAA GGA CTG AGG GCC ATG GAC ACG GGA CTC TAC ATC TGC AAG GTG   360
```

GLYCOSYLATION SITE

```
E   L   M   Y   P   P   P   Y   Y   L   G   I   G   N   G
GAG CTC ATG TAC CCA CCG CCA TAC TAC CTG GGC ATA GGC AAC GGA   405

T   Q   I   Y   V   I   D   P   E   P   C   P   D   S   D
ACC CAG ATT TAT GTA ATT GAT CCA GAA CCG TGC CCA GAT TCT GAC   450

F   L   L   W   I   L   A   A   V   S   S   G   L   F   F
TTC CTC CTC TGG ATC CTT GCA GCA GTT AGT TCG GGG TTG TTT TTT   495

Y   S   F   L   L   T   A   V   S   L   S   K   M   L   K
TAT AGC TTT CTC CTC ACA GCT GTT TCT TTG AGC AAA ATG CTA AAG   540

K   R   S   P   L   T   T   G   V   Y   V   K   M   P   P
AAA AGA AGC CCT CTT ACA ACA GGG GTC TAT GTG AAA ATG CCC CCA   585

T   E   P   E   C   E   K   Q   F   Q   P   Y   F   I   P
ACA GAG CCA GAA TGT GAA AAG CAA TTT CAG CCT TAT TTT ATT CCC   630

I   N
ATC AAT                                                       636
```

FIG. 5

SEQUENCE LISTING

```
<160> NUMBER OF SEQ ID NOS: 6

<210> SEQ ID NO 1
<211> LENGTH: 1152
<212> TYPE: DNA
<213> ORGANISM: Artificial Sequence
<220> FEATURE:
<223> OTHER INFORMATION: CTLA4Ig, fusion protein including extracellular
      domain of human CTLA4
<220> FEATURE:
<221> NAME/KEY: CDS
<222> LOCATION: (1)..(1149)
<220> FEATURE:
<221> NAME/KEY: mat_peptide
<222> LOCATION: (79)..()

<400> SEQUENCE: 1 atg ggt gta ctg ctc aca cag agg acg ctg ctc agt ctg gtc ctt gca        48
Met Gly Val Leu Leu Thr Gln Arg Thr Leu Leu Ser Leu Val Leu Ala
    -25                 -20                 -15 ctc ctg ttt cca agc atg gcg agc atg gca atg cac gtg gcc cag cct        96
Leu Leu Phe Pro Ser Met Ala Ser Met Ala Met His Val Ala Gln Pro
-10                  -5                  -1  1               5 gct gtg gta ctg gcc agc agc cga ggc atc gct agc ttt gtg tgt gag       144
Ala Val Val Leu Ala Ser Ser Arg Gly Ile Ala Ser Phe Val Cys Glu
                 10                  15                  20 tat gca tct cca ggc aaa gcc act gag gtc cgg gtg aca gtg ctt cgg       192
Tyr Ala Ser Pro Gly Lys Ala Thr Glu Val Arg Val Thr Val Leu Arg
             25                  30                  35 cag gct gac agc cag gtg act gaa gtc tgt gcg gca acc tac atg atg       240
Gln Ala Asp Ser Gln Val Thr Glu Val Cys Ala Ala Thr Tyr Met Met
         40                  45                  50 ggg aat gag ttg acc ttc cta gat gat tcc atc tgc acg ggc acc tcc       288
Gly Asn Glu Leu Thr Phe Leu Asp Asp Ser Ile Cys Thr Gly Thr Ser
 55                  60                  65                  70 agt gga aat caa gtg aac ctc act atc caa gga ctg agg gcc atg gac       336
Ser Gly Asn Gln Val Asn Leu Thr Ile Gln Gly Leu Arg Ala Met Asp
                 75                  80                  85 acg gga ctc tac atc tgc aag gtg gag ctc atg tac cca ccg cca tac       384
Thr Gly Leu Tyr Ile Cys Lys Val Glu Leu Met Tyr Pro Pro Pro Tyr
             90                  95                 100 tac ctg ggc ata ggc aac gga acc cag att tat gta att gat cca gaa       432
Tyr Leu Gly Ile Gly Asn Gly Thr Gln Ile Tyr Val Ile Asp Pro Glu
        105                 110                 115 ccg tgc cca gat tct gat cag gag ccc aaa tct tct gac aaa act cac       480
Pro Cys Pro Asp Ser Asp Gln Glu Pro Lys Ser Ser Asp Lys Thr His
        120                 125                 130 aca tgc cca ccg tgc cca gca cct gaa ctc ctg ggt gga tcg tca gtc       528
Thr Cys Pro Pro Cys Pro Ala Pro Glu Leu Leu Gly Gly Ser Ser Val
135                 140                 145                 150
```

-continued

| | | |
|---|---|---|
| ttc ctc ttc ccc cca aaa ccc aag gac acc ctc atg atc tcc cgg acc<br>Phe Leu Phe Pro Pro Lys Pro Lys Asp Thr Leu Met Ile Ser Arg Thr<br>                                    155                                160                          165 | 576 |
| cct gag gtc aca tgc gtg gtg gtg gac gtg agc cac gaa gac cct gag<br>Pro Glu Val Thr Cys Val Val Val Asp Val Ser His Glu Asp Pro Glu<br>                170                            175                          180 | 624 |
| gtc aag ttc aac tgg tac gtg gac ggc gtg gag gtg cat aat gcc aag<br>Val Lys Phe Asn Trp Tyr Val Asp Gly Val Glu Val His Asn Ala Lys<br>                    185                          190                         195 | 672 |
| aca aag ccg cgg gag gag cag tac aac agc acg tac cgg gtg gtc agc<br>Thr Lys Pro Arg Glu Glu Gln Tyr Asn Ser Thr Tyr Arg Val Val Ser<br>       200                        205                         210 | 720 |
| gtc ctc acc gtc ctg cac cag gac tgg ctg aat ggc aag gag tac aag<br>Val Leu Thr Val Leu His Gln Asp Trp Leu Asn Gly Lys Glu Tyr Lys<br>215                         220                         225                      230 | 768 |
| tgc aag gtc tcc aac aaa gcc ctc cca gcc ccc atc gag aaa acc atc<br>Cys Lys Val Ser Asn Lys Ala Leu Pro Ala Pro Ile Glu Lys Thr Ile<br>                    235                          240                         245 | 816 |
| tcc aaa gcc aaa ggg cag ccc cga gaa cca cag gtg tac acc ctg ccc<br>Ser Lys Ala Lys Gly Gln Pro Arg Glu Pro Gln Val Tyr Thr Leu Pro<br>       250                        255                         260 | 864 |
| cca tcc cgg gat gag ctg acc aag aac cag gtc agc ctg acc tgc ctg<br>Pro Ser Arg Asp Glu Leu Thr Lys Asn Gln Val Ser Leu Thr Cys Leu<br>                    265                          270                         275 | 912 |
| gtc aaa ggc ttc tat ccc agc gac atc gcc gtg gag tgg gag agc aat<br>Val Lys Gly Phe Tyr Pro Ser Asp Ile Ala Val Glu Trp Glu Ser Asn<br>       280                        285                         290 | 960 |
| ggg cag ccg gag aac aac tac aag acc acg cct ccc gtg ctg gac tcc<br>Gly Gln Pro Glu Asn Asn Tyr Lys Thr Thr Pro Pro Val Leu Asp Ser<br>295                         300                         305                      310 | 1008 |
| gac ggc tcc ttc ttc ctc tac agc aag ctc acc gtg gac aag agc agg<br>Asp Gly Ser Phe Phe Leu Tyr Ser Lys Leu Thr Val Asp Lys Ser Arg<br>                    315                          320                         325 | 1056 |
| tgg cag cag ggg aac gtc ttc tca tgc tcc gtg atg cat gag gct ctg<br>Trp Gln Gln Gly Asn Val Phe Ser Cys Ser Val Met His Glu Ala Leu<br>       330                        335                         340 | 1104 |
| cac aac cac tac acg cag aag agc ctc tcc ctg tct ccg ggt aaa tga<br>His Asn His Tyr Thr Gln Lys Ser Leu Ser Leu Ser Pro Gly Lys<br>                    345                          350                         355 | 1152 |

<210> SEQ ID NO 2
<211> LENGTH: 383
<212> TYPE: PRT
<213> ORGANISM: Artificial Sequence
<220> FEATURE:
<223> OTHER INFORMATION: CTLA4Ig, fusion protein including extracellular
     domain of human CTLA4

<400> SEQUENCE: 2

Met Gly Val Leu Leu Thr Gln Arg Thr Leu Leu Ser Leu Val Leu Ala
        -25                   -20                        -15

Leu Leu Phe Pro Ser Met Ala Ser Met Ala Met His Val Ala Gln Pro
-10                     -5                  -1  1                   5

Ala Val Val Leu Ala Ser Ser Arg Gly Ile Ala Ser Phe Val Cys Glu
                 10                           15                         20

Tyr Ala Ser Pro Gly Lys Ala Thr Glu Val Arg Val Thr Val Leu Arg
         25                        30                         35

Gln Ala Asp Ser Gln Val Thr Glu Val Cys Ala Ala Thr Tyr Met Met
    40                        45                         50

Gly Asn Glu Leu Thr Phe Leu Asp Asp Ser Ile Cys Thr Gly Thr Ser

```
                55                  60                  65                  70
            Ser Gly Asn Gln Val Asn Leu Thr Ile Gln Gly Leu Arg Ala Met Asp
                            75                  80                  85
            Thr Gly Leu Tyr Ile Cys Lys Val Glu Leu Met Tyr Pro Pro Pro Tyr
                            90                  95                 100
            Tyr Leu Gly Ile Gly Asn Gly Thr Gln Ile Tyr Val Ile Asp Pro Glu
                           105                 110                 115
            Pro Cys Pro Asp Ser Asp Gln Glu Pro Lys Ser Ser Asp Lys Thr His
                           120                 125                 130
            Thr Ser Pro Pro Ser Pro Ala Pro Glu Leu Leu Gly Gly Ser Ser Val
            135                 140                 145                 150
            Phe Leu Phe Pro Pro Lys Pro Lys Asp Thr Leu Met Ile Ser Arg Thr
                           155                 160                 165
            Pro Glu Val Thr Cys Val Val Val Asp Val Ser His Glu Asp Pro Glu
                           170                 175                 180
            Val Lys Phe Asn Trp Tyr Val Asp Gly Val Glu Val His Asn Ala Lys
                           185                 190                 195
            Thr Lys Pro Arg Glu Glu Gln Tyr Asn Ser Thr Tyr Arg Val Val Ser
                200                 205                 210
            Val Leu Thr Val Leu His Gln Asp Trp Leu Asn Gly Lys Glu Tyr Lys
            215                 220                 225                 230
            Cys Lys Val Ser Asn Lys Ala Leu Pro Ala Pro Ile Glu Lys Thr Ile
                           235                 240                 245
            Ser Lys Ala Lys Gly Gln Pro Arg Glu Pro Gln Val Tyr Thr Leu Pro
                           250                 255                 260
            Pro Ser Arg Asp Glu Leu Thr Lys Asn Gln Val Ser Leu Thr Cys Leu
                           265                 270                 275
            Val Lys Gly Phe Tyr Pro Ser Asp Ile Ala Val Glu Trp Glu Ser Asn
                280                 285                 290
            Gly Gln Pro Glu Asn Asn Tyr Lys Thr Thr Pro Pro Val Leu Asp Ser
            295                 300                 305                 310
            Asp Gly Ser Phe Phe Leu Tyr Ser Lys Leu Thr Val Asp Lys Ser Arg
                           315                 320                 325
            Trp Gln Gln Gly Asn Val Phe Ser Cys Ser Val Met His Glu Ala Leu
                           330                 335                 340
            His Asn His Tyr Thr Gln Lys Ser Leu Ser Leu Ser Pro Gly Lys
                           345                 350                 355

<210> SEQ ID NO 3
<211> LENGTH: 1152
<212> TYPE: DNA
<213> ORGANISM: Artificial Sequence
<220> FEATURE:
<223> OTHER INFORMATION: L104EA29YIg, fusion protein including mutated
      extracellular domain of human CTLA4
<220> FEATURE:
<221> NAME/KEY: CDS
<222> LOCATION: (1)..(1149)
<220> FEATURE:
<221> NAME/KEY: mat_peptide
<222> LOCATION: (79)..()

<400> SEQUENCE: 3 atg ggt gta ctg ctc aca cag agg acg ctg ctc agt ctg gtc ctt gca        48
Met Gly Val Leu Leu Thr Gln Arg Thr Leu Leu Ser Leu Val Leu Ala
    -25                 -20                 -15 ctc ctg ttt cca agc atg gcg agc atg gca atg cac gtg gcc cag cct        96
Leu Leu Phe Pro Ser Met Ala Ser Met Ala Met His Val Ala Gln Pro
```

```
                -10                     -5              -1  1              5
          gct gtg gta ctg gcc agc agc cga ggc atc gct agc ttt gtg tgt gag       144
          Ala Val Val Leu Ala Ser Ser Arg Gly Ile Ala Ser Phe Val Cys Glu
                           10                  15                  20 tat gca tct cca ggc aaa tat act gag gtc cgg gtg aca gtg ctt cgg       192
          Tyr Ala Ser Pro Gly Lys Tyr Thr Glu Val Arg Val Thr Val Leu Arg
                           25                  30                  35 cag gct gac agc cag gtg act gaa gtc tgt gcg gca acc tac atg atg       240
          Gln Ala Asp Ser Gln Val Thr Glu Val Cys Ala Ala Thr Tyr Met Met
                   40                  45                  50 ggg aat gag ttg acc ttc cta gat gat tcc atc tgc acg ggc acc tcc       288
          Gly Asn Glu Leu Thr Phe Leu Asp Asp Ser Ile Cys Thr Gly Thr Ser
          55                  60                  65                  70 agt gga aat caa gtg aac ctc act atc caa gga ctg agg gcc atg gac       336
          Ser Gly Asn Gln Val Asn Leu Thr Ile Gln Gly Leu Arg Ala Met Asp
                           75                  80                  85 acg gga ctc tac atc tgc aag gtg gag ctc atg tac cca ccg cca tac       384
          Thr Gly Leu Tyr Ile Cys Lys Val Glu Leu Met Tyr Pro Pro Pro Tyr
                           90                  95                 100 tac gag ggc ata ggc aac gga acc cag att tat gta att gat cca gaa       432
          Tyr Glu Gly Ile Gly Asn Gly Thr Gln Ile Tyr Val Ile Asp Pro Glu
                          105                 110                 115 ccg tgc cca gat tct gat cag gag ccc aaa tct tct gac aaa act cac       480
          Pro Cys Pro Asp Ser Asp Gln Glu Pro Lys Ser Ser Asp Lys Thr His
                  120                 125                 130 aca tcc cca ccg tcc cca gca cct gaa ctc ctg ggg gga tcg tca gtc       528
          Thr Ser Pro Pro Ser Pro Ala Pro Glu Leu Leu Gly Gly Ser Ser Val
          135                 140                 145                 150 ttc ctc ttc ccc cca aaa ccc aag gac acc ctc atg atc tcc cgg acc       576
          Phe Leu Phe Pro Pro Lys Pro Lys Asp Thr Leu Met Ile Ser Arg Thr
                          155                 160                 165 cct gag gtc aca tgc gtg gtg gtg gac gtg agc cac gaa gac cct gag       624
          Pro Glu Val Thr Cys Val Val Val Asp Val Ser His Glu Asp Pro Glu
                  170                 175                 180 gtc aag ttc aac tgg tac gtg gac ggc gtg gag gtg cat aat gcc aag       672
          Val Lys Phe Asn Trp Tyr Val Asp Gly Val Glu Val His Asn Ala Lys
                          185                 190                 195 aca aag ccg cgg gag gag cag tac aac agc acg tac cgt gtg gtc agc       720
          Thr Lys Pro Arg Glu Glu Gln Tyr Asn Ser Thr Tyr Arg Val Val Ser
                  200                 205                 210 gtc ctc acc gtc ctg cac cag gac tgg ctg aat ggc aag gag tac aag       768
          Val Leu Thr Val Leu His Gln Asp Trp Leu Asn Gly Lys Glu Tyr Lys
          215                 220                 225                 230 tgc aag gtc tcc aac aaa gcc ctc cca gcc ccc atc gag aaa acc atc       816
          Cys Lys Val Ser Asn Lys Ala Leu Pro Ala Pro Ile Glu Lys Thr Ile
                          235                 240                 245 tcc aaa gcc aaa ggg cag ccc cga gaa cca cag gtg tac acc ctg ccc       864
          Ser Lys Ala Lys Gly Gln Pro Arg Glu Pro Gln Val Tyr Thr Leu Pro
                  250                 255                 260 cca tcc cgg gat gag ctg acc aag aac cag gtc agc ctg acc tgc ctg       912
          Pro Ser Arg Asp Glu Leu Thr Lys Asn Gln Val Ser Leu Thr Cys Leu
                          265                 270                 275 gtc aaa ggc ttc tat ccc agc gac atc gcc gtg gag tgg gag agc aat       960
          Val Lys Gly Phe Tyr Pro Ser Asp Ile Ala Val Glu Trp Glu Ser Asn
          280                 285                 290 ggg cag ccg gag aac aac tac aag acc acg cct ccc gtg ctg gac tcc      1008
          Gly Gln Pro Glu Asn Asn Tyr Lys Thr Thr Pro Pro Val Leu Asp Ser
          295                 300                 305                 310 gac ggc tcc ttc ttc ctc tac agc aag ctc acc gtg gac aag agc agg      1056
```

```
Asp Gly Ser Phe Phe Leu Tyr Ser Lys Leu Thr Val Asp Lys Ser Arg
            315                 320                 325 tgg cag cag ggg aac gtc ttc tca tgc tcc gtg atg cat gag gct ctg      1104
Trp Gln Gln Gly Asn Val Phe Ser Cys Ser Val Met His Glu Ala Leu
            330                 335                 340 cac aac cac tac acg cag aag agc ctc tcc ctg tct ccg ggt aaa tga      1152
His Asn His Tyr Thr Gln Lys Ser Leu Ser Leu Ser Pro Gly Lys
            345                 350                 355

<210> SEQ ID NO 4
<211> LENGTH: 383
<212> TYPE: PRT
<213> ORGANISM: Artificial Sequence
<220> FEATURE:
<223> OTHER INFORMATION: L104EA29YIg, fusion protein including mutated
      extracellular domain of human CTLA4

<400> SEQUENCE: 4

Met Gly Val Leu Leu Thr Gln Arg Thr Leu Leu Ser Leu Val Leu Ala
    -25                 -20                 -15

Leu Leu Phe Pro Ser Met Ala Ser Met Ala Met His Val Ala Gln Pro
-10                  -5              -1   1                  5

Ala Val Val Leu Ala Ser Ser Arg Gly Ile Ala Ser Phe Val Cys Glu
                10                  15                  20

Tyr Ala Ser Pro Gly Lys Tyr Thr Glu Val Arg Val Thr Val Leu Arg
            25                  30                  35

Gln Ala Asp Ser Gln Val Thr Glu Val Cys Ala Ala Thr Tyr Met Met
    40                  45                  50

Gly Asn Glu Leu Thr Phe Leu Asp Asp Ser Ile Cys Thr Gly Thr Ser
55                  60                  65                  70

Ser Gly Asn Gln Val Asn Leu Thr Ile Gln Gly Leu Arg Ala Met Asp
                75                  80                  85

Thr Gly Leu Tyr Ile Cys Lys Val Glu Leu Met Tyr Pro Pro Pro Tyr
            90                  95                  100

Tyr Glu Gly Ile Gly Asn Gly Thr Gln Ile Tyr Val Ile Asp Pro Glu
        105                 110                 115

Pro Cys Pro Asp Ser Asp Gln Glu Pro Lys Ser Ser Asp Lys Thr His
    120                 125                 130

Thr Ser Pro Pro Ser Pro Ala Pro Glu Leu Leu Gly Gly Ser Ser Val
135                 140                 145                 150

Phe Leu Phe Pro Pro Lys Pro Lys Asp Thr Leu Met Ile Ser Arg Thr
                155                 160                 165

Pro Glu Val Thr Cys Val Val Val Asp Val Ser His Glu Asp Pro Glu
            170                 175                 180

Val Lys Phe Asn Trp Tyr Val Asp Gly Val Glu Val His Asn Ala Lys
        185                 190                 195

Thr Lys Pro Arg Glu Glu Gln Tyr Asn Ser Thr Tyr Arg Val Val Ser
    200                 205                 210

Val Leu Thr Val Leu His Gln Asp Trp Leu Asn Gly Lys Glu Tyr Lys
215                 220                 225                 230

Cys Lys Val Ser Asn Lys Ala Leu Pro Ala Pro Ile Glu Lys Thr Ile
                235                 240                 245

Ser Lys Ala Lys Gly Gln Pro Arg Glu Pro Gln Val Tyr Thr Leu Pro
            250                 255                 260

Pro Ser Arg Asp Glu Leu Thr Lys Asn Gln Val Ser Leu Thr Cys Leu
        265                 270                 275
```

-continued

```
Val Lys Gly Phe Tyr Pro Ser Asp Ile Ala Val Glu Trp Glu Ser Asn
    280                 285                 290
Gly Gln Pro Glu Asn Asn Tyr Lys Thr Thr Pro Pro Val Leu Asp Ser
295                 300                 305                 310
Asp Gly Ser Phe Phe Leu Tyr Ser Lys Leu Thr Val Asp Lys Ser Arg
                315                 320                 325
Trp Gln Gln Gly Asn Val Phe Ser Cys Ser Val Met His Glu Ala Leu
            330                 335                 340
His Asn His Tyr Thr Gln Lys Ser Leu Ser Leu Ser Pro Gly Lys
        345                 350                 355

<210> SEQ ID NO 5
<211> LENGTH: 636
<212> TYPE: DNA
<213> ORGANISM: Homo Sapiens
<220> FEATURE:
<221> NAME/KEY: CDS
<222> LOCATION: (1)..(636)
<220> FEATURE:
<221> NAME/KEY: mat_peptide
<222> LOCATION: (79)..()

<400> SEQUENCE: 5 atg ggt gta ctg ctc aca cag agg acg ctg ctc agt ctg gtc ctt gca        48
Met Gly Val Leu Leu Thr Gln Arg Thr Leu Leu Ser Leu Val Leu Ala
    -25                 -20                 -15 ctc ctg ttt cca agc atg gcg agc atg gca atg cac gtg gcc cag cct        96
Leu Leu Phe Pro Ser Met Ala Ser Met Ala Met His Val Ala Gln Pro
-10                  -5                  -1   1               5 gct gtg gta ctg gcc agc agc cga ggc atc gcc agc ttt gtg tgt gag       144
Ala Val Val Leu Ala Ser Ser Arg Gly Ile Ala Ser Phe Val Cys Glu
                10                  15                  20 tat gca tct cca ggc aaa gcc act gag gtc cgg gtg aca gtg ctt cgg       192
Tyr Ala Ser Pro Gly Lys Ala Thr Glu Val Arg Val Thr Val Leu Arg
            25                  30                  35 cag gct gac agc cag gtg act gaa gtc tgt gcg gca acc tac atg atg       240
Gln Ala Asp Ser Gln Val Thr Glu Val Cys Ala Ala Thr Tyr Met Met
        40                  45                  50 ggg aat gag ttg acc ttc cta gat gat tcc atc tgc acg ggc acc tcc       288
Gly Asn Glu Leu Thr Phe Leu Asp Asp Ser Ile Cys Thr Gly Thr Ser
55                  60                  65                  70 agt gga aat caa gtg aac ctc act atc caa gga ctg agg gcc atg gac       336
Ser Gly Asn Gln Val Asn Leu Thr Ile Gln Gly Leu Arg Ala Met Asp
                75                  80                  85 acg gga ctc tac atc tgc aag gtg gag ctc atg tac cca ccg cca tac       384
Thr Gly Leu Tyr Ile Cys Lys Val Glu Leu Met Tyr Pro Pro Pro Tyr
            90                  95                  100 tac ctg ggc ata ggc aac gga acc cag att tat gta att gat cca gaa       432
Tyr Leu Gly Ile Gly Asn Gly Thr Gln Ile Tyr Val Ile Asp Pro Glu
        105                 110                 115 ccg tgc cca gat tct gac ttc ctc ctc tgg atc ctt gca gca gtt agt       480
Pro Cys Pro Asp Ser Asp Phe Leu Leu Trp Ile Leu Ala Ala Val Ser
    120                 125                 130 tcg ggg ttg ttt ttt tat agc ttt ctc ctc aca gct gtt tct ttg agc       528
Ser Gly Leu Phe Phe Tyr Ser Phe Leu Leu Thr Ala Val Ser Leu Ser
135                 140                 145                 150 aaa atg cta aag aaa aga agc cct ctt aca aca ggg gtc tat gtg aaa       576
Lys Met Leu Lys Lys Arg Ser Pro Leu Thr Thr Gly Val Tyr Val Lys
                155                 160                 165 atg ccc cca aca gag cca gaa tgt gaa aag caa ttt cag cct tat ttt       624
Met Pro Pro Thr Glu Pro Glu Cys Glu Lys Gln Phe Gln Pro Tyr Phe
```

-continued

```
               170              175              180
att ccc atc aat                                                            636
Ile Pro Ile Asn
        185

<210> SEQ ID NO 6
<211> LENGTH: 212
<212> TYPE: PRT
<213> ORGANISM: Homo Sapiens

<400> SEQUENCE: 6

Met Gly Val Leu Leu Thr Gln Arg Thr Leu Leu Ser Leu Val Leu Ala
    -25             -20                 -15
Leu Leu Phe Pro Ser Met Ala Ser Met Ala Met His Val Ala Gln Pro
-10             -5                  -1  1                    5
Ala Val Val Leu Ala Ser Ser Arg Gly Ile Ala Ser Phe Val Cys Glu
                10                  15                  20
Tyr Ala Ser Pro Gly Lys Ala Thr Glu Val Arg Val Thr Val Leu Arg
                25                  30                  35
Gln Ala Asp Ser Gln Val Thr Glu Val Cys Ala Ala Thr Tyr Met Met
    40                  45                  50
Gly Asn Glu Leu Thr Phe Leu Asp Asp Ser Ile Cys Thr Gly Thr Ser
55                  60                  65                  70
Ser Gly Asn Gln Val Asn Leu Thr Ile Gln Gly Leu Arg Ala Met Asp
                75                  80                  85
Thr Gly Leu Tyr Ile Cys Lys Val Glu Leu Met Tyr Pro Pro Pro Tyr
                90                  95                  100
Tyr Leu Gly Ile Gly Asn Gly Thr Gln Ile Tyr Val Ile Asp Pro Glu
                105                 110                 115
Pro Cys Pro Asp Ser Asp Phe Leu Leu Trp Ile Leu Ala Ala Val Ser
    120                 125                 130
Ser Gly Leu Phe Phe Tyr Ser Phe Leu Leu Thr Ala Val Ser Leu Ser
135                 140                 145                 150
Lys Met Leu Lys Lys Arg Ser Pro Leu Thr Thr Gly Val Tyr Val Lys
                155                 160                 165
Met Pro Pro Thr Glu Pro Glu Cys Glu Lys Gln Phe Gln Pro Tyr Phe
                170                 175                 180
Ile Pro Ile Asn
        185
```

MAMMALIAN CELL CULTURE PROCESSES FOR PROTEIN PRODUCTION

This invention claims priority from provisional U.S. application Ser. No. 60/436,101 filed Dec. 23, 2002, which is incorporated herein by reference in its entirety.

FIELD OF THE INVENTION

The present invention relates to new methods and processes for culturing mammalian cells which produce a protein product, preferably a glycosylated protein product. Performance of the cell culturing methods and processes result in high cell viability and can also result in high product quality and quantity, extension of the growth phase, delay of onset of the death phase, and arrest of the death phase.

BACKGROUND OF THE INVENTION

Animal cell culture, notably mammalian cell culture, is preferably used for the expression of recombinantly produced, glycosylated proteins for therapeutic and/or prophylactic applications. Glycosylation patterns of recombinant glycoproteins are important, because the oligosaccharide side chains of glycoproteins affect protein function, as well as the intramolecular interactions between different regions of a protein. Such intramolecular interactions are involved in protein conformation and tertiary structure of the glycoprotein. (See, e.g., A. Wittwer et al., 1990, Biochemistry, 29:4175-4180; Hart, 1992, Curr. Op. Cell Biol., 4:1017-1023; Goochee et al., 1991, Bio/Technol., 9:1347-1355; and R. B. Parekh, 1991, Curr. Op. Struct. Biol., 1:750-754). In addition, oligosaccharides may function to target a particular polypeptide to certain structures based on specific cellular carbohydrate receptors. (M. P. Bevilacqua et al., 1993, J. Clin. Invest., 91:379-387; R. M. Nelson et al., 1993, J. Clin. Invest., 91:1157-1166; K. E. Norgard et al., 1993, Proc. Natl. Acad. Sci. USA, 90:1068-1072; and Y. Imai et al., 1993, Nature, 361-555-557).

The terminal sialic acid component of a glycoprotein oligosaccharide side chain is known to have an effect on numerous aspects and properties of a glycoprotein, including absorption, solubility, thermal stability, serum half life, clearance from the serum, as well as its physical and chemical structure/behavior and its immunogenicity. (A. Varki, 1993, Glycobiology, 3:97-100; R. B. Parekh, Id., Goochee et al., Id., J. Paulson et al., 1989, TIBS, 14:272-276; and A. Kobata, 1992, Eur. J. Biochem., 209:483-501; E. Q. Lawson et al., 1983, Arch. Biochem. Biophys., 220:572-575; and E. Tsuda et al., 1990, Eur. J. Biochem., 188:405-411).

In general, protein expression levels in mammalian cell culture-based systems are considerably lower than in microbial expression systems, for example, bacterial or yeast expression systems. However, bacterial and yeast cells are limited in their ability to optimally express high molecular weight protein products, to properly fold a protein having a complex steric structure, and/or to provide the necessary post-translational modifications to mature an expressed glycoprotein, thereby affecting the immunogenicity and clearance rate of the product.

As a consequence of the limitations of the culturing of animal or mammalian cells, particularly animal or mammalian cells which produce recombinant products, the manipulation of a variety of parameters has been investigated, including the employment of large-scale culture vessels; altering basic culture conditions, such as incubation temperature, dissolved oxygen concentration, pH, and the like; the use of different types of media and additives to the media; and increasing the density of the cultured cells. In addition, process development for mammalian cell culture would benefit from advances in the ability to extend run times to increase final product concentration while maintaining high product quality. An important product quality parameter is the degree and completeness of the glycosylation structure of a polypeptide product, with sialic acid content commonly used as a measure of glycoprotein quality.

Run times of cell culture processes, particularly non-continuous processes, are usually limited by the remaining viability of the cells, which typically declines over the course of the run. The maximum possible extension of high cell viabilities is therefore desired. Product quality concerns also offer a motivation for minimizing decreases in viable cell density and maintaining high cell viability, as cell death can release sialidases to the culture supernatant, which may reduce the sialic acid content of the protein expressed. Protein purification concerns offer yet another motivation for minimizing decreases in viable cell density and maintaining high cell viability. The presence of cell debris and the contents of dead cells in the culture can negatively impact on the ability to isolate and/or purify the protein product at the end of the culturing run. By keeping cells viable for a longer period of time in culture, there is thus a concomitant reduction in the contamination of the culture medium by cellular proteins and enzymes, e.g., cellular proteases and sialidases, that can cause degradation and ultimate reduction in quality of the desired glycoprotein produced by the cells.

Various parameters have been investigated to achieve high cell viability in cell cultures. One parameter involved a single lowering of the culture temperature following initial culturing at 37° C. (for example, Roessler et al., 1996, Enzyme and Microbial Technology, 18:423-427; U.S. Pat. Nos. 5,705,364 and 5,721,121 to T. Etcheverry et al., 1998; U.S. Pat. No. 5,976,833 to K. Furukawa et al., 1999; U.S. Pat. No. 5,851,800 to L. Adamson et al.; WO 99/61650 and WO 00/65070 to Genentech, Inc.; WO 00/36092 to Biogen, Inc.; and U.S. Pat. No. 4,357,422 to Girard et al.).

Other parameters investigated involved the addition of components to the culture. The growth factor inhibitor suramin was shown to prevent apoptosis during exponential growth of Chinese Hamster Ovary (CHO) K1:CycE cells (Zhangi et al., Biotechnol. Prog. 2000, 16, 319-325). However, suramin did not protect against apoptosis during the death phase. As a result, suramin was capable of maintaining high viability during the growth phase, but did not allow for an extension of culture longevity. The same authors report that for the CHO 111-10PF cell line, dextran sulfate and polyvinyl sulfate could, similarly to suramin, increase day 3 viable cell density and viability relative to the control culture. The effect of dextran sulfate or polyvinyl sulfate during the death phase was however not reported. Suramin, dextran sulfate and polyvinyl sulfate were also reported to be effective at preventing cell aggregation.

Heparin has been supplemented to animal cell culture media in order to adapt anchorage-dependant cell lines to suspension conditions (e.g. U.S. Pat. No. 5,348,877 to McKenna and Granados, 1994). Heparin is also known to bind to growth factors, such as the heparin-binding EGF-like growth factor (HB-EGF; Raab and Klagsbrun, Biochim. Biophys. Acta 1997, 1333, F179-F199). Cell surface heparan sulfate proteoglycans (HSPG) reportedly enhance HB-EGF binding and bioactivity for certain cell types including wild-type CHO cells (Raab and Klagsbrun, 1997). [Heparan sulfate only differs from heparin in that it has fewer N- and O-sulfate groups and more N-acetyl groups (McKenna and Granados, 1994). For the purpose of this disclosure, heparin and heparan sulfate are considered equivalent and will generically be referred to as heparin.] It has been proposed, for the heparin-binding growth factor FGF-2, that binding to HSPG increases the local FGF-2 concentration on the cell surface, which in turn increases the probability of FGF-2 binding to the tyrosine kinase receptors of the cells (Raab and Klagsbrun, 1997). It has been shown that pentosan polysulfate can block the action of heparin-binding growth factors on cultured cells (Zugmaier et al., J. Nat. Cancer Inst. 1992, 84, 1716-1724.

Patent literature on the use of dextran sulfate in animal cell culture pertain to the supplementation of dextran sulfate to a medium in order: 1) To improve growth rate and increase the number of population doublings before senescence for human endothelial cells (U.S. Pat. Nos. 4,994,387 and 5,132,223 to Levine et al., 1991, 1992); 2) To increase recombinant protein yield in mammalian cell lines (U.S. Pat. No. 5,318,898 to Israel, 1994); 3) To induce single cell suspension in insect cell lines (U.S. Pat. No. 5,728,580 to Shuler and Dee, 1996); 4) To increase growth-promoting activity of human hepatocyte-growth factor and to suppress its degradation (U.S. Pat. Nos. 5,545,722 and 5,736,506 to Naka, 1996 and 1998); 5) To increase viable cell density and recombinant protein expression (WO 98/08934 to Gorfien et al., 1997).

In all reported cases referring to the presence or supplementation of dextran sulfate in a medium, dextran sulfate was present throughout the culture time in that given medium. In no case were the benefits of a delayed addition reported. Moreover, it has never been reported that dextran sulfate can delay the onset of the death phase, extend the growth phase, or arrest the death phase.

With increasing product concentration in the culture, it can be observed in cell culture processes that the product quality decreases, as determined by the measured sialic acid content of the oligosaccharide glycostructure. Usually, a lower limit for an acceptable sialic acid content exists as determined by drug clearance studies. High abundance of a protein produced by cells in culture is optimally accompanied by high quality of the protein that is ultimately recovered for an intended use.

Recombinantly produced protein products that are properly glycosylated are increasingly becoming medically and clinically important for use as therapeutics, treatments and prophylactics. Therefore, the development of reliable cell culture processes that economically and efficiently achieve an increased final protein product concentration, in conjunction with a high level of product quality, such as is determined by sialic acid content, fulfills both a desired and needed goal in the art.

SUMMARY OF THE INVENTION

The present invention provides new processes for the production of proteins, preferably recombinant protein products, more preferably glycoprotein products, by animal or mammalian cell cultures. These new processes achieve increased cell viability.

One aspect of this invention concerns the use two or more temperature shifts. In this aspect, cell culture processes of this invention can advantageously achieve an enhanced final titer or concentration of product, e.g., glycoprotein, as well as an enhanced sialic acid content of the glycoprotein produced by the cultured cells. More specifically, in accordance with this invention, two or more temperature shifts during the cell culturing period sustain a high cell viability of the cells in the culture and can provide a high quantity and quality of produced product throughout an entire culture run. Also, according to one aspect of the invention, the two or more temperature shifts comprising the culturing processes can advantageously allow for an extension of the production phase of the culture. During the extended production phase, the titer of the desired product is increased; the product quality, as characterized by sialic acid content, is maintained at a high level; and cell viability is also maintained at a high level. In addition, the extended production phase associated with the culturing processes of the invention allows for the production of product beyond that which is produced during a standard production phase.

In one aspect of the present invention, multi-step temperature shifts, preferably, timed multi-step temperature shifts comprising two or more downward temperature shifts, are used in the culturing of mammalian cells to produce a desired protein product, particularly, a glycoprotein product. Two or more (i.e., at least two) temperature shifts, which may be performed after the growth phase of the culture, comprise the processes of this invention. With the at least two temperature shifts, preferably with approximately four day increments between the shifts, a high protein yield with a concomitant high sialic acid content of the desired protein product can be achieved. The multiple temperature shifts comprising the culturing methods can achieve both high quality and quantity of protein product, as well as sustain cell viability for the duration of a culturing period.

In accordance with another aspect of this invention, the culturing processes (methods) involving two or more temperature shifts can allow cells to be maintained in culture for a period of time that advantageously extends the culturing run to achieve high quality and quantity of protein production. Such an extension of the protein production phase advantageously provided by this invention refers to a production phase that can be carried out beyond the protein production that is attained when no temperature shift, or only one temperature shift, is used in the culture run. The extended production phase is associated with the multiple temperature shifts that comprise the described cell culturing methods. According to the new cell culture methods of this invention, the combination of a second, third, fourth, or further downward shift in temperature with a first temperature shift allows the cell cultures to sustain a high cell viability and provides, in an embodiment of the invention, for an extended production phase during which the titer of the protein product is increased and product quality, as characterized by sialic acid content, remains high until the end of the culture run.

A culture run as used herein refers to the culturing period, preferably, the entire culture period. For a culture run comprising two or more temperature shifts, the length of the entire culture run can last from as short as just after the second temperature shift (for example, about 10-14 days) to as long as about 28 to 30 days, or more. For a culture run comprising three (or more) temperature shifts, the length of the entire run can last from as short as just after the third (or the last) temperature shift (for example, about 14 to 21 days) to as long as about 28 to 30 days or more. Thus, in accordance with the methods of the present invention, cells can be cultured for a total run period of greater than 10 days, greater than 14 days, or greater than 21 days. Preferably, the culture run lasts for at least about 10 to 14 days to about 21 to 30 days, or more The total culturing run can comprise two, three, four, or more step temperature shifts. As a nonlimiting example, a two-step temperature shift is carried out as follows: the culture temperature is initially maintained at 37° C., or near 37° C., from day 0 to about day 6; from about day 6 to about day 10, the culture temperature is maintained at 34° C., or near 34° C.; and from about day 10 onward, e.g., to about day 14 to 28, to about day 14 to 18, or to the end of the culture run, the culture temperature is maintained at 32° C., or near 32° C. A three-step temperature shift culture procedure according to this invention comprises the following nonlimiting, exemplifying format: the cell culture temperature is controlled at 37° C., or near 37° C., from day 0 to about day 6; from about day 6 to about day 10, the culture temperature is maintained at 34° C., or near 34° C.; from about day 10 to about day 14, the culture temperature is maintained at 32° C., or near 32° C.; and from about day 14 onward, e.g., to about day 21 to day 30, or longer, i.e., to the end of the run, the culture temperature is maintained at 30° C., or near 30° C.

Thus, employment of the present cell culturing methods comprising two or more temperature shifts in which high quantity and quality of protein production is achieved is beneficial not only for culture runs having "shorter", e.g., standard, durations (e.g., about 10 to about 14 days), but also for culture runs which can endure longer than the standard production run. Such longer duration culturing runs are achieved because the methods of this invention can provide an extension of the initial or standard production phase of protein production by the cultured cells (the initial or standard production phase occurs, in general, at about days 6 to 14). For example, by employing two, three, or more temperature shifts in the culture run in accordance with this invention, high quality and quantity of protein production and cell viability can be maintained and sustained for a total run time of about 10-14 days to a total run time of about 21 to 28 days or more, compared with protein production and product quality in cultures employing no temperature shift or, at most, one temperature shift.

In another of its aspects, the present invention provides cell culture methods comprising greater than two or three temperature shifts as described above. In such multi-step temperature shift runs, cells are cultured essentially as described for a three step culturing period, and additional downward temperature shifts are performed until the end of the culture period. For example, a fourth downward temperature shift, i.e., temperature lowering, can be carried out following the third temperature shift culture period, in which the cell culture temperature is further shifted from about 30° C., to about 28° C. or 29° C., preferably about 29° C., on or about days 15-19, preferably, day 18, from the start of the culture. Additional temperature shifts can be included in the cell culturing method, wherein the cells are maintained at a lower temperature, e.g., <29° C., to further extend protein production until the end of the run, preferably for longer than 28-30 days. In all cases, the protein produced by the cells at the end of the culturing period is typically recovered, e.g., isolated and/or substantially purified, as desired, employing techniques routinely practiced in the art as described herein. In addition, sialic acid content is assessed by conventional methods.

In one particular aspect, the present invention provides a process (or method) in which the final titer of product is enhanced, and the sialic acid content of the produced glycoprotein is higher, by the use of a two- or more-step temperature shift process. In accordance with this particular aspect, the combination of two or more timed temperature shifts sustains a high cell viability of the culture, thereby enabling an extended production phase during which the titer of product, preferably recombinant product, is increased and the product quality, as characterized by sialic acid content, is maintained at high level. Such a two- or more-step temperature shift can minimize the prevailing trade-off between protein titer and sialic acid content in the production of product during the cell culture process. Thus, the temperature shifts provide a positive effect on enhancing an important performance parameter of the culturing process, i.e., the mathematical product of "end (i.e., final) titer"דend (i.e., final) sialic acid" ("end titer×end sialic acid").

Accordingly, in another particular aspect, for a two-step culturing method as newly described herein, cells are maintained in culture from day 0 to on or about day 6 at a temperature of 37° C., or near 37° C.; on or about day 6, the temperature of the cell culture is lowered to 34° C., or near 34° C.; and on or about day 10-14, the temperature is again lowered to 32° C., or near 32° C. In one embodiment of such a two-step temperature shift method, the production phase is extended beyond about day 14 and continues to the end of the culture run, e.g., until about day 21, or to about day 28 to 30, or longer, during which time the cells are maintained in culture at the lower temperature of 32° C., or near 32° C. Protein product can be recovered at the end of the extended production phase as further described herein.

It is yet another aspect of the present invention to provide a method for increasing the viability of cells in culture by subjecting the cells to two or more shifts in temperature during the culture run. A condition, such as two or more shifts in temperature, causes increased cell viability if cell viability in the culture is higher for a period of time in the presence of the condition than in the absence of the condition. According to this aspect, the two or more temperature shift cell culturing methods as described allow cells to remain viable for increased time periods, such as beyond the standard production period. As discussed herein, a beneficial consequence of increased cell viability of the cultured cells can be that larger quantities of product (of high quality) are produced at the end of the culturing period, under conditions that are conducive to the maintenance of viable cells.

Another aspect of this invention is that increased cell viability resulting from the practice of the two or more temperature shift cell culturing methods correlates with a decreased amount of cell debris and released contents of dead or dying cells over time in the culture. The presence of cell debris and the contents of dead cells in the culture can negatively impact on the ability to isolate and/or purify the protein product at the end of the culturing run. By keeping cells viable for a longer period of time in culture, there is thus a concomitant reduction in the contamination of the culture medium by cell proteins and enzymes, e.g., cellular proteases and sialidases, that can cause degradation and ultimate reduction in quality of the desired glycoprotein produced by the cells.

Another aspect of this invention concerns the delayed addition of polyanionic compound to the cell culture. Delayed addition of polyanionic compound achieves increased cell viability. Polyanionic compound preferably is dextran sulfate. Polyanionic compound is added to the culture at a time after innoculation.

In one aspect of this invention, polyanionic compound is added to a culture at a time after innoculation that is before the beginning of the initial death phase, or is during the initial growth phase, or is during the second half of the initial growth phase, or is on or about the end of the initial growth phase. In accordance with this aspect of the invention, the growth phase is extended and/or the onset of the death phase is delayed for a period of time, such as several days. Additionally, once the death phase has begun, the death rate is greatly reduced.

In another aspect of this invention, polyanionic compound is added to a culture during the initial death phase. In accordance with this aspect of the invention, cell death is arrested for a period of time, such as several days.

In another preferred aspect of this invention and as further described herein, the newly developed cell culture processes, both those involving two or more temperature shifts and those involving the delayed addition of a polyanionic compound, are especially suitable for the production of soluble cytotoxic T-lymphocyte antigen-4 (CTLA4) molecules and soluble CTLA4 mutant molecule such as cytotoxic T-lymphocyte antigen-4 immunoglobulin (CTLA4Ig) and L104EA29YIg, by host cells genetically engineered to express and produce these proteins. (See Examples 1 through 11). Preferred embodiments of the present invention encompass the culturing of cells producing CTLA4Ig and L104EA29YIg using multiple temperature shifts during the culturing run to achieve large amounts of high quality CTLA4Ig and L104EA29YIg products, as determined by sialic acid measurement of the final products. Preferred embodiments of the present invention encompass the culturing of cells producing CTLA4Ig and L104EA29YIg, using the delayed addition of polyanionic compound.

Further aspects, features and advantages of the present invention will be appreciated upon a reading of the detailed description of the invention and a consideration of the drawings/figures.

DESCRIPTION OF THE DRAWINGS/FIGURES

FIG. 1 shows the impact of different temperature shift profiles on cell viability for cells cultured at a 5 liter (5 L) reactor scale. These results were obtained from the experiments described in Example 3 herein. Comparison is made among culturing methods involving no temperature shift ("no T-shift"), a single temperature shift ("single T-shift") and two downward temperature shifts ("double T-shift").

FIG. 2 shows the impact of different temperature shift profiles on cell viability for cells cultured at a 50 liter (50 L) reactor scale. These results were obtained from the experiments described in Example 3 herein. Comparison is made between culturing methods involving three downward temperature shifts ("triple T-shift") and two downward temperature shifts ("double T-shift").

FIG. 3 depicts a nucleotide sequence (SEQ ID NO:1) and encoded amino acid sequence (SEQ ID NO:2) of a CTLA4Ig having a signal peptide, a wild type amino acid sequence of the extracellular domain of CTLA4 starting at methionine at position +1 to aspartic acid at position +124, or starting at alanine at position −1 to aspartic acid at position +124, and an Ig region.

FIG. 4 depicts a nucleotide sequence (SEQ ID NO:3) and encoded amino acid sequence (SEQ ID NO:4) of a CTLA4 mutant molecule (L104EA29YIg) having a signal peptide, a mutated extracellular domain of CTLA4 starting at methionine at position +1 and ending at aspartic acid at position +124, or starting at alanine at position −1 and ending at aspartic acid at position +124, and an Ig region.

FIG. 5 depicts the nucleic acid sequence (SEQ ID NO:5) and encoded complete amino acid sequence (SEQ ID NO:6) of human CTLA4 receptor (referred to as "wild type" CTLA4 herein) fused to the oncostatin M signal peptide (position −26 to −2). (U.S. Pat. Nos. 5,434,131 and 5,844,095).

Figure 6:
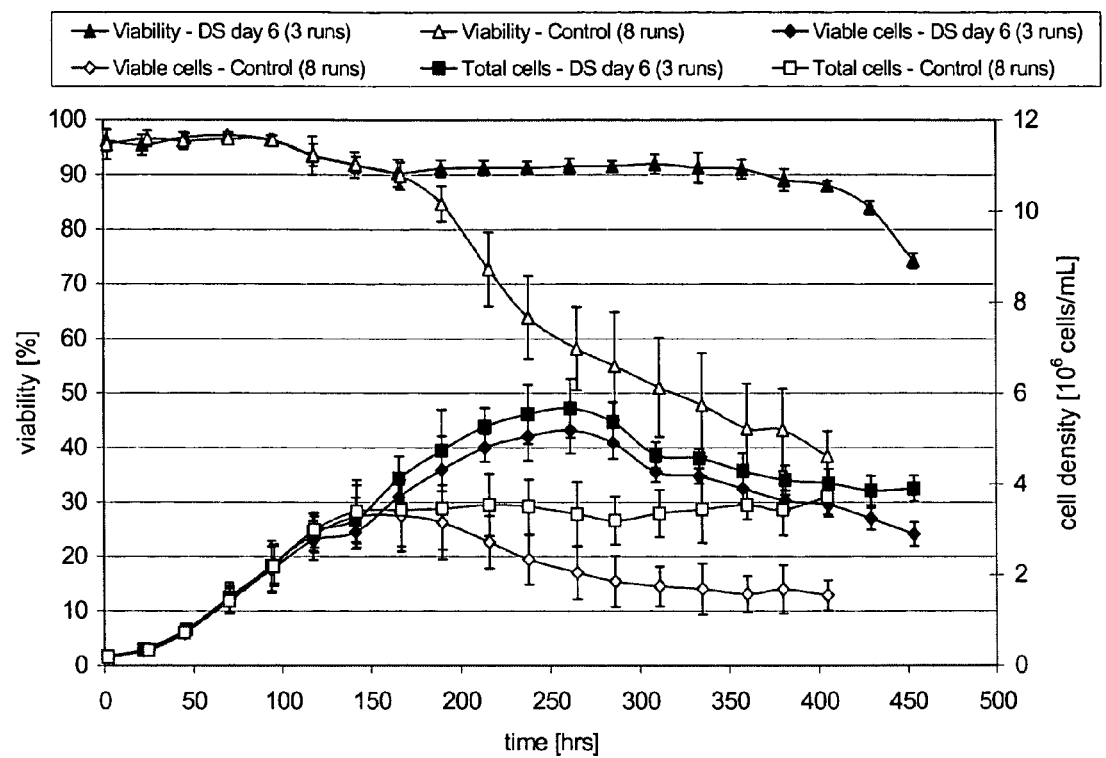

FIG. 6 shows the impact of delayed addition of dextran sulfate on viable cell density, total cell density, and viability in a culture in which dextran sulfate was added at the end of the initial growth phase. These results were obtained from the experiments described in Example 6 herein. Comparison is made between cultures in which dextran sulfate was added at the end of the initial growth phase, and cultures in which no dextran sulfate was added. Average values are plotted; error bars represent standard deviation.

Figure 7:
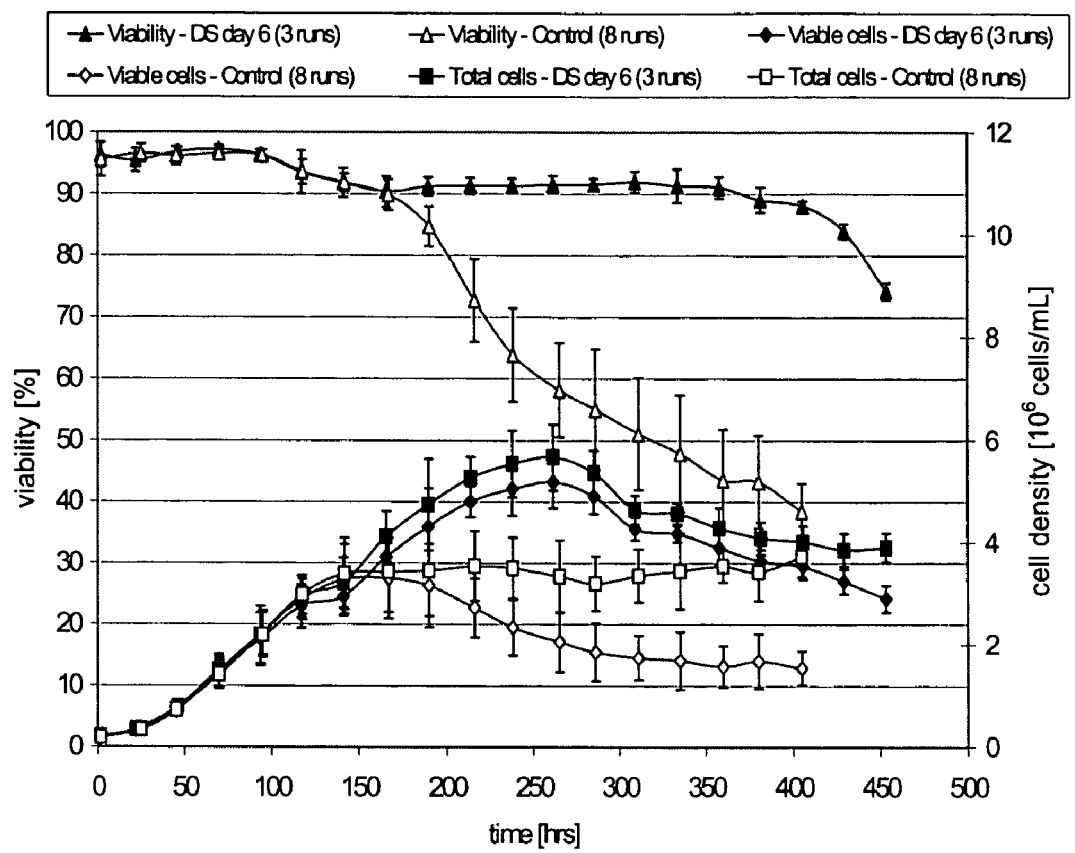

FIG. 7 shows the impact of delayed addition of dextran sulfate on death rate. It is a logarithmic representation of the viable cell densities as a function of time. These results were obtained from the experiments described in Example 6 herein. Comparison is made between cultures in which dextran sulfate was added at the end of the initial growth phase, and cultures in which no dextran sulfate was added. Average values are plotted. Error bars represent standard deviation.

Figure 8:
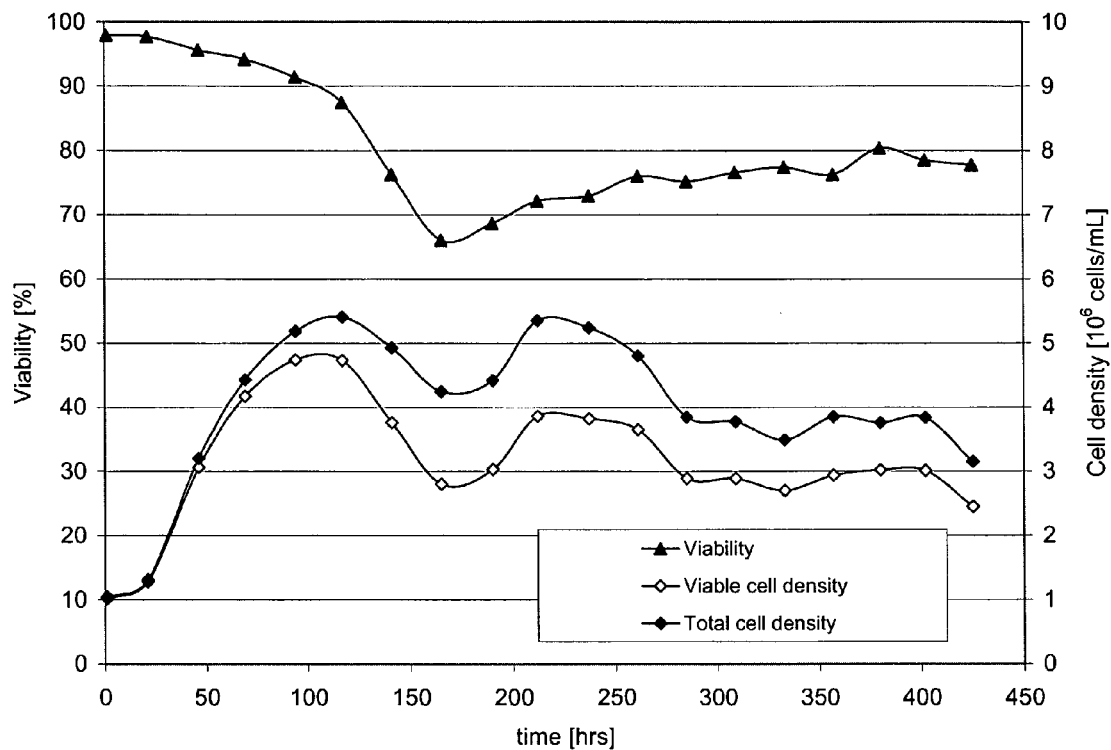

FIG. 8 shows the impact of delayed addition of dextran sulfate on viable cell density, total cell density, and viability in a culture in which dextran sulfate was added during the initial death phase. These results were obtained from the experiments described in Example 7 herein. Comparison is made between a culture in which dextran sulfate was added during the initial death phase, and a culture in which no dextran sulfate was added.

Figure 9:
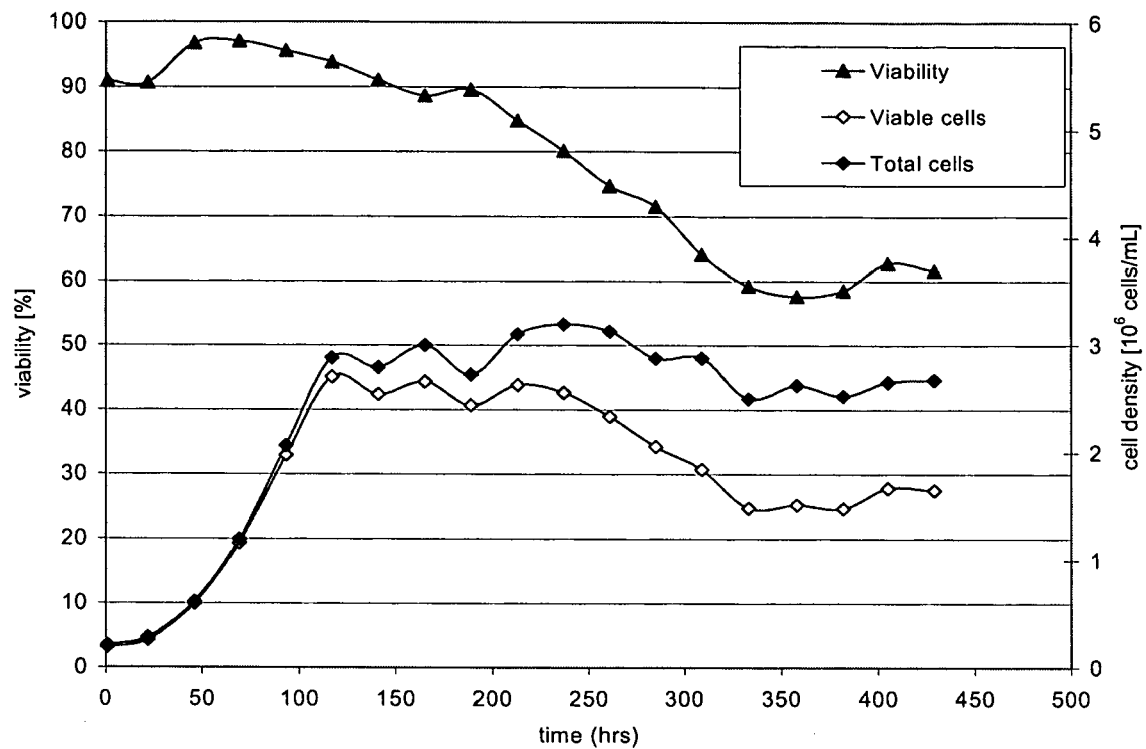

FIG. 9 shows the impact of delayed addition of dextran sulfate on viable cell density, total cell density, and viability in a culture in which dextran sulfate was added during the initial death phase. These results were obtained from the experiments described in Example 8 herein. Comparison is made between a culture in which dextran sulfate was added during the initial death phase, and a culture in which no dextran sulfate was added.

Figure 10:
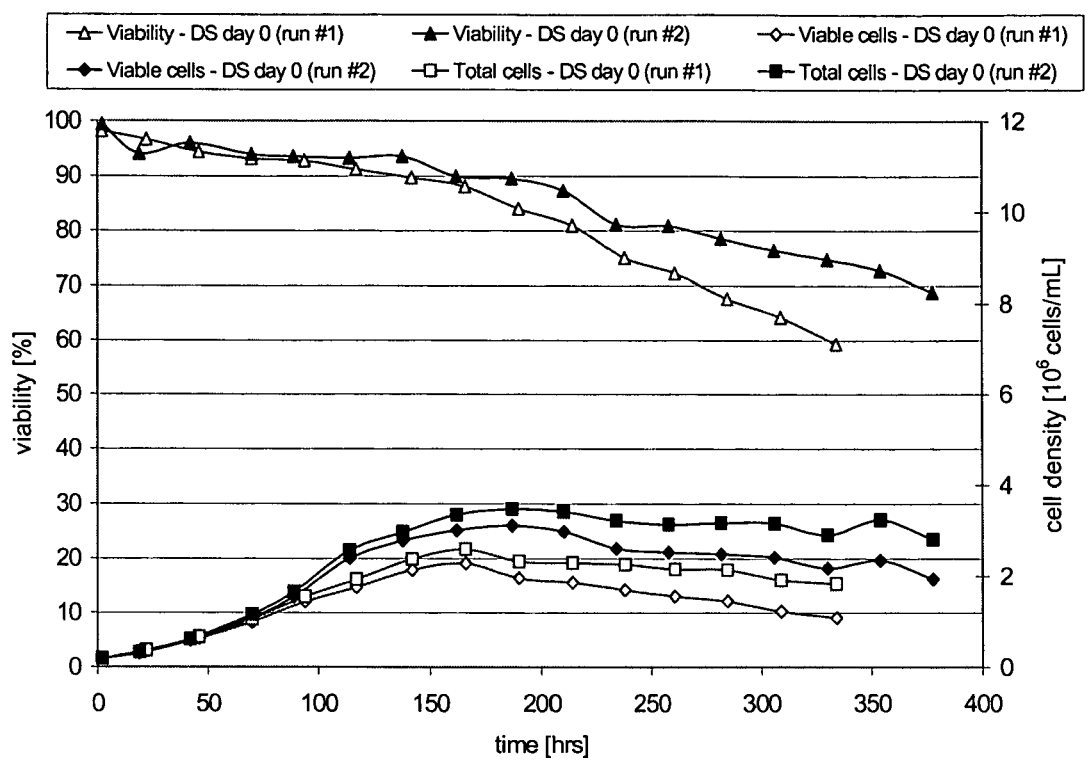

FIG. 10 shows viable cell density, total cell density, and viability in cultures in which dextran sulfate was added on day 0 of the culture. These results were obtained from the experiments described in Example 9 herein.

Figure 11:
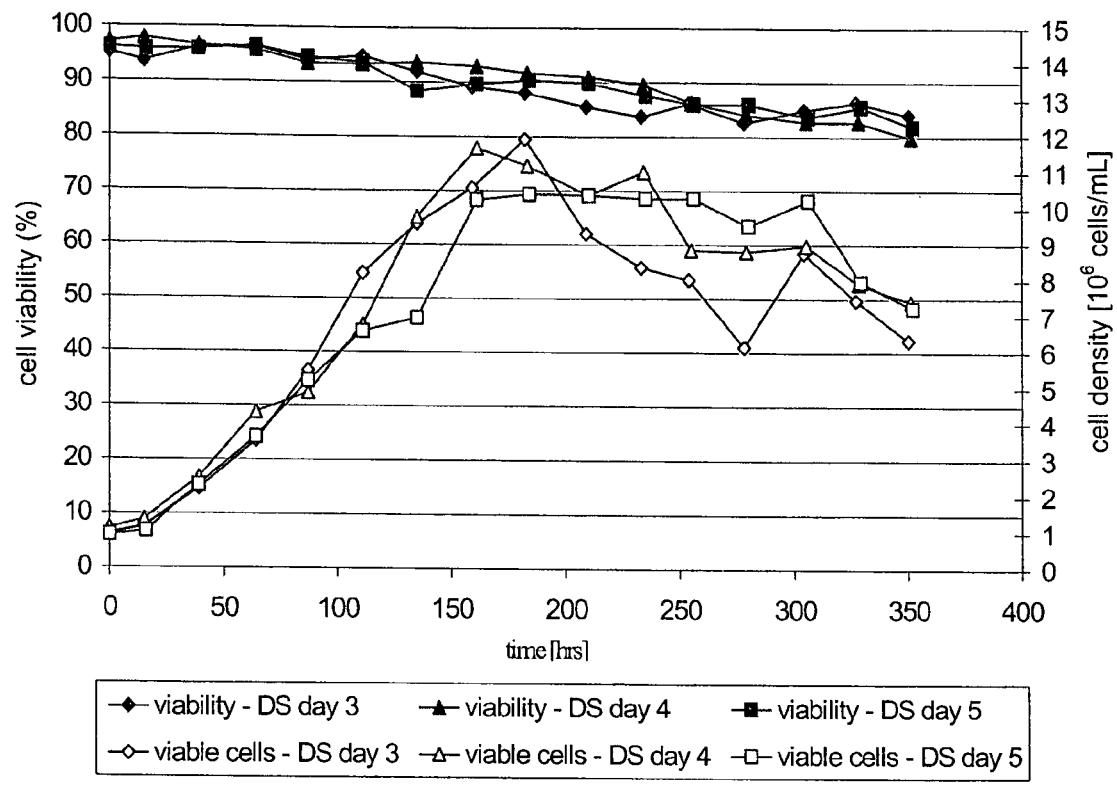

FIG. 11 shows viable cell density and viability in cultures in which dextran sulfate was added at three different times (day 3, day 4, and day 5) of the initial growth phase. These results were obtained from the experiments described in Example 10 herein.

Figure 12:
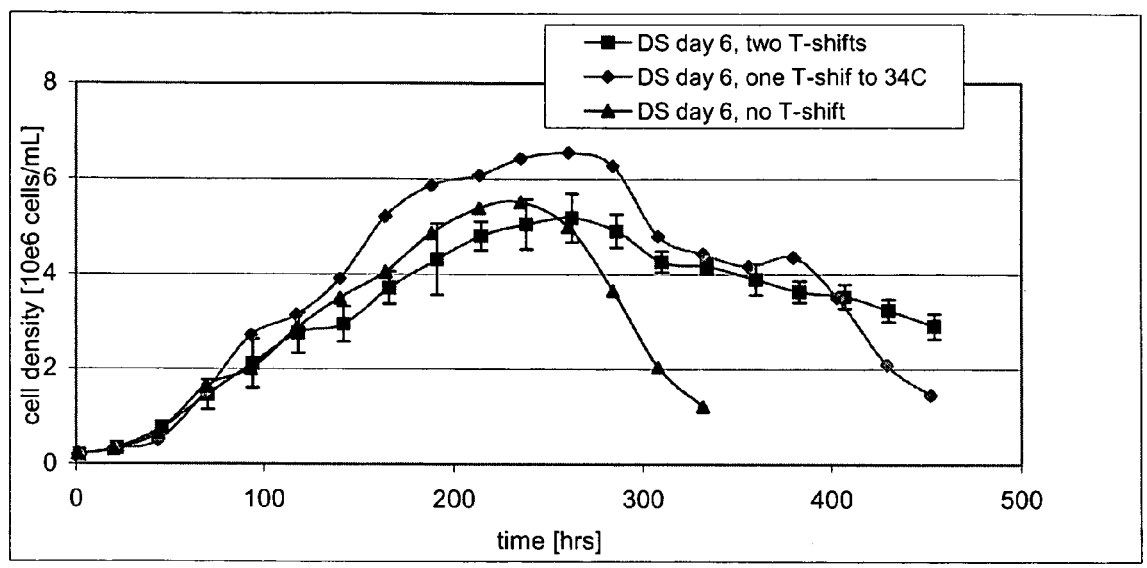

FIG. 12 shows the impact of different temperature shift profiles on viable cell density. These results were obtained from the experiments described in Example 11 herein. Comparison is made among culturing methods involving no temperature shift ("no T-shift"), a single temperature shift ("one T-shift") and two downward temperature shifts ("two T-shifts").

Figure 13:
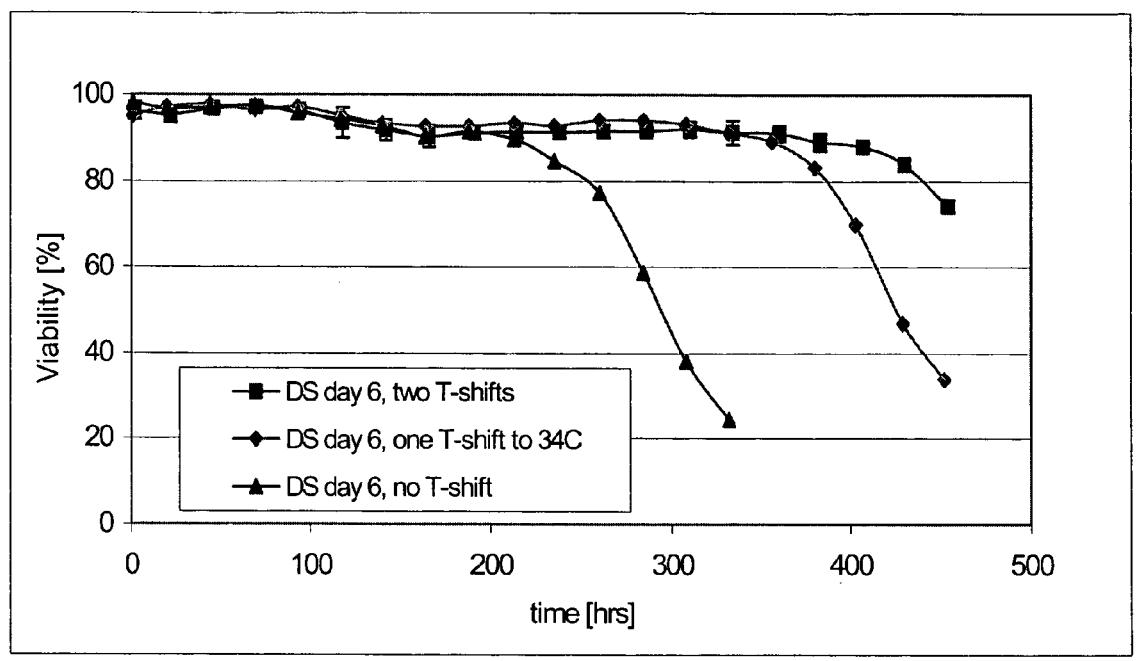

FIG. 13 shows the impact of different temperature shift profiles on viaability. These results were obtained from the experiments described in Example 11 herein. Comparison is made among culturing methods involving no temperature shift ("no T-shift"), a single temperature shift ("one T-shift") and two downward temperature shifts ("two T-shifts").

Figure 14:
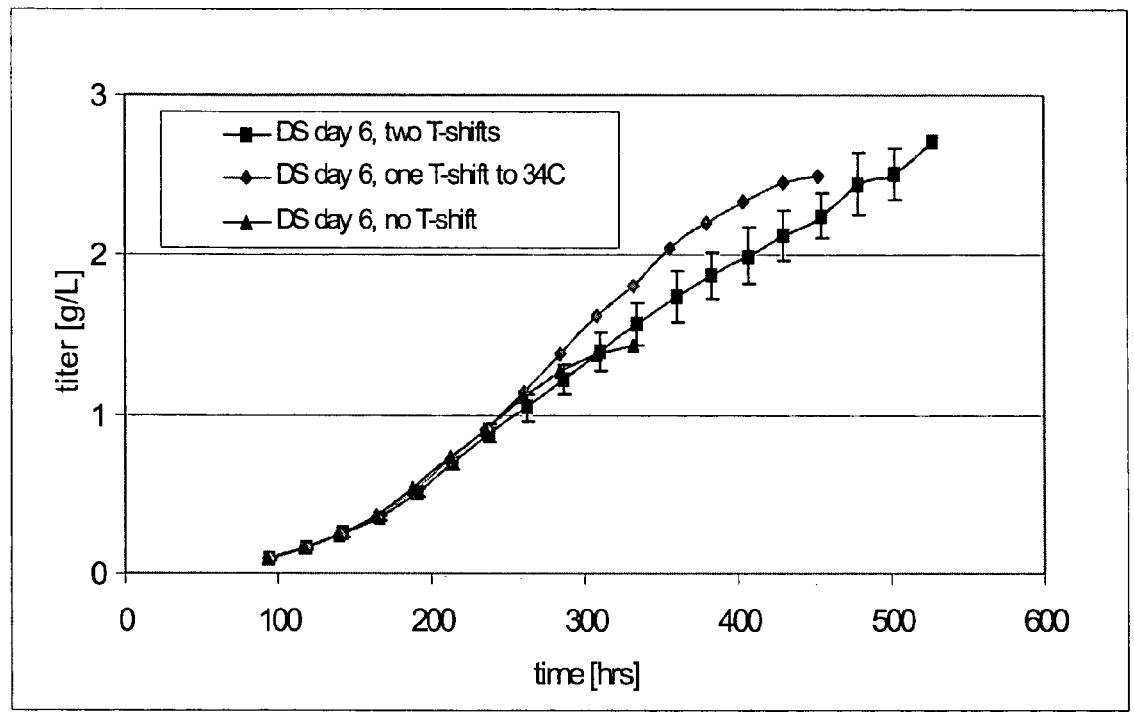

FIG. 14 shows the impact of different temperature shift profiles on titer. These results were obtained from the experiments described in Example 11 herein. Comparison is made among culturing methods involving no temperature shift ("no T-shift"), a single temperature shift ("one T-shift") and two downward temperature shifts ("two T-shifts").

DETAILED DESCRIPTION OF THE INVENTION

The present invention describes new processes for the production of proteins, preferably recombinant protein products, more preferably glycoprotein products, in mammalian or animal cell culture. These processes achieve increased cell viability.

Cell Culturing Processes Involving Two or More Temperature Shifts

The cell culturing processes according to this invention involving two or more temperature shifts achieve increased cell viability and can achieve an enhanced final titer or concentration of product produced by cells in culture. In addition, the sialic acid content of the glycoprotein produced by the cultured cells can be high, thus indicating a high quality of the protein product that is produced during the culturing period.

More specifically in accordance with this invention, two or more temperature shifts during the cell culturing run maintain and sustain a high cell viability of the cells in the culture, eg. achieve increased cell viability, and can provide a high quantity and quality of produced product throughout the culture run. Also, in accordance with the invention, the two or more temperature shifts can advantageously allow for an extension of the production phase of the culture. During the extended production phase, cell viability is maintained; the titer of the desired product is increased; and the product quality, as characterized by sialic acid content, is maintained at a high level.

In accordance with this invention, two or more temperature shifts, preferably downward temperature shifts, during the cell culturing period can allow for a high quantity and quality of protein product to be produced at the end of the culturing period, compared with culturing methods involving no temperature shift, or only one temperature shift. Illustratively, as shown in Example 3, a culturing process with two or three temperature shifts in accordance with the present invention yields an increase in the quantity of protein (e.g., end titer) compared with no temperature shift or only one temperature shift, regardless of the total length of the culture run. In addition, the processes and methods of the present invention are particularly suited to cells grown and maintained as fed-batch cultures, as further described herein.

Because the two or more temperature shifts of the culturing methods also maintain and sustain a high viability of the cells in culture, the culturing processes can extend the production phase for protein. In particular, during the cell culturing methods comprising an extended production phase, cell viability remains high, the titer of the desired product is increased, and the product quality, as characterized by a measurable sialic acid content, is also maintained at a high level. As newly provided by this invention, the cell culture methods comprise a production phase that is extended beyond the production that is yielded by culturing procedures involving no temperature shifts or, at most, only one temperature shift.

Cell Culturing Methods Involving Multiple Temperature Shifts

In embodiments of the present invention, timed multi-step temperature shifts are used in the culturing of mammalian cells to produce a desired protein product, particularly, a glycoprotein product. More preferably, the cells in culture produce a recombinantly produced protein, polypeptide or peptide product. However, in some cases, the cells may actively produce, or overproduce, an endogenous or natural product which can be harvested or recovered following the practice of the methods of the present invention. As described herein, two or more temperature shifts, preferably controlled, downward temperature shifts, carried out at appropriately timed intervals during the culturing period, can be used in the processes of this invention to achieve a high protein yield with a concomitant high sialic acid content.

In accordance with the cell culturing methods and processes of this invention (also referred to as production or fermentation runs), cells cultured in conjunction with two or more temperature shifts during a culturing run can produce a high quantity and quality of product during the run, as measured by end titer and sialic acid content at the end of the run. The high quantity and quality of protein production associated with the methods of this invention are obtained relative to methods in which no temperature shift, or at most, one temperature shift is used, regardless of whether a culture run is carried out for a total run time of about 10-14 days or for more than 14 days. Moreover, as a result of the two or more temperature shifts during the culturing process, cells can be maintained in culture for a period of time that essentially extends the standard or initial production phase. A standard or initial production phase is typically about 6 to 14 days. Increased production of high quality protein, as well as sustained cell viability, are achieved during the extended production phase of the present culturing methods involving two or more temperature shifts.

Also according to the present culturing methods, cells can be cultured for a total run period of greater than about 10 days, greater than about 14 days, greater than about 21 days, or greater than about 28 days, preferably, about 14 to 30 days, or more. For example, in a culture run of this invention that comprises two or more temperature shifts, the length of the entire run can last from as short as just after the second (or last) temperature shift (for example, about 14 days) to as long as about 21 to 30 days or more, preferably about 28 days or more.

In an embodiment of the present invention, the extended production phase is associated with the multiple temperature shifts that comprise the cell culturing methods of this invention. According to the new cell culture methods of this invention, the combination of a second, third, or further temperature shift with a first temperature shift not only allows the cell cultures to produce high quantity and quality of product throughout the duration of the culture run, but also allows the culture to sustain a high cell viability throughout the run and/or throughout an extended production phase until the end of the culture run. During the culture run, including the extended production phase, the titer of the protein product is increased and product quality, as characterized by sialic acid content, remains high.

More particularly, in one of its specific embodiments, the present invention embraces cell culture methods that extend the initial production phase of protein production by cultured cells (i.e., the standard production phase that encompasses about days 6-14 is extended). By employing two or more temperature shifts in the culture run in accordance with this invention, an extended production phase at about days 14-21 was achieved. With three (or more) temperature shifts in the culture run, the culture run was further extended to about 21-28 or 30 days, or more, with concomitantly higher yields of protein product of high quality (e.g., high sialic acid content), (e.g., Example 3).

In another particular embodiment of this invention, the cell culturing (or fermentation) process encompasses a two step downward temperature shift in which cells are maintained at three different temperatures during the total culturing run. In this embodiment, the total cell culturing period lasts greater than about 10 days, more specifically, about 14 to 28 days or more, i.e., about two to three weeks or more, prior to obtaining the end protein product (and measuring sialic acid content). For example, in such a two step method, cells are maintained at a first temperature of about 36° C. to 38° C., preferably, 37° C., or near 37° C., for an initial culturing period of from day 0 to about day 6. Thereafter, from about day 5 to day 7, preferably day 6, to about day 10, the culture temperature is maintained at a second temperature of about 33° C. to 35° C., preferably, 34° C., or near 34° C. Following cell culture at or near 34° C., the temperature is shifted a second time (secondary T-shift) to a third temperature of about 31° C. to 33° C., preferably, 32° C., or near 32° C. The secondary T-shift occurs on or about day 6 to about day 14, preferably from about day 10 to about day 14, more preferably, on or about day 10, which in various embodiments may be during the standard production phase, during the growth phase, or during the death phase. Preferably there are approximately four day increments between the first and the second temperature shifts, more preferably four day increments. The cells are maintained at a temperature of 32° C., or near 32° C. until the end of the total culture run, e.g., for longer than about day 10, more specifically, to about days 12-18, or to about days 14-18, or to about days 14-28 or 30, or more. At the end of the culturing process, the protein product is typically isolated and/or purified, for example, from the culture supernatant, if the product is secreted into the culture medium.

Alternatively in the multiple temperature shift culturing methods of this invention, the temperature may be first lowered based on the phase of the culture. The first temperature shift preferably occurs before the start of the death phase. In one embodiment, the temperature is first lowered concurrently with the slowing of cell growth. For example, the temperature is shifted from 37° C., or near 37° C., to 34° C., or near 34° C., when the cells are no longer in their exponential growth phase and the culture is in the stationary phase, for example, on or about day 6 of culture. At this time, the viable cell concentration has reached a suitable cell density for protein production, preferably enhanced protein production, for example, about $2-12\times10^6$ cells/mL, such as $2-9\times10^6$ cells/mL, $3-7\times10^6$ cells/mL, $4-5\times10^6$ cells/mL, $3-4\times10^6$ cells/mL, $2-4\times10^6$ cells/mL, $4-6\times10^6$ cells/mL, $6-8\times1\ 06$ cells/mL, $8-10\times10^6$ cells/mL, or $10-12\times10^6$ cells/mL. Without wishing to be bound by theory, it is possible that the slowing of cell growth correlates with the depletion of nutrients and/or particular components of the cell culture medium, e.g., a nitrogen limitation in the medium.

In another embodiment, the first shift in temperature occurs during the growth phase, for example when the viable cell concentration is about $2-12\times10^6$ cells/mL, such as $2-9\times10^6$ cells/mL, $3-7\times10^6$ cells/mL, $4-5\times10^6$ cells/mL, $3-4\times10^6$ cells/mL, $2-4\times10^6$ cells/mL, $4-6\times10^6$ cells/mL, $6-8\times10^6$ cells/mL, $8-10\times10^6$ cells/mL, or $10-12\times10^6$ cells/mL.

In yet another embodiment embracing the two-step temperature shift culturing process, cells are cultured for a 14 day run in which the culture temperature is maintained at or near 37° C. from day 0 to day 6. From about day 6 to about day 10, the culture temperature is maintained at or near 34° C.; and from about day 10 to about day 14, the culture temperature is maintained at or near 32° C. As another embodiment, cells are cultured for about a 21 day period in which the culture temperature is maintained at or near 37° C. from day 0 to about day 6; from about day 6 to about day 10, the culture temperature is maintained at or near 34° C.; and from about day 10 to about day 21, the culture temperature is maintained at or near 32° C. As yet another embodiment, cells are cultured for about a 28 day period in which the culture temperature is maintained at or near 37° C. from day 0 to about day 6; from about day 6 to about day 10, the culture temperature is maintained at or near 34° C.; and from about day 10 to about day 28, the culture temperature is maintained at or near 32° C.

The present invention also encompasses embodiments in which the cell culturing methods comprise three or more temperature shifts. In one embodiment involving a three-step temperature shift culturing process, cells are initially cultured at a first temperature of about 36° C. to 38° C., preferably, at or near 37° C. for about 6 days; thereafter, the culture temperature is shifted and maintained at about 33° C. to 35° C., preferably, at or near 34° C. for a given time period; a second shift to a temperature of about 31° C. to 33° C., preferably, at or near 32° C. occurs thereafter. A third temperature shift to a temperature of about 29° C. to 31° C., preferably at or near 30° C., follows the culturing period at 32° C. or near 32° C.; the temperature is then held at or near 30° C. until the end of the run.

In other embodiments, further temperature shifts, preferably downward temperature shifts, can be performed following the third temperature shift of the culture method. For example, a fourth temperature shift can follow the third shift on or about day 15-20, preferably at about day 18 from the start of the culture. The fourth downward shift maintains the culture temperature at or near 28° C. to 29° C., preferably, about 29° C., and increases the culture run to greater than about 28 days, e.g., to about 28-32 days or more, at which time product is obtained.

As in the two-step temperature shift culturing run procedure according to this invention, the first shift in temperature in the multiple temperature shift processes of the present invention can occur when the cells have essentially stopped growing and have become stationary or approximately so. Illustratively, the temperature shift is performed when the viable cell concentration is about $2-12\times10^6$ cells/mL, such as $2-9\times10^6$ cells/mL, $3-7\times10^6$ cells/mL, $4-5\times10^6$ cells/mL, $3-4\times10^6$ cells/mL, $2-4\times10^6$ cells/mL, $4-6\times10^6$ cells/mL, $6-8\times10^6$ cells/mL, $8-10\times10^6$ cells/mL, or $10-12\times10^6$ cells/mL. Alternatively, the first shift in temperature occurs during the growth phase, for example when the viable cell concentration is about $2-12\times10^6$ cells/mL, such as $2-9\times10^6$ cells/mL, $3-7\times10^6$ cells/mL, $4-5\times10^6$ cells/mL, $3-4\times10^6$ cells/mL, $2-4\times10^6$ cells/mL, $4-6\times10^6$ cells/mL, $6-8\times10^6$ cells/mL, $8-10\times10^6$ cells/mL, or $10-12\times10^6$ cells/mL. In another preferred embodiment, the multi-step cell culturing process comprises three timed and controlled temperature shifts during a culturing period of about three to four weeks, e.g., 21-30 days or more, preferably 28 days or more, providing extended production of product by the cells in culture. To illustrate, the three-step temperature shift process comprises an initial culturing period from 0 to about 6 days, preferably 6 days, during which time cells are cultured at a temperature of 37° C., or near 37° C. From about day 6 to about day 10, the cells are cultured at 34° C., or near 34° C. From about day 10 to about day 14, the culture temperature is maintained at 32° C., or near 32° C.; and from about day 14 onward, i.e., to about day 21 to day 30 or more, or to the end of the run, the culture temperature is maintained at 30° C., or near 30° C. Accordingly, in the three-step temperature shift culture process of this invention, the production phase may also be extended to yield higher end titer of protein and higher cell viability for a time period longer than about 14 days, in contrast to the standard production phase of about 6 to 14 days with only one or no temperature shift(s). Advantageously, the production phase and cell viability may be further extended by the three-step T-shift method, i.e., to about three weeks or more, with accompanying high quality of product, as measured by sialic acid content.

In various embodiments of the present invention, the second temperature shift to 32° C., or near 32° C. allows higher quantity and quality of protein at the end of the culture run, and is also associated with extended protein production during a run that can last for more than about two weeks. The two or more shifts in temperature permit the culture to stabilize a slow decline in cell viability which can occur during the previous two weeks in culture. Yet another temperature shift from 32° C., or near 32° C., to 30° C., or near 30° C., timed at about two weeks, or thereabouts, provides a further extension of the production phase, thus prolonging the production phase of the cell culture to the end of the culturing run, e.g., to about day 21 to day 30 or more, while maintaining cell viability without sacrificing the quality (as determined by measurement of sialylation) of the product produced. (See Example 3, Tables 2 and 3). Additional temperature shifts can extend cell production beyond that of the two and three temperature shift runs.

In other embodiments, the present invention is directed to (i) a cell culturing process, (ii) a method of increasing protein production, preferably associated with increased cell viability, (iii) a method of enhancing sialylation of a protein product, (iv) a method of enhancing cell viability, or (v) a method of extending protein production, involving two or more temperature shifts, comprising: culturing host cells which express a protein of interest at a temperature at or near 37° C. under conditions and for a time period that allow for cell growth; lowering the temperature of the cell culture and culturing the cells at a second temperature at or near 34° C. when the culture is in the stationary phase; again lowering the temperature of the cell culture and culturing the cells at a third temperature at or near 32° C. at a time during the standard production phase of about day 6 to day 14, e.g., on or about ten days from the start of the culture, until the end of culturing period. As has been noted herein, the culturing period can comprise a total run time of greater than 10 days, greater than 14 days, greater than 21 days, or greater than 28-30 days. Following culture of the cells at 32° C., i.e., at the end of the culture run, the produced protein product, preferably a glycoprotein, is obtained.

In other embodiments, the present invention is directed to (i) a cell culturing process, (ii) a method of increasing protein production, preferably associated with increased cell viability, (iii) a method of enhancing sialylation of a protein product, (iv) a method of enhancing cell viability, or (v) a method of extending protein production, involving two or more temperature shifts, comprising: culturing host cells which express a protein of interest at a temperature at or near 37° C. under conditions and for a time period that allow for cell growth; lowering the temperature of the cell culture and culturing the cells at a second temperature at or near 34° C. starting about day 5 to day 7; again lowering the temperature of the cell culture and culturing the cells at a third temperature at or near 32° C. starting about day 6 to day 14, e.g., on or about ten days from the start of the culture, until the end of culturing period. As has been noted herein, the culturing period can comprise a total run time of greater than 10 days, greater than 14 days, greater than 21 days, or greater than 28-30 days. Following culture of the cells at 32° C., i.e., at the end of the culture run, the produced protein product, preferably a glycoprotein, is obtained.

In another of its embodiments, the present invention provides culture methods further comprising another temperature downshift from at or near 32° C. to at or near 30° C. on or about 14 days from the start of the culture until the end of the culturing process, thereby extending the culture period well beyond a standard production phase. To further extend protein production during the culturing process, as well as cell viability, the method can comprise a fourth temperature downshift from at or near 30° C. to at or near 29° C. on or about 15 to 19 days, preferably 18 days, from the start of the culture until the end of the culturing process.

The temperature shifts of this invention are typically on or about day 6 of the culture period, which may be during or after the growth phase of the culture, and thereafter at approximately 4 day increments, preferably 4 day increments. In some embodiments, the timing of the shifts in temperature may approximate the beginning (e.g., on or about day 6), the middle (e.g., on or about day 10) and the end (e.g., on or about day 14) of the standard production phase. In the culturing processes or methods according to this invention in which the final titer and sialic acid content of a produced glycoprotein is enhanced by the use of a multi-step (e.g., two step, three step or more) temperature shift profile, the combination of at least two, timed temperature shifts allows a total culture run to be carried out for greater than 10 days, greater than 14 days, greater than 21 days, or greater than 28 or more days, without sacrificing end titer and sialylation of the product In accordance with the culturing processes of this invention, the two or more temperature shifts sustain a high cell viability of the culture and can allow more high titer and high quality protein to be produced in a culture run compared with a run that occurs for the same period of time, but does not include two or more temperature shifts. Also, the two or more temperature shifts can allow the production phase of the culture to extend beyond that of a standard production phase and/or beyond the production of a culture having no temperature shift, or at most, one temperature shift. Such multi-step temperature shifts, such as the two- or more-step temperature shift, can minimize the prevailing trade-off between titer ("end titer") and sialic acid content in the production of protein product in the cell culture process. Thus, the temperature shifts provide a positive effect on enhancing the mathematical product of "end titer×end sialic acid", which improves on the protein production process.

Additional Embodiments in Accordance with the Invention of Cell Culture Processes Involving Two or More Temperature Shifts In one embodiment, the present invention encompasses a cell culturing process comprising culturing host cells which express a protein of interest at a first temperature at or near 37° C. under conditions and for a time that allow for cell growth. Following the cell growth period, the cells are cultured at a second temperature at or near 34° C. when cell growth has slowed and becomes approximately stationary. Thereafter, the cells are cultured at a third temperature at or near 32° C. during the standard production phase of culture, i.e., on or about day 6 to on or about day 14. At the end of the culturing process, the produced protein product can be obtained.

In accordance with a preferred embodiment of this invention, the cells are cultured in a batch-fed process comprising several phases, namely, a growth phase, during which cells are cultured at a first temperature at or near 37° C.; an initial or standard production phase, during which cells are cultured at a second temperature at or near 34° C. and at a third temperature at or near 32° C. so as to provide an extended protein production phase, which can include a fourth temperature at or near 30° C., and optionally thereafter, additional lower temperatures, such as at or near 29° C. In the cases of the two or more-step temperature shift runs of this invention, extension of protein production is related to the two or more downward shifts in temperature. As described herein, an extended production phase comprises a successive lowering of the temperature of the culture at different intervals two or more times following the first temperature switch from at or near 37° C. to at or near 34° C. Relative to no temperature shifting, or only one temperature shift, protein production is increased and high product quality (as measured by sialic acid content of the final product) is attained by the practice of these methods involving two or more downward temperature shifts during the culturing run.

During the growth phase of cell culture, e.g., from day 0 to about day 6, the cell density in the culture increases as the cells are typically rapidly dividing in this period of exponential cell growth, or log phase. In the non-growth associated cell culturing and protein production methods present in some aspects of this invention, no significant amounts of protein product are produced during the growth phase in which cell growth is essentially maximized under appropriate growth conditions. Thus, as a consequence of nutrient limitations in the culture, the cells typically enter a stationary phase on about days 4 to 6, in which rapid cell growth plateaus and/or declines. In these culturing methods, the protein production phase begins when cell growth has essentially ended (e.g., at about day 6 to about day 10). (Example 3).

In accordance with the culturing method of one embodiment, when the cells reach stationary phase on about day 6, the temperature is shifted downward from at or near 37° C. to at or near 34° C. Thereafter, at a time that is near the midpoint between the first temperature shift (about day 6) and the onset of the extended production phase (about day 14), the temperature of the culture is again lowered from at or near 34° C. to at or near 32° C. The second temperature shift allows the culture to stabilize cell viability, which typically slowly declines through about day 14; thereafter, an extension of the production phase begins (at about day 14 to about day 21 to day 30 or longer, preferably to about day 21 to day 28 or longer). As has been described above, other temperature shifts, e.g., a third, fourth, or more, can be employed during the extended production phase of the culture run.

Cell Culturing Methods Involving Delayed Addition of a Polyanionic Compound

In accordance with the present invention, a cell culture process involving the delayed addition of polyanionic compound is provided. The process comprises adding polyanionic compound to a cell culture at a time after innoculation. The delayed addition of polyanionic compound achieves increased cell viability as compared to that observed in the absence of addition of polyanionic compound, or as compared to that observed when polyanionic compound is added at inoculation.

Thus, in one embodiment, the invention is directed to a cell culturing process comprising: culturing host cells which express a protein of interest; and adding polyanionic compound to the cell culture at a time after innoculation.

It has been found (see Example 6) that when carrying the present invention the percent cell viability of the cell culture is increased. Percent cell viability, also known as cell viability, is the percent of viable cells in the total number of cells. A condition, such as delayed addition of polyanionic compound, causes increased cell viability if cell viability in the culture is higher for a period of time in the presence of the condition than in the absence of the condition.

Thus, in other embodiments, the invention is directed to (1) a cell culturing process, and (2) a method of increasing the cell viability in a culture comprising: culturing host cells which express a protein of interest; and adding polyanionic compound to the cell culture at a time after innoculation; wherein the cell viability of the cell culture is increased.

Polyanionic compounds include, but are not limited to, dextran sulfate (available from Sigma-Aldrich, St. Louis, Mo.), heparin (available from Sigma-Aldrich), heparan sulfate (available from Sigma-Aldrich), mannan sulfate, chondroitin sulfate (available from Sigma-Aldrich), dermatan sulfate (available from Sigma-Aldrich), keratan sulfate (available from Sigma-Aldrich), hyaluronate (available from Sigma-Aldrich), poly(vinyl sulfate) (available from Sigma-Aldrich), kappa-carrageenan (available from Sigma-Aldrich), and suramin (available from Sigma-Aldrich). The compounds are readily available from the listed sources, or readily obtainable through means known to one of skill in the art. These compounds are frequently available in the form of a salt, including but not limited to sodium salt, but may also be used in non-salt forms. A polyanionic compound includes all forms thereof, including but not limited to salt forms, such as sodium salts.

Preferred polyanionic compounds are poysulfated compounds, including but not limited to: dextran sulfate, heparin, heparan sulfate, mannan sulfate, chondroitin sulfate, dermatan sulfate, keratan sulfate, poly(vinyl sulfate), kappa-carrageenan, and suramin. Most preferred is dextran sulfate. Dextran sulfate may have an average molecular weight of 5,000 to 500,000 Da. Preferred is dextran sulfate with a molecular weight of 5,000 Da.

In accordance with the invention, polyanionic compound is added at a time after innoculation, i.e. it is not present in the basal medium and not present at innoculation. Preferably, the polyanionic compound is added on day 1 of the culture or later. Innoculation takes place on day 0.

In accordance with the invention, polyanionic compound may be added to the cell culture one time, two times, three times, or any number of times during the specified time period (eg. at a time after innoculation). One or more polyanionic compounds may be used in conjunction. That is, any given single addition of a polyanionic compound may include the addition of one or more other polyanionic compounds. Similarly, if there is more than one addition of a polyanionic compound, different polyanionic compounds may be added at the different additions. Additional compounds and substances, including polyanionic compounds, may be added to the culture before, with or after the addition of polyanionic compound—either during or not during the specified time period. In a preferred embodiment, there is a single, i.e. one time, addition of polyanionic compound. In a preferred embodiment, one polyanionic compound is added.

In accordance with the invention, polyanionic compound may be added to the cell culture by any means. Means of adding polyanionic compound include, but are not limited to, dissolved in water, dissolved in culture medium, dissolved in feed medium, dissolved in a suitable medium, and in the form in which it is obtained. Preferably, polyanionic compound is added dissolved in water.

In accordance with the invention, polyanionic compound is added to bring the concentration in the culture to an appropriate level. As non-limiting examples, polyanionic compound is added to a concentration of 1-1000 mg/L, 1-200 mg/L, 1-100 mg/L, or 25-75 mg/L. Preferably polyanionic compound is added to a concentration of 25-200 mg/L or 25-100 mg/L, more preferably about 50-100 mg/L or 50-100 mg/L, more preferably about 50 mg/L or about 100 mg/L, most preferably 50 mg/L or 100 mg/L.

In accordance with the invention, the culture may be run for any length of time after addition of polyanionic compound. The culture run time may be determined by one of skill in the art, based on relevant factors such as the quantity and quality of recoverable protein, and the level of contaminating cellular species (e.g. proteins and DNA) in the supernatant resulting from cell lysis, which will complicate recovery of the protein of interest.

In particular embodiments of the cell culturing process and method of increasing cell viability of the invention, polyanionic compound is added at a time after innoculation that is before the beginning of the initial death phase. Preferably, polyanionic compound is added at a time after innoculation that is during the initial growth phase. More preferably, polyanionic compound is added during the second half the initial growth phase. More preferably, polyanionic compound is added on or about the end of the initial growth phase.

The initial growth phase refers to the growth phase that is observed in the absence of the specified addition of polyanionic compound. The initial death phase refers to the death phase that is observed in the absence of the specified addition of polyanionic compound.

The initial growth phase may end when the initial death phase begins, or there may be a stationary phase of any length between the initial growth phase and the initial death phase.

In a specific embodiment, in a cell culture in which the initial growth phase is from day 0 to day 6 and the initial death phase begins on day 7, in a particular embodiment polyanionic compound is added at a time after innoculation and before day 7, In a specific embodiment, polyanionic compound is added after innoculation and by day 6. In a specific embodiment, polyanionic compound is added between days 1 and 6. In another specific embodiment, polyanionic compound is added on day 4, 5 or 6. In other specific embodiments, polyanionic compound is added on about day 6, or on day 6.

It has been found (see Examples 6 and 10), that when polyanionic compound is added at a time after innoculation and before the beginning of the initial death phase, the growth phase may be extended beyond the initial growth phase. A growth phase that is extended beyond the initial growth phase has a longer duration than the initial growth phase, i.e. longer than the growth phase observed in the absence of addition of polyanionic compound. Preferably, during the extended growth phase a higher peak viable cell density is achieved than the peak viable cell density achieved during the initial growth phase.

Thus, in other embodiments, the invention is directed to (1) a cell culturing process, and (2) a process for extending the growth phase of a cell culture comprising: culturing host cells which express a protein of interest; and adding polyanionic compound to the cell culture at a time after innoculation that is before the beginning of the initial death phase; wherein the growth phase is extended. In particular embodiments, the invention is directed a (1) a cell culturing process, and (2) process for extending the growth phase of a cell culture comprising: culturing host cells which express a protein of interest; and adding polyanionic compound to the cell culture at a time after innoculation that is during the initial growth phase; wherein the growth phase is extended In more particular embodiments the invention is directed to (1) a cell culturing process, and (2) a process for extending the growth phase of a cell culture comprising: culturing host cells which express a protein of interest; and adding polyanionic compound to the cell culture during the second half of the initial growth phase; wherein the growth phase is extended. In other particular embodiments the invention is directed to (1) a cell culturing process, and (2) a process for extending the growth phase of a cell culture comprising: culturing host cells which express a protein of interest; and adding polyanionic compound to the cell culture on or about the end of the initial growth phase; wherein the growth phase is extended.

The growth phase may be extended for any period of time beyond the duration of the initial growth phase. By way of example only, the growth phase may be extended for 1-10 days, for 2-9 days, for 3-8 days, or for about 5 days. Preferably, the growth phase is extended for one or more days, more preferably for two or more days, more preferably for three or more days, most preferably for four or more days. For example, in Example 6 the growth phase is extended to day 11 where the initial growth phase is until day 6. Thus, in Example 6 the growth phase has been extended for 5 days beyond the duration of the initial growth phase. The extended growth phase may be succeeded by a death phase or by a stationary phase. Likewise, the initial growth phase may be succeeded by a death phase or by a stationary phase.

It has been found (see Examples 6 and 10), that when polyanionic compound is added at a time after innoculation and before the beginning of the initial death phase, the onset of the death phase may be delayed beyond the onset of the initial death phase, i.e. beyond the onset of the death phase observed in the absence of the addition of polyanionic compound. A death phase whose onset is delayed begins at a later time than the initial death phase.

Thus, in other embodiments, the invention is directed to (1) a cell culturing process, and (2) a process for delaying the death phase of a cell culture comprising: culturing host cells which express a protein of interest; and adding polyanionic compound to the cell culture at a time after innoculation that is before the beginning of the initial death phase; wherein the onset of the death phase is delayed. In more particular embodiments, the invention is directed to (1) a cell culturing process, and (2) a process for delaying the death phase of a cell culture comprising: culturing host cells which express a protein of interest; and adding polyanionic compound to the cell culture at a time after innoculation that is during the initial growth phase; wherein the onset of the death phase is delayed. In more particular embodiments the invention is directed to (1) a cell culturing process, and (2) a process for delaying the death phase of a cell culture comprising: culturing host cells which express a protein of interest; and adding polyanionic compound to the cell culture during the second half of the initial growth phase; wherein the onset of the initial death phase is delayed. In other particular embodiments the invention is directed to a process for delaying the death phase of a cell culture comprising: culturing host cells which express a protein of interest; and adding polyanionic compound to the cell culture on or about the end of the initial growth phase; wherein the onset of the death phase is delayed.

The onset of the death phase may be delayed for any period of time. By way of example only, the onset of the death phase may be delayed for 1-10 days, for 2-9 days, for 3-8 days, or for about 5 days. Preferably, the onset of the death phase is delayed for one or more days, more preferably for two or more days, more preferably for three or more days, most preferably for four or more days. In another particular embodiment of the cell culture process and method of increasing cell viability of the invention described above, polyanionic compound is added at a time after innoculation that is during the initial death phase.

It has been found (see Examples 7 and 8) that when polyanionic compound is added during the initial death phase, the death phase may be arrested. To arrest the death phase means to stop, for some period of time, the decline in viable cell density observed in the absence of the addition of polyanionic compound. The arrest may occur immediately following the addition of the polyanionic compound, or may occur at a later time. When the death phase is arrested, what follows may be either a growth phase or a stationary phase. Eventually, of course, the culture will again enter a death phase.

Thus, in other embodiments, the invention is directed to (1) a cell culturing process, and (2) a process for arresting the death phase of a cell culture comprising: culturing host cells which express a protein of interest; and adding polyanionic compound to the cell culture at a time during the initial death phase; wherein the death phase is arrested.

The death phase may be arrested for any period of time before death phase is re-entered. By way of example only, the death phase may be arrested for 1-20 days, for 2-18 days, for 5-15 days, or for 8-13 days. Preferably, the death phase is arrested for one or more days, more preferably for n two or more days, more preferably for three or more days, most preferably for four or more days. Continuity of the arrest of death is not necessarily implied, i.e. there may be "local" decreases in the viable cell density profile between two stretches of constant or increasing viable cell density.

Run times of cell culture processes, particularly non-continuous processes, are usually limited by the remaining viable cell density, which decreases during the death phase. Longer run times may allow higher product titers to be achieved. Delaying the death phase, including extending the growth phase, as much as possible, or arresting the death phase, is therefore desirable. Product quality concerns also offer a motivation for delaying or arresting the death phase, as cell death can release sialidases to the culture supernatant, which may reduce the sialic acid content of the protein expressed. Protein purification concerns offer yet another motivation for delaying or arresting the death phase. The presence of cell debris and the contents of dead cells in the culture can negatively impact on the ability to isolate and/or purify the protein product at the end of the culturing run.

In particular embodiments, any of the herein-described cell culture processes involving two or more temperature shifts and any of the herein-described the cell culture processes involving delayed addition of polyanionic compound are used together in a cell culture. In particular embodiments, the invention is directed to (i) a cell culturing process, and (ii) a process for increasing cell viability, comprising: a) culturing host cells which produce a protein of interest at a temperature at or near 37° C. under conditions and for a time period that allow for cell growth; b) lowering the temperature of the cell culture and culturing the cells at a second temperature at or near 34° C. starting about day 5 to day 7; (c) again lowering the temperature of the cell culture and culturing the cells at a third temperature at or near 32° C. starting about day 6 to day 14; and (d) adding polyanionic compound to the cell culture at a time after innoculation.

Techniques and Procedures Relating to Glycoprotein Purification and Analysis

In the culturing methods encompassed by the present invention (both the cell culture methods involving two or more temperature shifts and the cell culture methods involving delayed addition of polyanionic compound), the protein produced by the cells is typically collected, recovered, isolated, and/or purified, or substantially purified, as desired, at the end of the total cell culture period using isolation and purification methods as known and practiced in the art. Preferably, glycoprotein that is secreted from the cultured cells is isolated from the culture medium or supernatant; however, protein can also be recovered from the host cells, e.g., cell lysates, using methods that are known and practiced in the art, and as further described below.

The complex carbohydrate comprising the glycoprotein produced by the processes of this invention can be routinely analyzed, if desired, by conventional techniques of carbohydrate analysis. For example, techniques such as lectin blotting, well-known in the art, reveal proportions of terminal mannose, or other sugars such as galactose. Termination of mono-, bi-, tri-, or tetra-antennary oligosaccharide by sialic acids can be confirmed by release of sugars from the protein using anhydrous hydrazine or enzymatic methods and fractionation of oligosaccharides by ion-exchange chromatography, size exclusion chromatography, or other methods that are well-known in the art.

The pI of the glycoprotein can also be measured, before and after treatment with neuraminidase, to remove sialic acids. An increase in pI following neuraminidase treatment indicates the presence of sialic acids on the glycoprotein. Carbohydrate structures typically occur on the expressed protein as N-linked or O-linked carbohydrates. The N-linked and O-linked carbohydrates differ primarily in their core structures. N-linked glycosylation refers to the attachment of the carbohydrate moiety via GlcNAc to an asparagine residue in the peptide chain. The N-linked carbohydrates all contain a common Man1-6(Man1-3)Manβ1-4GlcNAcβ1-4GlcNAcβ-R core structure, where R in this core structure represents an asparagine residue. The peptide sequence of the protein produced will contain an asparagine-X-serine, asparagine-X-threonine, and asparagine-X-cysteine, wherein X is any amino acid except proline.

In contrast, O-linked carbohydrates are characterized by a common core structure, which is GalNAc attached to the hydroxyl group of a threonine or serine. Of the N-linked and O-linked carbohydrates, the most important are the complex N- and O-linked carbohydrates. Such complex carbohydrates contain several antennary structures. The mono-, bi-, tri, -, and tetra-, outer structures are important for the addition of terminal sialic acids. Such outer chain structures provide for additional sites for the specific sugars and linkages that comprise the carbohydrates of the protein products.

The resulting carbohydrates can be analyzed by any method known in the art. Several methods are known in the art for glycosylation analysis and are useful in the context of the present invention. These methods provide information regarding the identity and the composition of the oligosaccharide attached to the produced peptide. Methods for carbohydrate analysis useful in connection with the present invention include, but are not limited to, lectin chromatography; HPAEC-PAD, which uses high pH anion exchange chromatography to separate oligosaccharides based on charge; NMR; Mass spectrometry; HPLC; GPC; monosaccharide compositional analysis; and sequential enzymatic digestion.

In addition, methods for releasing oligosaccharides are known and practiced in the art. These methods include 1) enzymatic methods, which are commonly performed using peptide-N-glycosidase F/endo-α-galactosidase; 2) β elimination methods, using a harsh alkaline environment to release mainly O-linked structures; and 3) chemical methods using anhydrous hydrazine to release both N- and O-linked oligosaccharides. Analysis can be performed using the following steps: 1. Dialysis of the sample against deionized water to remove all buffer salts, followed by lyophilization. 2. Release of intact oligosaccharide chains with anhydrous hydrazine. 3. Treatment of the intact oligosaccharide chains with anhydrous methanolic HCl to liberate individual monosaccharides as O-methyl derivatives. 4. N-acetylation of any primary amino groups. 5. Derivatization to yield per-O-trimethylsilyl methyl glycosides. 6. Separation of these derivatives by capillary gas-liquid chromatography (GLC) on a CP-SIL8 column. 7. Identification of individual glycoside derivatives by retention time from the GLC and mass spectroscopy, compared to known standards. 8. Quantification of individual derivatives by FID with an internal standard (13-O-methyl-D-glucose).

Neutral and amino sugars can be determined by high performance anion-exchange chromatography combined with pulsed amperometric detection (HPAE-PAD Carbohydrate System; Dionex Corp.). For instance, sugars can be released by hydrolysis in 20% (v/v) trifluoroacetic acid at 100° C. for 6 hours. Hydrolysates are then dried by lyophilization or with a Speed-Vac (Savant Instruments). Residues are then dissolved in 1% sodium acetate trihydrate solution and analyzed on an HPLC-AS6 column (as described by Anumula et al., 1991, *Anal. Biochem.*, 195:269-280).

Alternatively, immunoblot carbohydrate analysis can be performed. In this procedure protein-bound carbohydrates are detected using a commercial glycan detection system (Boehringer), which is based on the oxidative immunoblot procedure described by Haselbeck et al. (1993, *Glycoconjugate J.*, 7:63). The staining protocol recommended by the manufacturer is followed except that the protein is transferred to a polyvinylidene difluoride membrane instead of a nitrocellulose membrane and the blocking buffers contain 5% bovine serum albumin in 10 mM Tris buffer, pH 7.4, with 0.9% sodium chloride. Detection is carried out with anti-digoxigenin antibodies linked with an alkaline phosphate conjugate (Boehringer), 1:1000 dilution in Tris buffered saline using the phosphatase substrates, 4-nitroblue tetrazolium chloride, 0.03% (w/v) and 5-bromo-4 chloro-3-indoyl-phosphate 0.03% (w/v) in 100 mM Tris buffer, pH 9.5, containing 100 mM sodium chloride and 50 mM magnesium chloride. The protein bands containing carbohydrate are usually visualized in about 10 to 15 minutes.

Carbohydrate associated with protein can also be analyzed by digestion with peptide-N-glycosidase F. According to this procedure the residue is suspended in 14 μL of a buffer containing 0.18% SDS, 18 mM beta-mercaptoethanol, 90 mM phosphate, 3.6 mM EDTA, at pH 8.6, and heated at 100° C. for 3 minutes. After cooling to room temperature, the sample is divided into two equal parts. One part, which is not treated further, serves as a control. The other part is adjusted to about 1% NP-40 detergent followed by the addition of 0.2 units of peptide-N-glycosidase F (Boehringer). Both samples are warmed at 37° C. for 2 hours and then analyzed by SDS-polyacrylamide gel electrophoresis.

In addition, the sialic acid content of the glycoprotein product is assessed by conventional methods. For example, sialic acid can be separately determined by a direct colorimetric method (Yao et al., 1989, *Anal. Biochem.*, 179:332-335), preferably using triplicate samples. Another method of sialic acid determination involves the use of thiobarbaturic acid (TBA), as described by Warren et al., 1959, *J. Biol. Chem.*, 234:1971-1975). Yet another method involves high performance chromatography, such as described by H. K. Ogawa et al., 1993, *J. Chromatography*, 612:145-149.

Illustratively, for glycoprotein recovery, isolation and/or purification, the cell culture medium or cell lysate is centrifuged to remove particulate cells and cell debris. The desired polypeptide product is isolated or purified away from contaminating soluble proteins and polypeptides by suitable purification techniques. The following procedures provide exemplary, yet nonlimiting purification methods for proteins: separation or fractionation on immunoaffinity or ion-exchange columns; ethanol precipitation; reverse phase HPLC; chromatography on a resin, such as silica, or cation exchange resin, e.g., DEAE; chromatofocusing; SDS-PAGE; ammonium sulfate precipitation; gel filtration using, e.g., Sephadex G-75, Sepharose; protein A sepharose chromatography for removal of immunoglobulin contaminants; and the like. Other additives, such as protease inhibitors (e.g., PMSF or proteinase K) can be used to inhibit proteolytic degradation during purification. It will be understood by the skilled practitioner that purification methods for a given polypeptide of interest may require modifications which allow for changes in the polypeptide expressed recombinantly in cell culture. Those purification procedures that can select for carbohydrates and enrich for sialic acid are particularly preferred, e.g., ion-exchange soft gel chromatography, or HPLC using cation- or anion-exchange resins, in which the more acidic fraction(s) is/are collected.

Cells, Proteins and Cell Cultures

In the cell culture processes or methods of this invention (both the cell culture methods involving two or more temperature shifts and the cell culture methods involving delayed addition of polyanionic compound), the cells can be maintained in a variety of cell culture media. i.e., basal culture media, as conventionally known in the art. For example, the methods are applicable for use with large volumes of cells maintained in cell culture medium, which can be supplemented with nutrients and the like. Typically, "cell culturing medium" (also called "culture medium") is a term that is understood by the practitioner in the art and is known to refer to a nutrient solution in which cells, preferably animal or mammalian cells, are grown and which generally provides at least one or more components from the following: an energy source (usually in the form of a carbohydrate such as glucose); all essential amino acids, and generally the twenty basic amino acids, plus cysteine; vitamins and/or other organic compounds typically required at low concentrations; lipids or free fatty acids, e.g., linoleic acid; and trace elements, e.g., inorganic compounds or naturally occurring elements that are typically required at very low concentrations, usually in the micromolar range. Cell culture medium can also be supplemented to contain a variety of optional components, such as hormones and other growth factors, e.g., insulin, transferrin, epidermal growth factor, serum, and the like; salts, e.g., calcium, magnesium and phosphate, and buffers, e.g., HEPES; nucleosides and bases, e.g., adenosine, thymidine, hypoxanthine; and protein and tissue hydrolysates, e.g., hydrolyzed animal protein (peptone or peptone mixtures, which can be obtained from animal byproducts, purified gelatin or plant material); antibiotics, e.g., gentamycin; and cell protective agents, e.g., a Pluronic polyol (Pluronic F68). Preferred is a cell nutrition medium that is serum-free and free of products or ingredients of animal origin.

As is appreciated by the practitioner, animal or mammalian cells are cultured in a medium suitable for the particular cells being cultured and which can be determined by the person of skill in the art without undue experimentation. Commercially available media can be utilized and include, for example, Minimal Essential Medium (MEM, Sigma, St. Louis, Mo.); Ham's F10 Medium (Sigma); Dulbecco's Modified Eagles Medium (DMEM, Sigma); RPMI-1640 Medium (Sigma); HyClone cell culture medium (HyClone, Logan, Utah); and chemically-defined (CD) media, which are formulated for particular cell types, e.g., CD-CHO Medium (Invitrogen, Carlsbad, Calif.). To the foregoing exemplary media can be added the above-described supplementary components or ingredients, including optional components, in appropriate concentrations or amounts, as necessary or desired, and as would be known and practiced by those having in the art using routine skill.

In addition, cell culture conditions suitable for the methods of the present invention are those that are typically employed and known for batch, fed-batch, or continuous culturing of cells, with attention paid to pH, e.g., about 6.5 to about 7.5; dissolved oxygen ($O_2$), e.g., between about 5-90% of air saturation and carbon dioxide ($CO_2$), agitation and humidity, in addition to temperature. As an illustrative, yet nonlimiting, example, a suitable cell culturing medium for the fed-batch processes of the present invention comprises a modified CD-CHO Medium (Invitrogen, Carlsbad, Calif.), e.g., Example 1. A feeding medium can also be employed, such as modified eRDF medium (Invitrogen, Carlsbad, Calif.), e.g., Example 1 or Example 7. Preferred is a feeding medium also containing D-galactose.

Animal cells, mammalian cells, cultured cells, animal or mammalian host cells, host cells, recombinant cells, recombinant host cells, and the like, are all terms for the cells that can be cultured according to the processes of this invention. Such cells are typically cell lines obtained or derived from mammals and are able to grow and survive when placed in either monolayer culture or suspension culture in medium containing appropriate nutrients and/or growth factors. Growth factors and nutrients that are necessary for the growth and maintenance of particular cell cultures are able to be readily determined empirically by those having skill in the pertinent art, such as is described, for example, by Barnes and Sato, (1980, *Cell,* 22:649); in *Mammalian Cell Culture*, Ed. J. P. Mather, Plenum Press, NY, 1984; and in U.S. Pat. No. 5,721,121.

Numerous types of cells can be cultured according to the methods of the present invention. The cells are typically animal or mammalian cells that can express and secrete, or that can be molecularly engineered to express and secrete, large quantities of a particular protein, more particularly, a glycoprotein of interest, into the culture medium. It will be understood that the glycoprotein produced by a host cell can be endogenous or homologous to the host cell. Alternatively, and preferably, the glycoprotein is heterologous, i.e., foreign, to the host cell, for example, a human glycoprotein produced and secreted by a Chinese hamster ovary (CHO) host cell. Also preferably, mammalian glycoproteins, i.e., those originally obtained or derived from a mammalian organism, are attained by the methods the present invention and are preferably secreted by the cells into the culture medium.

Examples of mammalian glycoproteins that can be advantageously produced by the methods of this invention include, without limitation, cytokines, cytokine receptors, growth factors (e.g., epidermal growth factor (EGF), human epidermal growth factor receptor-2 (HER-2), fibroblast growth factor-alpha (FGF-α), fibroblast growth factor-beta (FGF-β), transforming growth factor-alpha (TGF-α), transforming growth factor-beta (TGF-β), platelet-derived growth factor (PDGF), insulin-like growth factor-1 (IGF-1), insulin-like growth factor-2 (IGF-2), nerve growth factor (NGF), nerve growth factor-beta (NGF-β)); growth factor receptors, including fusion or chimeric proteins. Other nonlimiting examples include growth hormones (e.g., human growth hormone, bovine growth hormone); insulin (e.g., insulin A chain and insulin B chain), proinsulin; erythropoietin (EPO); colony stimulating factors (e.g., granulocyte colony-stimulating factor (G-CSF), granulocyte macrophage colony-stimulating factor (GM-CSF), macrophage colony-stimulating factor (M-CSF)); interleukins (e.g., IL-1 through IL-12); vascular endothelial growth factor (VEGF) and its receptor (VEGF-R); interferons (e.g., IFN-α, β, or γ); tumor necrosis factor (e.g., TNF-α and TNF-β) and their receptors, TNFR-1 and TNFR-2; thrombopoietin (TPO); thrombin; brain natriuretic peptide (BNP); clotting factors (e.g., Factor VIII, Factor IX, von Willebrands factor, and the like); anti-clotting factors; tissue plasminogen activator (TPA), e.g., urokinase or human urine or tissue type TPA; follicle stimulating hormone (FSH); luteinizing hormone (LH); calcitonin; CD proteins (e.g., CD3, CD4, CD8, CD28, CD19, etc.); CTLA proteins (e.g., CTLA4); T-cell and B-cell receptor proteins; bone morphogenic proteins (BNPs, e.g., BMP-1, BMP-2, BMP-3, etc.); neurotrophic factors, e.g., bone derived neurotrophic factor (BDNF); neurotrophins, e.g., 3-6; renin; rheumatoid factor; RANTES; albumin; relaxin; macrophage inhibitory protein (e.g., MIP-1, MIP-2); viral proteins or antigens; surface membrane proteins; ion channel proteins; enzymes; regulatory proteins; antibodies; immunomodulatory proteins, (e.g., HLA, MHC, the B7 family); homing receptors; transport proteins; superoxide dismutase (SOD); G-protein coupled receptor proteins (GPCRs); neuromodulatory proteins; Alzheimer's Disease associated proteins and peptides, (e.g., A-beta), and others as known in the art. Fusion proteins and polypeptides, chimeric proteins and polypeptides, as well as fragments or portions, or mutants, variants, or analogues of any of the aforementioned proteins and polypeptides are also included among the suitable proteins, polypeptides and peptides that can be produced by the methods of the present invention.

Nonlimiting examples of animal or mammalian host cells suitable for harboring, expressing, and producing proteins for subsequent isolation and/or purification include Chinese hamster ovary cells (CHO), such as CHO-K1 (ATCC CCL-61), DG44 (Chasin et al., 1986, *Som. Cell Molec. Genet.,* 12:555-556; and Kolkekar et al., 1997, *Biochemistry,* 36:10901-10909), CHO-K1 Tet-On cell line (Clontech), CHO designated ECACC 85050302 (CAMR, Salisbury, Wiltshire, UK), CHO clone 13 (GEIMG, Genova, IT), CHO clone B (GEIMG, Genova, IT), CHO-K1/SF designated ECACC 93061607 (CAMR, Salisbury, Wiltshire, UK), RR-CHOK1 designated ECACC 92052129 (CAMR, Salisbury, Wiltshire, UK), dihydrofolate reductase negative CHO cells (CHO/-DHFR, Urlaub and Chasin, 1980, *Proc. Natl. Acad. Sci. USA,* 77:4216), and dp12.CHO cells (U.S. Pat. No. 5,721, 121); monkey kidney CV1 cells transformed by SV40 (COS cells, COS-7, ATCC CRL-1651); human embryonic kidney cells (e.g., 293 cells, or 293 cells subcloned for growth in suspension culture, Graham et al., 1977, *J. Gen. Virol.,* 36:59); baby hamster kidney cells (BHK, ATCC CCL-10); monkey kidney cells (CV1, ATCC CCL-70); African green monkey kidney cells (VERO-76, ATCC CRL-1587; VERO, ATCC CCL-81); mouse sertoli cells (TM4, Mather, 1980, *Biol. Reprod.,* 23:243-251); human cervical carcinoma cells (HELA, ATCC CCL-2); canine kidney cells (MDCK, ATCC CCL-34); human lung cells (W138, ATCC CCL-75); human hepatoma cells (HEP-G2, HB 8065); mouse mammary tumor cells (MMT 060562, ATCC CCL-51); buffalo rat liver cells (BRL 3A, ATCC CRL-1442); TRI cells (Mather, 1982, *Annals NYAcad. Sci.,* 383:44-68); MCR 5 cells; FS4 cells. Preferred are CHO cells, particularly, CHO/-DHFR cells.

The cells suitable for culturing in the methods and processes of the present invention can contain introduced, e.g., via transformation, transfection, infection, or injection, expression vectors (constructs), such as plasmids and the like, that harbor coding sequences, or portions thereof, encoding the proteins for expression and production in the culturing process. Such expression vectors contain the necessary elements for the transcription and translation of the inserted coding sequence. Methods which are well known to and practiced by those skilled in the art can be used to construct expression vectors containing sequences encoding the produced proteins and polypeptides, as well as the appropriate transcriptional and translational control elements. These methods include in vitro recombinant DNA techniques, synthetic techniques, and in vivo genetic recombination. Such techniques are described in J. Sambrook et al., 1989, *Molecular Cloning, A Laboratory Manual*, Cold Spring Harbor Press, Plainview, N.Y. and in F. M. Ausubel et al., 1989, *Current Protocols in Molecular Biology*, John Wiley & Sons, New York, N.Y.

Control elements, or regulatory sequences, are those non-translated regions of the vector, e.g., enhancers, promoters, 5' and 3' untranslated regions, that interact with host cellular proteins to carry out transcription and translation. Such elements can vary in their strength and specificity. Depending on the vector system and host cell utilized, any number of suitable transcription and translation elements, including constitutive and inducible promoters, can be used. In mammalian cell systems, promoters from mammalian genes or from mammalian viruses are preferred. The constructs for use in protein expression systems are designed to contain at least one promoter, an enhancer sequence (optional, for mammalian expression systems), and other sequences as necessary or required for proper transcription and regulation of gene expression (e.g., transcriptional initiation and termination sequences, origin of replication sites, polyadenylation sequences, e.g., the Bovine Growth Hormone (BGH) poly A sequence).

As will be appreciated by those skilled in the art, the selection of the appropriate vector, e.g., plasmid, components for proper transcription, expression, and isolation of proteins produced in eukaryotic (e.g., mammalian) expression systems is known and routinely determined and practiced by those having skill in the art. The expression of proteins by the cells cultured in accordance with the methods of this invention can placed under the control of promoters such as viral promoters, e.g., cytomegalovirus (CMV), Rous sarcoma virus (RSV), phosphoglycerol kinase (PGK), thymidine kinase (TK), or the α-actin promoter. Further, regulated promoters confer inducibility by particular compounds or molecules, e.g., the glucocorticoid response element (GRE) of mouse mammary tumor virus (MMTV) is induced by glucocorticoids (V. Chandler et al., 1983, *Cell*, 33:489-499). Also, tissue-specific promoters or regulatory elements can be used (G. Swift et al., 1984, *Cell*, 38:639-646), if necessary or desired.

Expression constructs can be introduced into cells by a variety of gene transfer methods known to those skilled in the art, for example, conventional gene transfection methods, such as calcium phosphate co-precipitation, liposomal transfection, microinjection, electroporation, and infection or viral transduction. The choice of the method is within the competence of the skilled practitioner in the art. It will be apparent to those skilled in the art that one or more constructs carrying DNA sequences for expression in cells can be transfected into the cells such that expression products are subsequently produced in and/or obtained from the cells.

In a particular aspect, mammalian expression systems containing appropriate control and regulatory sequences are preferred for use in protein expressing mammalian cells of the present invention. Commonly used eukaryotic control sequences for use in mammalian expression vectors include promoters and control sequences compatible with mammalian cells such as, for example, the cytomegalovirus (CMV) promoter (CDM8 vector) and avian sarcoma virus (ASV), (πLN). Other commonly used promoters include the early and late promoters from Simian Virus 40 (SV40) (Fiers et al., 1973, *Nature*, 273:113), or other viral promoters such as those derived from polyoma, Adenovirus 2, and bovine papilloma virus. An inducible promoter, such as hMTII (Karin et al., 1982, *Nature*, 299:797-802) can also be used.

Examples of expression vectors suitable for eukaryotic host cells include, but are not limited to, vectors for mammalian host cells (e.g., BPV-1, pHyg, pRSV, pSV2, pTK2 (Maniatis); pIRES (Clontech); pRc/CMV2, pRc/RSV, pSFV1 (Life Technologies); pVPakc Vectors, pCMV vectors, pSG5 vectors (Stratagene), retroviral vectors (e.g., pFB vectors (Stratagene)), pcDNA-3 (Invitrogen), adenoviral vectors; Adeno-associated virus vectors, baculovirus vectors, yeast vectors (e.g., pESC vectors (Stratagene)), or modified forms of any of the foregoing. Vectors can also contain enhancer sequences upstream or downstream of promoter region sequences for optimizing gene expression.

A selectable marker can also be used in a recombinant vector (e.g., a plasmid) to confer resistance to the cells harboring (preferably, having stably integrated) the vector to allow their selection in appropriate selection medium. A number of selection systems can be used, including but not limited to, the Herpes Simplex Virus thymidine kinase (HSV TK), (Wigler et al., 1977, *Cell*, 11:223), hypoxanthine-guanine phosphoribosyltransferase (HGPRT), (Szybalska and Szybalski, 1992, *Proc. Natl. Acad. Sci. USA*, 48:202), and adenine phosphoribosyltransferase (Lowy et al., 1980, *Cell*, 22:817) genes, which can be employed in tk-, hgprt-, or aprt-cells (APRT), respectively.

Anti-metabolite resistance can also be used as the basis of selection for the following nonlimiting examples of marker genes: dhfr, which confers resistance to methotrexate (Wigler et al., 1980, *Proc. Natl. Acad. Sci. USA*, 77:357; and O'Hare et al., 1981, *Proc. Natl. Acad. Sci. USA*, 78:1527); gpt, which confers resistance to mycophenolic acid (Mulligan and Berg, 1981, *Proc. Natl. Acad. Sci. USA*, 78:2072); neo, which confers resistance to the aminoglycoside G418 (*Clinical Pharmacy*, 12:488-505; Wu and Wu, 1991, *Biotherapy*, 3:87-95; Tolstoshev, 1993, *Ann. Rev. Pharmacol. Toxicol.*, 32:573-596; Mulligan, 1993, *Science*, 260:926-932; Anderson, 1993, *Ann. Rev. Biochem.*, 62:191-21; May, 1993, *TIB TECH*, 11(5):155-215; and hygro, which confers resistance to hygromycin (Santerre et al., 1984, *Gene*, 30:147). Methods commonly known in the art of recombinant DNA technology can be routinely applied to select the desired recombinant cell clones, and such methods are described, for example, in Ausubel et al. (eds.), *Current Protocols in Molecular Biology*, John Wiley & Sons, NY (1993); Kriegler, 1990, *Gene Transfer and Expression, A Laboratory Manual*, Stockton Press, NY; in Chapters 12 and 13, Dracopoli et al. (eds), *Current Protocols in Human Genetics*, John Wiley & Sons, NY (1994); Colberre-Garapin et al., 1981. *J. Mol. Biol.*, 150:1, which are incorporated by reference herein in their entireties.

In addition, the expression levels of an expressed protein molecule can be increased by vector amplification (for a review, see Bebbington and Hentschel, "The use of vectors based on gene amplification for the expression of cloned genes in mammalian cells in DNA cloning", Vol. 3, Academic Press, New York, 1987). When a marker in the vector system expressing a protein is amplifiable, an increase in the level of inhibitor present in the host cell culture will increase the number of copies of the marker gene. Since the amplified region is associated with the protein-encoding gene, production of the protein will concomitantly increase (Crouse et al., 1983, *Mol. Cell. Biol.*, 3:257).

Vectors which harbor glutamine synthase (GS) or dihydrofolate reductase (DHFR) encoding nucleic acid as the selectable markers can be amplified in the presence of the drugs methionine sulphoximine or methotrexate, respectively. An advantage of glutamine synthase based vectors is the availability of cell lines (e.g., the murine myeloma cell line, NSO) which are glutamine synthase negative. Glutamine synthase expression systems can also function in glutamine synthase expressing cells (e.g., CHO cells) by providing additional inhibitor to prevent the functioning of the endogenous gene.

Vectors that express DHFR as the selectable marker include, but are not limited to, the pSV2-dhfr plasmid (Subramani et al., *Mol. Cell. Biol.* 1:854 (1981). Vectors that express glutamine synthase as the selectable marker include, but are not limited to, the pEE6 expression vector described in Stephens and Cockett, 1989, *Nucl. Acids. Res.*, 17:7110. A glutamine synthase expression system and components thereof are detailed in PCT publications: WO87/04462; WO86/05807; WO89/01036; WO89/10404; and WO91/06657 which are incorporated by reference herein in their entireties. In addition, glutamine synthase expression vectors that can be used in accordance with the present invention are commercially available from suppliers, including, for example, Lonza Biologics, Inc. (Portsmouth, N.H.).

In a particular embodiment, a nucleic acid sequence encoding a soluble CTLA4 molecule or a soluble CTLA4 mutant molecule can be inserted into a vector designed for expressing foreign sequences in a eukaryotic host. The regulatory elements of the vector can vary according to the particular eukaryotic host. Vectors which express the soluble CTLA4 or soluble CTLA4 mutant in eukaryotic host cells can include enhancer sequences for optimizing protein expression.

Types of Cell Cultures

For the purposes of understanding, yet without limitation, it will be appreciated by the skilled practitioner that cell cultures and culturing runs for protein production can include three general types; namely, continuous culture, batch culture and fed-batch culture. In a continuous culture, for example, fresh culture medium supplement (i.e., feeding medium) is provided to the cells during the culturing period, while old culture medium is removed daily and the product is harvested, for example, daily or continuously. In continuous culture, feeding medium can be added daily and can be added continuously, i.e., as a drip or infusion. For continuous culturing, the cells can remain in culture as long as is desired, so long as the cells remain alive and the environmental and culturing conditions are maintained.

In batch culture, cells are initially cultured in medium and this medium is neither removed, replaced, nor supplemented, i.e., the cells are not "fed" with new medium, during or before the end of the culturing run. The desired product is harvested at the end of the culturing run.

For fed-batch cultures, the culturing run time is increased by supplementing the culture medium one or more times daily (or continuously) with fresh medium during the run, i.e., the cells are "fed' with new medium ("feeding medium") during the culturing period. Fed-batch cultures can include various feeding regimens and times, for example, daily, every other day, every two days, etc., more than once per day, or less than once per day, and so on. Further, fed-batch cultures can be fed continuously with feeding medium.

The desired product is then harvested at the end of the culturing/production run. The present invention preferably embraces fed-batch cell cultures in which the two or more temperature shifts during the culture period yield increased and quality protein production and can extend the protein production phase beyond that which occurs when no temperature shift is used, or when only one temperature shift is used. The present invention preferably embraces fed-batch cell cultures in which polyanionic compound is added at a time after innoculation.

It is also envisioned that in the culturing methods of the present invention, the feeding medium can be supplemented to contain D-galactose, or D-galactose can be fed to the culture through some means other than in the feeding medium. Feeding with galactose-containing feeding medium, or other form of feeding, preferably occurs on a daily basis (or continuously) during and until the end of the culturing run, although other feeding schedules can apply. In such a continuous feeding regimen including D-galactose, the cultures receive feeding medium, for example, as a continuously-supplied "drip", or infusion, or other automated addition to the culture, in a timed, regulated, and/or programmed fashion so as to achieve and maintain the appropriate amount of galactose in the culture. Most preferred is a feeding regimen comprising a one time per day bolus feed with feeding medium containing galactose on each day of the culture run, from the beginning of the culture run to the day of harvesting the cells. In accordance with the methods of this invention involving feeding with galactose, the D-galactose concentration in the feeding medium is preferably provided in an amount which affords a sustained or maintained level of D-galactose in the culture, or reactor, during the culturing process. An amount of D-galactose suitable for use in the feeding medium comprises from about 1 g/L to about 50 g/L, preferably about 3 g/L to about 25 g/L, more preferably about 3 g/L to about 20 g/L. As a specific yet nonlimiting example, 12.5 g/L of D-galactose in the feeding medium is suitable for use in the culturing method of the invention, particularly for example, for 50 L reactor scale. Further, it is preferred that the residual galactose concentration in the feeding medium used for culturing cells (e.g., in a reactor or culturing vessel) is maintained and sustained throughout the culturing run in an amount of about 0.1-10 g/L, preferably, about 0.1-5 g/L, more preferably, about 0.2-5 g/L, more preferably, about 0.2-2.5 g/L, even more preferably, about 0.5-2 g/L, and most preferably about 0.5-1.0 g/L. (See, commonly-assigned patent applications U.S. Ser. No. 60/436,050, filed Dec. 23, 2002, and U.S. Ser. No. 10/740,645 filed concomitantly herewith, the contents of which are hereby incorporated by reference herein in their entirety).

In the aspects of the invention involving two or more temperature shifts, the two or more temperature shifts comprising the cell culture processes of this invention may result in more viable cells surviving in culture until the end of the process or production run. The greater the number of cells that survive, the greater the amount of protein product that is produced in a non-growth associated process of protein production, such as some of those exemplified herein. Thus, in such cases, a greater accumulated amount of a desired product results at the end of the process. According to the present invention, the rate of protein or glycoprotein production by individual cells in the culture (i.e., cell specific productivity) is not affected or increased by the temperature shift culturing processes of the invention. (e.g., see below and Example 4).

According to the present invention, cell culture can be carried out, and glycoproteins can be produced by cells, under conditions for the large or small scale production of proteins, using culture vessels and/or culture apparatuses that are conventionally employed for animal or mammalian cell culture. As is appreciated by those having skill in the art, tissue culture dishes, T-flasks and spinner flasks are typically used on a laboratory scale. For culturing on a larger scale, (e.g., 500 L, 5000 L, and the like, for example, as described in commonly-assigned patent application U.S. Ser. No. 60/436,050, filed Dec. 23, 2002, and U.S. Ser. No. 10/740,645, filed concomitantly herewith, the contents of which are incorporated by reference herein in their entirety) procedures including, but not limited to, a fluidized bed bioreactor, a hollow fiber bioreactor, roller bottle culture, or stirred tank bioreactor systems can be used. Microcarriers may or may not be used with the roller bottle or stirred tank bioreactor systems. The systems can be operated in a batch, continuous, or fed-batch mode. In addition, the culture apparatus or system may or may not be equipped with a cell separator using filters, gravity, centrifugal force, and the like.

Phases of Cell Culture and Associated Parameters

The term "innoculation" refers to the addition of cells to starting medium to begin the culture.

The growth phase of a culture is the phase during which the viable cell density at any time point is higher than at any previous time point.

The stationary phase of a culture is the phase during which the viable cell density is approximately constant (i.e. within measuring error) over a time period of any length.

The death phase of a culture is the phase that comes after the growth phase or after the growth phase and the stationary phase, and during which the viable cell density at any time point is lower than at any previous time point during that phase.

In a growth-associated culture process, such as cases where a polyanionic compound causes an extended growth phase, the production phase may start during the extended growth phase.

In a non-growth associated culture process, the production phase of cell culture may be the stationary phase.

Preferably, the culture medium is supplemented ("fed") during the production phase to support continued protein production, particularly in an extended production phase, and to attain ample quantities of high quality glycoprotein product (as exemplified and/or determined by a high level of end sialic acid content upon protein recovery). Feeding can occur on a daily basis, or according to other schedules to support cell viability and protein production.

During an extended production phase at temperatures which are shifted to be successively lower than the temperature(s) at the growth and standard (initial) production phases, the cells are fed and remain viable. This results in the production of desired protein product for an extended or longer total period of time than occurs at the initial culturing temperature, or when the temperature is shifted from the initial culturing temperature only one time. The culturing process according to the present invention may result in more viable cell survival until the end of the culturing period. Accordingly, in some embodiments, the more cells that survive, the more cells that are producing the desired product. This, in turn, results in a greater accumulated amount of the product at the end of the culturing process, with the rate of protein production by individual cells, i.e., cell specific productivity, remaining the same. (See, e.g., Example 4). Cell specific productivity or cell specific rate, as known in the art, typically refers to the specific expression rate of product produced per cell, or per measure of cell mass or volume. Cell specific productivity is measured in grams of protein produced per cell per day, for example, and can be measured according to an integral method involving the following formulae:

$$dP/dt = q_p X, \text{ or}$$

$$P = q_p \int_0^t X dt$$

where $q_p$ is the cell specific productivity constant; X is the number of cells or cell volume, or cell mass equivalents; and dP/dt is the rate of protein production. Thus, $q_p$ can be obtained from a plot of product concentration versus time integral of viable cells ($\int_0^t X dt$ "viable cell days"). According to this formula, when the amount of glycoprotein product produced is plotted against the viable cell days, the slope is equivalent to the cell specific rate. Viable cells can be determined by several measures, for example, biomass, $O_2$ uptake rate, lactase dehydrogenase (LDH), packed cell volume or turbidity. (e.g., U.S. Pat. No. 5,705,364 to T. Etcheverry et al.)

Production of Soluble CTLA4 Molecules and Soluble CTLA4 Mutant Molecules by the Culturing Methods of the Present Invention In other embodiments encompassed by the present invention, the cell culture methods of the invention (both those involving two or more temperature shifts and involving delayed addition of polyanionic compound) are utilized to produce a soluble CTLA4 molecule or a soluble CTLA4 mutant molecule, as described below. A soluble CTLA4 molecule is preferably a CTLA4 fusion protein, preferably a CTLA4Ig. More preferred is CTLA4Ig that comprises amino acids −1 to 357 or +1 to 357 as shown in FIG. 3. Most preferred is CTLA4Ig that consists of amino acids −1 to 357 or +1 to 357 as shown in FIG. 3. A soluble CTLA4 mutant molecule is preferably L104EA29YIg that comprises amino acids −1 to 357 or +1 to 357 as shown in FIG. 4, most preferably that consists of amino acids −1 to 357 or +1 to 357 as shown in FIG. 4. The two- and three-step temperature shift cell culture methods involving extended production phases for protein product are especially suitable for generating high quality and large amounts of soluble CTLA4 molecules and soluble CTLA4 mutant molecules, by their host cells in culture.

In a preferred embodiment, CTLA4Ig is produced by recombinantly engineered host cells. The CTLA4Ig fusion protein can be recombinantly produced by CHO cells transfected with a vector containing the DNA sequence encoding CTLA4Ig. (See, U.S. Pat. No. 5,844,095 to P. S. Linsley et al., and Example 2 herein). The CTLA4Ig fusion protein is produced in high quantity and is appropriately sialylated when cultured in accordance with the multi-step temperature shift processes of this invention. The invention affords the production of high levels of recoverable protein product, e.g., sialylated CTLA4Ig protein product. In another preferred embodiment, the soluble CTLA4 mutant molecule L104EA29YIg that comprises amino acids −1 to 357 or +1 to 357 as shown in FIG. 4 is produced by the cell culture methods of the present invention.

A ligand for CTLA4 is a B7 molecule. As used herein, "ligand" refers to a molecule that specifically recognizes and binds another molecule. The interaction of a molecule and its ligand can be regulated by the products of the culturing processes of this invention. For example, CTLA4 interaction with its ligand B7 can be blocked by the administration of CTLA4Ig molecules. As other examples, the interaction of Tumor Necrosis Factor (TNF) with its ligand, TNF receptor (TNFR), can be blocked by administration of etanercept or other TNF/TNFR blocking molecules.

Wild type CTLA4 or "non-mutated CTLA4" has the amino acid sequence of naturally occurring, full length CTLA4 as shown in FIG. 5 (and also as described in U.S. Pat. Nos. 5,434,131, 5,844,095, and 5,851,795, incorporated herein by reference in their entirety), or any portion thereof that recognizes and binds a B7 molecule, or interferes with a B7 molecule, so that binding to CD28 and/or CTLA4 (e.g., endogenous CD28 and/or CTLA4) is blocked. Wild type CTLA4 comprises particular portions, including, for example, the extracellular domain of wild type CTLA4 beginning with methionine at position +1 and ending at aspartic acid at position +124, or the extracellular domain of wild type CTLA4 beginning with alanine at position −1 and ending at aspartic acid at position +124 as shown in FIG. 5.

The naturally occurring wild type CTLA4 is a cell surface protein having an N-terminal extracellular domain, a transmembrane domain, and a C-terminal cytoplasmic domain. The extracellular domain binds to a target molecule, such as a B7 molecule. In a cell, the naturally occurring, wild type CTLA4 protein is translated as an immature polypeptide, which includes a signal peptide at the amino, or N-terminal, end. The immature polypeptide undergoes post-translational processing, which includes cleavage and removal of the signal peptide to generate a CTLA4 cleavage product having a newly generated N-terminal end that differs from the N-terminal end in the immature form. One skilled in the art will appreciate that additional post-translational processing may occur, which removes one or more of the amino acids from the newly generated N-terminal end of the CTLA4 cleavage product. The mature CTLA4 protein may start at methionine at position +1 or alanine at position −1. The mature form of the CTLA4 molecule includes the extracellular domain or any portion thereof, which binds to B7.

A CTLA4 mutant molecule, as used herein, refers to a molecule comprising wild type CTLA4 as shown in FIG. 5, or any portion or derivative thereof, that has a mutation, or multiple mutations, in the wild type CTLA4 sequence, preferably in the extracellular domain of wild type CTLA4, and binds B7. A CTLA4 mutant molecule has a sequence that it is similar, but not identical, to the sequence of wild type CTLA4 molecule, but still binds B7. The mutations can include one or more amino acid residues substituted with an amino acid having conservative (e.g., a leucine substituted for an isoleucine) or non-conservative (e.g., a glycine substituted with a tryptophan) structure or chemical properties, amino acid deletions, additions, frameshifts, or truncations.

CTLA4 mutant molecules can include a non-CTLA4 molecule therein or attached thereto, i.e., CTLA4 mutant fusion proteins. The mutant molecules can be soluble (i.e., circulating) or they can be bound to a cell surface (membrane-bound). CTLA4 mutant molecules include L104EA29YIg and those described in U.S. patent application Ser. Nos. 09/865,321, 60/214,065 and 60/287,576; in WO 01/92337 A2; in U.S. Pat. Nos. 6,090,914, 5,844,095 and 5,773,253; and as described in R. J. Peach et al., 1994, *J Exp Med,* 180:2049-2058. CTLA4 mutant molecules can be synthetically or recombinantly produced.

CTLA4Ig is a soluble fusion protein comprising an extracellular domain of wild type CTLA4, or a portion thereof that binds B7, joined to an immunoglobulin (Ig) molecule, or a portion thereof. The extracellular domain of CTLA4 or portion thereof is joined to an Ig moiety comprising all or a portion of an immunoglobulin molecule, preferably all or a portion of an immunoglobulin constant region such as all or a portion of IgCγ1 (IgCgamma1), IgCγ2 (IgCgamma2), IgCγ3 (IgCgamma3), IgCγ4 (IgCgamma4), IgCμ (IgCmu), IgCα1 (IgCalpha1), IgCα2 (IgCalpha2), IgCδ (IgCdelta) or IgCε (IgCepsilon), rendering the fusion molecule soluble. The Ig moiety can include the hinge, CH2 and CH3 domains, or the CH1, hinge, CH2 and CH3 domains, of the aforementioned constant regions or other constant regions. Preferably, the Ig moiety is human or monkey and comprises the hinge, CH2 and CH3 domains. Most preferably the Ig moiety comprises the hinge, CH2 and CH3 domains of human IgCγ1, or consists of the hinge, CH2 and CH3 domains of human IgCγ1. In an Ig moiety of CTLA4Ig, the Ig constant region or portion thereof can be mutated, thus resulting in a reduction of its effector functions (see, e.g., U.S. Pat. Nos. 5,637,481, 5,844, 095 and 5,434,131). As used herein, the terms Ig moiety, Ig constant region, Ig C (constant) domain, IgCγ1 (IgCgamma1), IgCγ2 (IgCgamma2), IgCγ3 (IgCgamma3), IgCγ4 (IgCgamma4), IgCμ (IgCmu), IgCα1 (IgCalpha1), IgCα2 (IgCalpha2), IgCε (IgCdelta) or IgCε (IgCepsilon), include both native sequences and sequences that have been mutated, such as, for example, sequences having mutations in the constant region that reduce effector function.

A particular embodiment related to CTLA4 comprises the extracellular domain of wild type CTLA4 starting at methionine at position +1 and ending at aspartic acid at position +124, or starting at alanine at position −1 to aspartic acid at position +124; a junction amino acid residue glutamine at position +125; and an immunoglobulin portion encompassing glutamic acid at position +126 through lysine at position +357, as shown in FIG. 3. DNA encoding this CTLA4Ig was deposited on May 31, 1991, in the American Type Culture Collection (ATCC), 10801 University Blvd., Manassas, Va. 20110-2209, under the provisions of the Budapest Treaty, and has been accorded ATCC accession number ATCC 68629; P. Linsley et al., 1994, *Immunity* 1:793-80. A CHO cell line expressing CTLA4Ig was deposited on May 31, 1991 in ATCC under identification number CRL-10762. The soluble CTLA4Ig molecules produced according to the methods described herein may or may not include a signal (leader) peptide sequence. FIGS. 3 and 4 include an illustration of a signal (leader) peptide sequence. Typically, the molecules do not include a signal peptide sequence.

L104EA29YIg is a fusion protein that is a soluble CTLA4 mutant molecule comprising an extracellular domain of wild type CTLA4 with amino acid changes A29Y (a tyrosine amino acid residue substituting for an alanine at position 29) and L104E (a glutamic acid amino acid residue substituting for a leucine at position +104) joined to an Ig tail. FIG. 4 illustrates L104EA29YIg. The amino acid sequence of L104EA29YIg comprises alanine at amino acid position −1 to lysine at amino acid position +357 as shown in FIG. 4. Alternatively, the amino acid sequence of L104EA29YIg comprises methionine at amino acid position +1 to lysine at amino acid position +357 as shown in FIG. 4. L104EA29YIg comprises a junction amino acid residue glutamine at position +125 and an Ig portion encompassing glutamic acid at position +126 through lysine at position +357. DNA encoding L104EA29YIg was deposited on Jun. 20, 2000, in the American Type Culture Collection (ATCC) under the provisions of the Budapest Treaty, and has been accorded ATCC accession number PTA-2104. 104EA29Y-Ig is described in co-pending U.S. patent application Ser. Nos. 09/579,927, 60/287,576 and 60/214,065, and in WO/01/923337 A2, which are incorporated by reference herein in their entireties. The soluble L104EA29YIg molecules produced by the culturing methods of this invention may or may not include a signal (leader) peptide sequence. Typically, the molecules produced according to the invention do not include a signal peptide sequence.

As used herein, the term soluble refers to any molecule, or fragment thereof, not bound or attached to a cell, i.e., circulating. For example, CTLA4, B7 or CD28 can be made soluble by attaching an Ig moiety to the extracellular domain of CTLA4, B7 or CD28, respectively. Alternatively, a molecule such as CTLA4 can be rendered soluble by removing its transmembrane domain. Typically, the soluble molecules produced according to the invention do not include a signal (or leader) sequence.

A soluble CTLA4 molecule refers to a non-cell-surface-bound (i.e., circulating) molecule comprising wild type CTLA4, or any portion or derivative that binds B7, including, but not limited to, soluble CTLA4 fusion proteins; soluble CTLA4 fusion proteins such as CTLA4Ig fusion proteins (e.g., ATCC 68629), wherein the extracellular domain of CTLA4 is fused to an Ig moiety that is all or a portion of an Ig molecule, preferably all or a portion of an Ig constant region, such as all or a portion of IgCγ1 (IgCgamma1), IgCγ2 (IgCgamma2), IgCγ3 (IgCgamma3), IgCγ4 IgCgamma4), IgCμ (IgCmu), IgCα1 (IgCalpha1), IgCα2 (IgCalpha2), IgCδ (IgCdelta) or IgCε (IgCepsilon), rendering the fusion molecule soluble; soluble CTLA4 fusion proteins in which the extracellular domain is fused or joined with a portion of a biologically active or chemically active protein such as the papillomavirus E7 gene product (CTLA4-E7), melanoma-associated antigen p97 (CTLA4-p97) or HIV env protein (CTLA4-env gp120), as described in U.S. Pat. No. 5,844,095, herein incorporated by reference in its entirety; hybrid (chimeric) fusion proteins such as CD28/CTLA4Ig as described in U.S. Pat. No. 5,434,131, herein incorporated by reference in its entirety; CTLA4 molecules with the transmembrane domain removed to render the protein soluble (See, e.g., M. K. Oaks et al., 2000, Cellular Immunology, 201:144-153, herein incorporated by reference in its entirety); the soluble CTLA4 mutant molecule L104EA29YIg.

A soluble CTLA4 molecule can also be a soluble CTLA4 mutant molecule. The soluble CTLA4 molecules produced according to this invention may or may not include a signal (leader) peptide sequence. The signal peptide can be any sequence that will permit secretion of the molecule, including the signal peptide from oncostatin M (Malik et al., 1989, Molec. Cell. Biol., 9:2847-2853), or CD5 (N. H. Jones et al., 1986, Nature, 323:346-349), or the signal peptide from any extracellular protein. The soluble CTLA4 molecule produced by the culturing processes of the invention can include the oncostatin M signal peptide linked at the N-terminal end of the extracellular domain of CTLA4. Typically, in the invention the molecules do not include a signal peptide sequence.

CTLA4 fusion protein as used herein refers to a molecule comprising the extracellular domain of wild type CTLA4, or portion thereof that binds to B7, fused to a non-CTLA4 moiety that renders the CTLA4 molecule soluble, such as an Ig moiety. For example, a CTLA4 fusion protein can include the extracellular domain of CTLA4 fused to all or a portion of an Ig constant region. Examples of Ig constant domains (or portions thereof) that may be fused to CTLA4 include all, but are not limited to those listed hereinabove. A CTLA4 fusion protein can also be a CTLA4 mutant molecule.

As used herein, "non-CTLA4 moiety" refers to a molecule or portion thereof that does not bind CD80 and/or CD86 and does not interfere with the binding of CTLA4 to its ligand. Examples include, but are not limited to, an Ig moiety that is all or a portion of an Ig molecule, a portion of a biologically active or chemically active protein such as the papillomavirus E7 gene product (CTLA4-E7), melanoma-associated antigen p97 (CTLA4-p97) or HIV env protein (CTLA4-env gp120) (as described in U.S. Pat. No. 5,844,095, herein incorporated by reference in its entirety). Examples of Ig moieties include all or a portion of an immunoglobulin constant domain, such as IgCγ1 (IgCgamma1), IgCγ2 (IgCgamma2), IgCγ3 (IgCgamma3), IgCγ4 IgCgamma4), IgCμ (IgCmu), IgCα1 (IgCalpha1), IgCα2 (IgCalpha2), IgCδ (IgCdelta) or IgCε (IgCepsilon). The Ig moiety can include the hinge, CH2 and CH3 domains, or the CH1, hinge, CH2 and CH3 domains of the aforementioned constant regions or other constant regions. Preferably, the Ig moiety is human or monkey and includes the hinge, CH2 and CH3 domains. Most preferably the Ig moiety includes the hinge, CH2 and CH3 domains of human IgCγ1, or is the hinge, CH2 and CH3 domains of human IgCγ1. In an Ig moiety, the Ig constant region or portion thereof can be mutated so as to reduce its effector functions (see, e.g., U.S. Pat. Nos. 5,637,481, 5,844,095 and 5,434,131).

The extracellular domain of CTLA4 refers to any portion of wild type CTLA4 that recognizes and binds B7. For example, an extracellular domain of CTLA4 comprises methionine at position +1 to aspartic acid at position +124 (FIG. 5). For example, an extracellular domain of CTLA4 comprises alanine at position −1 to aspartic acid at position +124 (FIG. 5).

As used herein, the term mutation refers to a change in the nucleotide or amino acid sequence of a wild type molecule, for example, a change in the DNA and/or amino acid sequences of the wild type CTLA4 extracellular domain. A mutation in the DNA may change a codon leading to a change in the encoded amino acid sequence. A DNA change may include substitutions, deletions, insertions, alternative splicing, or truncations. An amino acid change may include substitutions, deletions, insertions, additions, truncations, or processing or cleavage errors of the protein. Alternatively, mutations in a nucleotide sequence may result in a silent mutation in the amino acid sequence, as is well understood in the art. As is also understood, certain nucleotide codons encode the same amino acid. Examples include nucleotide codons CGU, CGG, CGC, and CGA which encode the amino acid, arginine (R); or codons GAU, and GAC which encode the amino acid, aspartic acid (D).

Thus, a protein can be encoded by one or more nucleic acid molecules that differ in their specific nucleotide sequence, but still encode protein molecules having identical sequences. The mutant molecule may have one, or more than one, mutation. For guidance, the amino acid coding sequence is as follows:

| Amino Acid | Symbol | One Letter Symbol | Codons |
|---|---|---|---|
| Alanine | Ala | A | GCU, GCC, GCA, GCG |
| Cysteine | Cys | C | UGU, UGC |
| Aspartic Acid | Asp | D | GAU, GAC |
| Glutamic Acid | Glu | E | GAA, GAG |
| Phenylalanine | Phe | F | UUU, UUC |
| Glycine | Gly | G | GGU, GGC, GGA, GGG |
| Histidine | His | H | CAU, CAC |
| Isoleucine | Ile | I | AUU, AUC, AUA |
| Lysine | Lys | K | AAA, AAG |
| Leucine | Leu | L | UUA, UUG, CUU, CUC, CUA, CUG |
| Methionine | Met | M | AUG |
| Asparagine | Asn | N | AAU, AAC |
| Proline | Pro | P | CCU, CCC, CCA, CCG |
| Glutamine | Gln | Q | CAA, CAG |
| Arginine | Arg | R | CGU, CGC, CGA, CGG, AGA, AGG |
| Serine | Ser | S | UCU, UCC, UCA, UCG, AGU, AGC |
| Threonine | Thr | T | ACU, ACC, ACA, ACG |
| Valine | Val | V | GUU, GUC, GUA, GUG |
| Tryptophan | Trp | W | UGG |
| Tyrosine | Tyr | Y | UAU, UAC |

As used herein, a fragment or portion is any part or segment of a molecule. For CTLA4 or CD28, a fragment or portion is preferably the extracellular domain of CTLA4 or CD28, or a part or segment thereof, that recognizes and binds B7 or interferes with a B7 so that it blocks binding to CD28 and/or CTLA4. Also, as used herein, "corresponding" means sharing sequence identity.

B7, as used herein, refers to any member of the B7 family of molecules including, but not limited to, B7-1 (CD80) (Freeman et al., 1989, J. Immunol., 143:2714-2722, herein incorporated by reference in its entirety), B7-2 (CD86) (Freeman et al., 1993, Science, 262:909-911, herein incorporated by reference in its entirety; Azuma et al., 1993, Nature, 366: 76-79, herein incorporated by reference in its entirety) that recognizes and binds CTLA4 and/or CD28. CD28 refers to the molecule that recognizes and binds B7 as described in U.S. Pat. Nos. 5,580,756 and 5,521,288 (herein incorporated by reference in their entireties). As used herein, B7-positive cells include any cells with one or more types of B7 molecules expressed on the cell surface.

As used herein, a "derivative" is a molecule that shares sequence similarity and activity of its parent molecule. For example, a derivative of CTLA4 includes a soluble CTLA4 molecule having an amino acid sequence at least 70% similar to the extracellular domain of wildtype CTLA4, and which recognizes and binds B7 e.g. CTLA4Ig or soluble CTLA4 mutant molecule L104EA29YIg. A derivative means any change to the amino acid sequence and/or chemical quality of the amino acid e.g., amino acid analogs.

As used herein, to regulate an immune response is to activate, stimulate, up-regulate, inhibit, block, reduce, attenuate, down-regulate or modify the immune response. A variety of diseases, e.g., autoimmune diseases, may be treated by regulating an immune response, e.g., by regulating functional CTLA4- and/or CD28-positive cell interactions with B7-positive cells. For example, a method of regulating an immune response comprises contacting B7-positive cells with a soluble CTLA4 molecule, such as those produced according to this invention, to form soluble CTLA4/B7 complexes, wherein the soluble CTLA4 molecule interferes with the reaction of an endogenous CTLA4 and/or CD28 molecule with the B7 molecule. To "block" or "inhibit" a receptor, signal or molecule, as referred to herein, means to interfere with the activation of the receptor, signal or molecule, as detected by an art-recognized test. Blockage or inhibition can be partial or total.

As used herein, "blocking B7 interaction" refers to interfering with the binding of B7 to its ligands, such as CD28 and/or CTLA4, thereby obstructing T-cell and B7-positive cell interactions. Examples of agents that block B7 interactions include, but are not limited to, molecules such as an antibody (or portion thereof) that recognizes and binds to the any of CTLA4, CD28 or B7 molecules (e.g., B7-1, B7-2); a soluble form (or portion thereof) of the molecules such as soluble CTLA4; a peptide fragment or other small molecule designed to interfere with the cell signal through a CTLA4/CD28/B7-mediated interaction. In a preferred embodiment, the blocking agent is a soluble CTLA4 molecule, such as CTLA4Ig (ATCC 68629) or L104EA29YIg (ATCC PTA-2104); a soluble CD28 molecule, such as CD28Ig (ATCC 68628); a soluble B7 molecule, such as B7-Ig (ATCC 68627); an anti-B7 monoclonal antibody (e.g., ATCC HB-253, ATCC CRL-2223, ATCC CRL-2226, ATCC HB-301, ATCC HB-11341 and monoclonal antibodies as described in U.S. Pat. No. 6,113,898 or in Yokochi et al., 1982, *J. Immunol.*, 128(2):823-827); an anti-CTLA4 monoclonal antibody (e.g., ATCC HB-304, and monoclonal antibodies as described in references 82-83); and/or an anti-CD28 monoclonal antibody (e.g. ATCC HB 11944 and MAb 9.3, as described in Hansen et al., 1980, *Immunogenetics*, 10: 247-260, or Martin et al., 1984, *J. Clin. Immunol.*, 4(1):18-22). Blocking B7 interactions can be detected by art-recognized tests such as determining reduction of immune disease (e.g., rheumatic disease) associated symptoms, by determining a reduction in T-cell/B7-cell interactions, or by determining a reduction in the interaction of B7 with CTLA4/CD28. Blockage can be partial or total.

As used herein, an effective amount of a molecule refers to an amount that blocks the interaction of the molecule with its ligand. For example, an effective amount of a molecule that blocks the interaction of B7 with CTLA4 and/or CD28 is the amount of the molecule that, when bound to B7 molecules on B7-positive cells, inhibits B7 molecules from binding endogenous ligands such as CTLA4 and CD28. Alternatively, an effective amount of a molecule that blocks the interaction of B7 with CTLA4 and/or CD28 is the amount of the molecule that, when bound to CTLA4 and/or CD28 molecules on T cells, inhibits B7 molecules from binding endogenous ligands such as CTLA4 and CD28. The inhibition or blockage can be partial or complete.

For clinical protocols, it is preferred that the Ig moiety of a fusion protein, such as CTLA4Ig or mutant CTLA4Ig, does not elicit a detrimental immune response in a subject. The preferred moiety is all or a portion of the Ig constant region, including human or non-human primate Ig constant regions. Examples of suitable Ig regions include IgCγ1 (IgCgamma1), IgCγ2 (IgCgamma2), IgCγ3 (IgCgamma3), IgCγ4 IgCgamma4), IgCµ (IgCmu), IgCα1 (IgCalpha1), IgCα2 (IgCalpha2), IgCδ (IgCdelta) or IgCε (IgCepsilon), including the hinge, CH2 and CH3 domains, or the CH1, hinge, CH2 and CH3 domains, which are involved in effector functions such as binding to Fc receptors, complement-dependent cytotoxicity (CDC), or antibody-dependent cell-mediated cytotoxicity (ADCC). The Ig moiety can have one or more mutations therein, (e.g., in the CH2 domain to reduce effector functions such as CDC or ADCC) where the mutation modulates the capability of the Ig to bind its ligand by increasing or decreasing the capability of the Ig to bind to Fc receptors. For example, mutations in the Ig moiety can include changes in any or all of its cysteine residues within the hinge domain. For example, as shown in FIG. 3, the cysteines at positions +130, +136, and +139 are substituted with serine. The Ig moiety can also include the proline at position +148 substituted with a serine, as shown in FIG. 3. Further, mutations in the Ig moiety can include having the leucine at position +144 substituted with phenylalanine; leucine at position +145 substituted with glutamic acid; or glycine at position +147 substituted with alanine.

EXAMPLES

The following Examples set forth specific aspects of the invention to illustrate the invention and provide a description of the present methods for those of skill in the art. The Examples should not be construed as limiting the invention, as the Examples merely provide specific methodology and exemplification that are useful in the understanding and practice of the invention and its various aspects.

Examples 1-4 as set forth below describe experiments relating to cell culture processes involving temperature shifts during the culture run. Examples 6-11 describe experiments relating to cell culture processes involving delayed addition of polyanionic compound to the culture.

Example 1

This Example provides materials and reagents employed in the processes of the present invention for the culturing of recombinant cells that produce the exemplified CTLA4Ig fusion proteins as described herein in Examples 2-4.

1. Cell Culture Medium

The basal cell culture medium used for all phases of cell inoculum generation and for growth of cultures in bioreactors, including 5 liter (5 L) and 50 liter (50 L) production reactors, was modified CD-CHO medium containing glutamine, sodium bicarbonate, insulin and methotrexate (Invitrogen, Carlsbad, Calif.), as exemplified in Table 1. The pH of the medium was adjusted to 7.0 with 1 N HCl.

TABLE 1

Modified CD-CHO

| Medium Component | Concentration |
|---|---|
| CD-CHO 25 × Acids I (Invitrogen, Carlsbad, CA) | 40 ml/L |
| CD-CHO 25 × Acids II (Invitrogen, Carlsbad, CA) | 40 ml/L |
| CD-CHO 25 × Salts I (Invitrogen, Carlsbad, CA) | 40 ml/L |
| CD-CHO 25 × Salts II (Invitrogen, Carlsbad, CA) | 40 ml/L |
| L-glutamine (Invitrogen) | 0.585 g/L |
| r-human insulin (10 mg/mL) (Invitrogen) | 0.1 ml/L |
| Methotrexate (20 mM solution) (ICN, Costa Mesa, CA) | 5 µl/L |
| Sodium bicarbonate (Mallenkrodt Baker, Phillipsburg, NJ) | 2.22 g/L |

For feeding cells in the fed-batch process, a modified feed medium, i.e., eRDF-1 medium (Invitrogen), containing glucose, glutamine, insulin and TC Yeastolate (Becton-Dickinson, Franklin Lakes, N.J.) was employed, as shown in Table 2. The pH of the feeding medium was adjusted to 7.0 with 1 N NaOH after the addition of all components.

TABLE 2

Modified eRDF Medium

| Component | Concentration |
|---|---|
| eRDF-I (Invitrogen, Carlsbad, CA) | 16.8 g/L |
| dextrose (VWR-Mallenkrodt Baker) | 30.94 g/L |
| L-glutamine (Invitrogen) | 4.1 g/L |
| r-human insulin (10 mg/mL) (Invitrogen) | 1 ml/L |
| TC Yeastolate (Becton Dickinson, Franklin Lakes, NJ) | 5 g/L |

2. Production Phase in Bior Actor

The production bioreactor was initially operated as a batch reactor, with temperature, pressure, pH and dissolved oxygen concentration closely monitored and controlled. The condition of the culture was evaluated by measuring the viable cell density and the concentration of several key metabolites. The feeding process was initiated one day after the inoculation. The remainder of the fermentation was the conducted in fed-batch mode.

Bioreactors of 5 L scale (glass reactor with one marine impeller), and 50 L scale (stainless steel reactor with two marine impellers) were used. (see Example 2). A data acquisition system (Intellution Fix 32) recorded temperature, pH, and dissolved oxygen (DO) throughout runs. Gas flows were controlled via rotameters. Air was sparged into the reactor via a submerged frit (5 µm pore size) and through the reactor head space for $CO_2$ removal. Molecular oxygen was sparged through same frit for DO control. $CO_2$ was sparged through same frit as used for pH control.

3. Feeding Strategy

At 24 hours post inoculation, a daily minimum of 1% of culture volume of modified eRDF-I feed medium was added into the bioreactor if the glucose concentration was ≧3.0 g/L. In cases in which the glucose concentration was below 3 g/L, the volume of the daily bolus feed was calculated to bring the glucose concentration back up to 3.0 g/L. The daily feed amount was recorded on batch sheets.

4. Sampling

Samples of cells were removed from the reactor on a daily basis. A sample used for cell counting was stained with trypan blue (Sigma, St. Louis, Mo.). Cell count and cell viability determination were performed via hemocytometry using a microscope. For analysis of metabolites, additional sample was centrifuged for 20 minutes at 2000 rpm (4° C.) for cell separation. Supernatant was analyzed for the following parameters: titer, sialic acid, glucose, lactate, glutamine, glutamate, pH, $pO_2$, $pCO_2$, ammonia, and, optionally, lactate dehydrogenase (LDH). Additional back-up samples were frozen at −20° C.

Example 2

This Example describes the production of CTLA4Ig, shown as −1 to 357 or +1 to 357 in FIG. 3, (encoding DNA deposited as ATCC 68629), from cultured CHO cells.

This Example also describes a process of this invention for producing both high quantity and high quality CTLA4Ig protein, involving culture runs having two- or three-step temperature shifts and total run times of 14, 21, or 28-30 days. A temperature shift (T-shift) from 37° C. to 34° C. occurred on day 6 (end of logarithmic growth phase) and a second T-shift from 34° C. to 32° C. occurred on day 10. The run was ended on day 14, day 21, or day 28, and for the two-step shift, the temperature was controlled at 32° C. from the shift on day 10 until the end of the run. For the three-step shift, the temperature was controlled at 30° C. from the day of the shift until the end of the run The processes described resulted in increased end titer of protein product, increased end cell viability, and volumetric productivity, compared with single temperature shift or no temperature shift runs. In accordance with the invention, the second and third T-shifts extended the run time of the standard fermentation (culturing) process to two to three weeks (or longer), while maintaining high cell viabilities. A close to linear increase of the titer of product was observed throughout the production period.

CHO cells used for CTLA4Ig expression were expanded in modified CD-CHO medium containing glutamine, sodium bicarbonate, insulin, and methotrexate (see Example 1) using T-75 flasks (Corning, Corning, N.Y.) and 250 and 500 mL spinners (Bellco, Vineland, N.J.). T-flasks and spinners were incubated at 37° C. in 6% $CO_2$. After sufficient inoculum was generated, the culture was transferred into a either a 5 L (Applikon, Foster City, Calif.) or a 50 L bioreactor (Feldmeier, Syracuse, N.Y.) with 3 L or 30 L working volume, respectively, of the above-described medium. The initial seeding density was about $2 \times 10^5$ viable cells/mL.

The 5 L vessel was a glass reactor equipped with one marine impeller (Applikon, Foster City, Calif.); the 50 L vessel was a stainless steel reactor (Feldmeier, Syracuse, N.Y.) equipped with two marine impellers. A data acquisition system using Intellution Fix32 (Intellution, Foxboro, Mass.) recorded temperature, pH, and dissolved oxygen (DO) throughout runs. Gas flows were controlled via rotameters (Cole Parmer, Vernon Hills, Ill.). Air was sparged into the reactor via a submerged frit (5 µm pore size) and through the reactor head space for $CO_2$ removal. Molecular oxygen was sparged through same frit for DO control. $CO_2$ was sparged through the same frit for high side pH control. Low side pH control was realized by addition of 1 N NaOH. Without limitation, acceptable ranges for pH were 6-9, preferably 6.8-7.2, and for osmolarity were 200-500 mOsm, preferably, 280-340 mOsm.

The culture in the bioreactor was given a daily bolus feed using modified eRDF medium (Invitrogen) as described in Example 1, Table 2, as follows: starting one day post inoculation, a minimum of 1% culture volume was added as feeding medium; if the glucose level fell below 3 g/L, a calculated volume was added to bring the glucose level back to 3 g/L.

The fermentation process had a duration of 21 days at 5 L scale and 28 days at 50 L scale. The longer duration of the culture run at 50 L scale correlated with the added temperature shift for that run. Samples were taken on a daily basis from the reactor for analysis. For example, sample used for cell count was stained with trypan blue (Sigma, St. Louis, Mo.). Cell count and cell viability determination was performed using a hemocytometer and counting viable stained cells under a microscope. For analysis of metabolites, an additional sample aliquot was centrifuged for 20 minutes at 2000 rpm (4° C.) to pellet the cells. The supernatant was analyzed for protein titer, sialic acid, glucose, lactate, glutamine, glutamate, pH, $pO_2$, $pCO_2$, ammonia, and LDH, using techniques and protocols conventionally practiced in the art.

Example 3

This Example describes and presents the results of comparative evaluations to assess various culturing procedures, including the multi-step culturing methods performed in accordance with the present invention. The end titer (in g/L) of glycoprotein product was determined, as were the end titer sialic acid content of the protein, the cell viability at the end of the runs (end cell viability) and the cell density at the end of the runs (viable end cell density).

Experiments I-A, I-B and I-C; II-A, II-B and II-C; and III-A, III-B and III-C refer to the same cell culture run with the same temperature shift profile assessed at different times, i.e., for I-A, II-A, and III-A, the product and cell parameters were assessed after 14 days, for I-B, II-B and III-B after 21 days, and for I-C, II-C and III-C after 28 days. These experiments were performed in a 5 L bioreactor in which the culture conditions were controlled as follows: pH at 7.0; dissolved oxygen at 40%; agitation at 60 rpm; and initial temperature at 37° C. The data were obtained from fed-batch cell culture fermentations according to the methods of the present invention.

Experiments I, II and III were designed as follows:
Experiment I: the cell culture temperature was controlled at 37° C. from day 0 to day 21 (no temperature shift).
Experiment II: the cell culture temperature was controlled at 37° C. from day 0 to day 6; and at 34° C. from day 6 to day 21 (single temperature shift).
Experiment III: the cell culture temperature was controlled at 37° C. from day 0 to day 6; at 34° C. from day 6 to day 10; and at 32° C. from day 10 to day 21 (two-step temperature shift procedure of the present invention).

Experiments IV-A and V-A show the results of product titer, end cell viability and viable end cell density assessed after a 14-day culture run with an initial (standard) production phase; Experiments IV-B and V-B show these results assessed after a 21-day culture run with an extended production phase; and Experiments IV-C and V-C show the results assessed after a 28-day culture run with a second extended production phase. Experiments IV and V were performed in a 50 L bioreactor in which the culture conditions were controlled as follows: pH at 7.0; dissolved oxygen at 40%; agitation at 30 rpm; and initial temperature at 37° C.

Experiments IV and V were designed as follows:
Experiment IV: the cell culture temperature was controlled at 37° C. from day 0 to day 6; at 34° C. from day 6 to day 10; and at 32° C. from day 10 to day 28 (two-step temperature shift procedure of the present invention).
Experiment V: the cell culture temperature was controlled at 37° C. from day 0 to day 6; at 34° C. from day 6 to day 10; at 32° C. from day 10 to day 14; and at 30° C. from day 14 to day 28 (three-step temperature shift procedure of the present invention). Experiments V-A, V-B and V-C refer to the same cell culture run with the same temperature shift profile assessed at different times, i.e., for V-A, the product and cell parameters were assessed after 14 days, for V-B, after 21 days, and for V-C, after 28 days.

Experiments I-V represent five different culture runs as described above. As described, runs of 14 days are designated "A"; runs of 21 days are designated "B"; while runs of 28 days are designated "C".

Table 3 presents the results of Experiments demonstrating the impact of different temperature shift profiles on the production of CTLA4Ig by cells in culture at the 5 L reactor scale.

TABLE 3

| Experiment # | Reactor scale (L) | Temperature shift | End titer (g/L) | End titer (%) (Exp. I-A set to 100%) | End SA (NANA*) (molar ratio) | End titer *end SA (NANA) | End cell viability (%) | Viable end cell density (×10⁶ cells/mL) |
|---|---|---|---|---|---|---|---|---|
| | | Product titer, end cell viability and viable end cell density assessed after 14-day run with initial (standard) production phase | | | | | | |
| I-A | 5 | 37° C. (0-14 days) - no T-shift - | 0.73 | 100 | 7.3 | 5.3 | 56 | 0.8 |
| II-A | 5 | 37° C. (0-6 days) 34° C. (6-14 days) - one step T-shift - | 1.30 | 178 | 8.1 | 10.5 | 82 | 1.5 |
| III-A | 5 | 37° C. (0-6 days) 34° C. (6-10 days) | 2.30 | 315 | 7.6 | 17.5 | 81 | 3.1 |

TABLE 3-continued

| Experiment # | Reactor scale (L) | Temperature shift | End titer (g/L) | End titer (%) (Exp. I-A set to 100%) | End SA (NANA*) (molar ratio) | End titer *end SA (NANA) | End cell viability (%) | Viable end cell density (×10⁶ cells/mL) |
|---|---|---|---|---|---|---|---|---|
| | | 32° C. (10-14 days) - two step T-shift - Product titer, end cell viability and viable end cell density assessed after 21-day run with extended production phase | | | | | | |
| I-B | 5 | 37° C. (0-21 days) - no T-shift - | 1.30 | 178 | 6.6 | 8.6 | 20 | 0.3 |
| II-B | 5 | 37° C. (0-6 days) 34° C. (6-21 days) - one step T-shift - | 2.70 | 370 | 5.3 | 14.3 | 28 | 0.4 |
| III-B | 5 | 37° C. (0-6 days) 34° C. (6-10 days) 32° C. (10-21 days) - two step T-shift - | 3.50 | 480 | 6.5 | 22.8 | 57 | 1.7 |

*"NANA" (N-amino-N-neuraminic acid) refers to sialic acid (SA). "End NANA" refers to the NANA of the product at the end of culture.

Table 4 presents the results of Experiments demonstrating the impact of different temperature shift profiles on the production of CTLA4Ig by cells in culture at the 50 L reactor scale.

TABLE 4

| Experiment # | Reactor scale [L] | Temperature shift | End titer (g/L) | End cell viability (%) | Viable end cell density (×10⁶ cells/mL) |
|---|---|---|---|---|---|
| Product titer, end cell viability and viable end cell density assessed after 14-day run with initial (standard) production phase | | | | | |
| IV-A | 50 | 37° C. (0-6 days); 34° C. (6-10 days); 32° C. (10-14 days) - two step T-shift - | 1.4 | 95 | 5.5 |
| V-A | 50 | 37° C. (0-6 days); 34° C. (6-10 days); 32° C. (10-14 days); 30° C. (14-21 days) - three step T-shift - | 1.4 | 91 | 5.4 |
| Product titer, end cell viability and viable end cell density assessed after 21-day run with extended production phase | | | | | |
| IV-B | 50 | 37° C. (0-6 days); 34° C. (6-10 days); 32° C. (10-21 days) - two step T-shift - | 2.5 | 67 | 2.5 |
| V-B | 50 | 37° C. (0-6 days); 34° C. (6-10 days); 32° C. (10-14 days); and 30° C. (14-21 days) - three step T-shift - | 2.6 | 82 | 3.2 |
| Product titer, end cell viability and viable end cell density assessed after 28-day run with further extension of production phase | | | | | |
| IV-C | 50 | 37° C. (0-6 days); 34° C. (6-10 days); and 32° C. (10-28 days) - two step T-shift - | 2.8 | 47 | 1.1 |
| V-C | 50 | 37° C. (0-6 days); 34° C. (6-10 days); 32° C. (10-14 days); 30° C. (14-28 days) - three step T-shift - | 3.1 | 69 | 1.4 |

Figure 1:
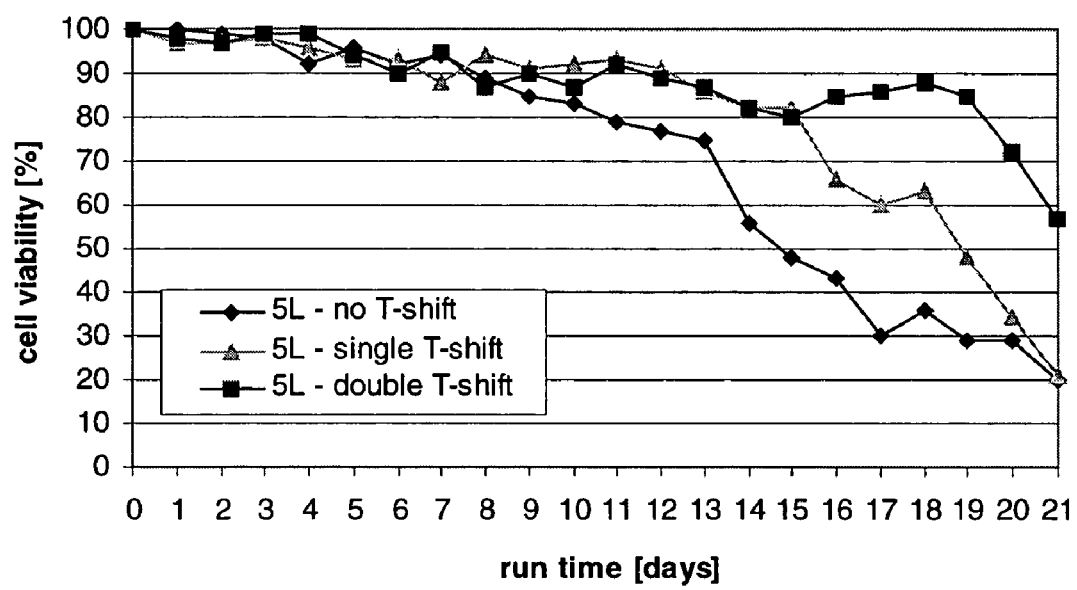

As has been demonstrated by the experiments in this Example, the multi-step temperature shift profiles were found to maintain a high cell viability throughout the culture process. Specifically, in Table 3, Experiment III-B shows that the use of the timed two-step temperature shift profile maintained a high cell viability (see also FIG. 1) throughout the 21-day culturing process (including the extended production phase), allowing the titer to reach 3.5 g/L at a high sialic acid content of 6.5 [molar ratio]. The success of two-step culturing procedure can also be evidenced in the high value of the mathematical product of 'end titer×end sialic acid'.

By contrast, a culturing process involving no temperature shift (Table 3, Experiment I-B) led to an early decline in cell viability. Further, the use of a one-step temperature shift (Table 3, Experiment II-B) was found to yield a lower end titer, end sialic acid, and ('end titer×end sialic acid')—mathematical product compared with the two-step temperature shift profile and process according to this invention.

Figure 2:
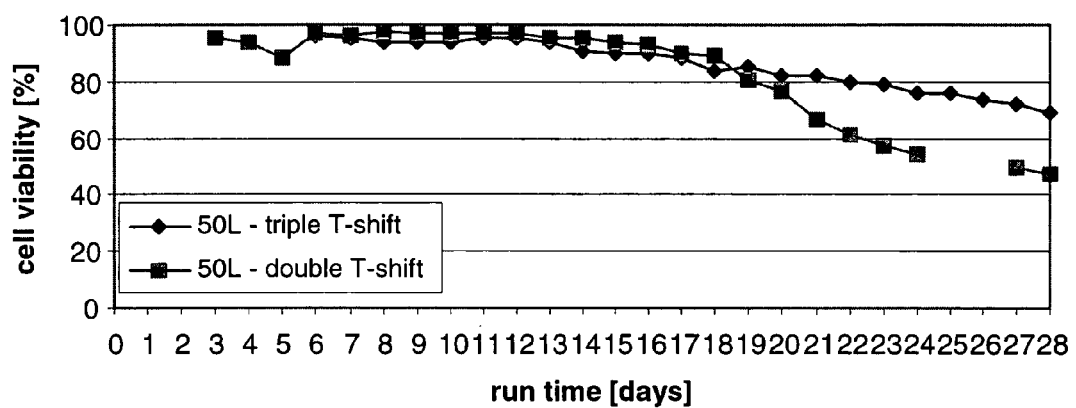

In addition, the results presented in Table 4 involving cell cultures performed at a 50 L reactor scale demonstrate the advantages of the multi-step temperature shift culturing technique of this invention. The third temperature shift to 30° C. was timed to take place on day 14. In particular, the benefits of a triple temperature shift on cell viability and end titer using the triple shift (Table 4, Experiment V-C; also FIG. 2) can be seen compared to a double temperature shift. In accordance with the present methods, the triple temperature shift further extended cell viability and thus, protein production relative to no shift or one shift methods. Due to a scale-up effect, which is usual in cell culture, the titer generation at the 50 L reactor scale was found to be somewhat slower than at the 5 L scale. However, it is readily appreciated that such an effect does not detract from the advantages of the two or more temperature shift culture runs as provided by this invention.

As evidenced by the results presented in Example 3, for those runs in which a temperature shift was performed on day 6, i.e., at the end of the logarithmic growth phase, far better results in end titer and cell viability were obtained, compared with control runs in the absence of a temperature shift. As observed from the results, the volumetric productivity was increased two-fold by the use of a single temperature shift. A second temperature shift on day 10 yielded a higher cell viability and further increased volumetric productivity (approximately 3-fold compared with runs with no T-shift), while the product quality remained high, as determined by the sialic acid content of the glycoprotein product.

Example 4

This Example presents data showing that the cell culture process comprising two downward temperature shifts according to this invention has no statistically significant effect on the amount of protein, e.g., CTLA4Ig in this Example, that is produced per cell per unit time. In accordance with the newly presented cell culturing (fermentation) methods of this invention, the overall production of protein in the process is the result of more viable cells surviving until the end of the process. Because more cells survive for an extended production time, more cells are viably producing the desired protein at the end of the process. This, in turn, yields a greater amount of the desired protein product at the end of the process or culture run.

Table 5 illustrates the cell specific productivity at various times in the process encompassed by the present invention. Cell specific productivity is determined by the formula as presented supra. The culture process designed for the production of CTLA4Ig, other soluble CTLA4 molecules, and soluble CTLA4 mutant molecules is thus a non-growth associated process in which protein production begins on or about day 6, i.e., approximately at the start of the stationary phase, following exponential cell growth. The data presented in Table 5 relate to the experiments conducted in Example 3.

TABLE 5

| Example/T-Shift Parameter | Cell Specific Protein Production (Time) | Amount of Cell Specific Protein Production |
|---|---|---|
| I-A/No T-shift | After 14 days | 44.7 pg/cell/day |
| I-B/No T-shift | After 21 days | 64.1 pg/cell/day |
| II-A/One T-shift | After 14 days | 55.5 pg/cell/day |
| II-B/One T-shift | After 21 days | 60.9 pg/cell/day |
| III-A/Two T-shifts | After 14 days | 47.5 pg/cell/day |
| III-B/Two T-shifts | After 21 days | 51.9 pg/cell/day |

Cell specific productivity in Table 5 was calculated using cell density and titer measurements, as described hereinabove. As will be appreciated by the skilled practitioner in the art, cell density measurements usually have about a 10-20% standard deviation (SD), i.e., a high SD, and are imprecise. Therefore, the determination of cell specific productivity has a corresponding 10-20% standard deviation. Thus, in view of the high SD involved in these types of calculations, the amount of product produced per cell per day for the different run times does not differ significantly among a process having no T-shift, one T-shift, or two T-shifts. The high levels of high quality protein product produced by the newly provided cell culturing processes of this invention, and the overall increase in protein production, are attributed to the higher numbers of viable cells that survive through the entire culturing process comprising multiple downward temperature shifts.

Example 5

Example 5A

This Example provides materials and reagents employed in the processes of the present invention for the culturing of recombinant cells that produce the exemplified L104EA29YIg as described herein in Examples 5B-16.

1. Cell Culture Medium The basal cell culture medium used for all phases of cell inoculum generation was modified CD-CHO medium containing glutamine, sodium bicarbonate, insulin and methotrexate (Invitrogen, Carlsbad, Calif.), as exemplified in Table 6. The pH of the medium was adjusted to 7.0 with 1 N HCl. The basal cell culture medium used for growth of cultures in bioreactors, including 5 liter (5 L), 10 liter (10 L) and 50 liter (50 L) production reactors, was also the modified CD-CHO medium shown in Table 6, except without methotrexate. The pH of the medium was adjusted to 7.0 with 1 N HCl.

TABLE 6

Modified CD-CHO

| Medium Component | Concentration |
|---|---|
| CD-CHO 25 × Acids I (Invitrogen, Carlsbad, CA) | 40 ml/L |
| CD-CHO 25 × Acids II (Invitrogen, Carlsbad, CA) | 40 ml/L |
| CD-CHO 25 × Salts I (Invitrogen, Carlsbad, CA) | 40 ml/L |
| CD-CHO 25 × Salts II (Invitrogen, Carlsbad, CA) | 40 ml/L |
| L-glutamine (Invitrogen) | 0.585 g/L |
| r-human insulin (10 mg/mL) (Invitrogen) | 0.1 ml/L |
| Methotrexate (20 mM solution) (ICN, Costa Mesa, CA) | 5 µl/L |
| Sodium bicarbonate (Mallenkrodt Baker, Phillipsburg, NJ) | 2.22 g/L |

In all Examples except Example 8, for feeding cells in the fed-batch process, a modified feed medium, i.e., eRDF-1 medium (Invitrogen), containing glucose, glutamine, insulin and TC Yeastolate (Becton-Dickinson, Franklin Lakes, N.J.) was employed, as shown in Table 7. The pH of the feeding medium was adjusted to 7.0 with 1 N NaOH after the addition of all components.

TABLE 7

Modified eRDF Medium

| Component | Concentration |
|---|---|
| eRDF-I (Invitrogen, Carlsbad, CA) | 16.8 g/L |
| dextrose (VWR-Mallenkrodt Baker) | 30.94 g/L |

TABLE 7-continued

Modified eRDF Medium

| Component | Concentration |
|---|---|
| L-glutamine (Invitrogen) | 4.1 g/L |
| r-human insulin (10 mg/mL) (Invitrogen) | 1 ml/L |
| TC Yeastolate (Becton Dickinson, Franklin Lakes, NJ) | 5 g/L |
| D-galactose (Ferro-Pfanstiehl, Waukegan, IL) | 12.5 g/L |

For Example 8, the feeding medium was that described above with one modification: eRDF-1 was at a concentration of 25.2 g/L.

2. Production Phase in Bioreactor

The production bioreactor was initially operated as a batch reactor, with temperature, pressure, pH and dissolved oxygen concentration closely monitored and controlled. The condition of the culture was evaluated by measuring the viable cell density and the concentration of several key metabolites. The feeding process was initiated one day after the inoculation. The remainder of the fermentation was the conducted in fed-batch mode.

Bioreactors of 5 L scale (glass reactor with one marine impeller), 10 L scale (glass reactor with two marine impellers) and 50 L scale (stainless steel reactor with two marine impellers) were used. (see Example 2). A data acquisition system (Intellution Fix 32) recorded temperature, pH, and dissolved oxygen (DO) throughout runs. Gas flows were controlled via rotameters. Air was sparged into the reactor via a submerged frit (5 μm pore size) and through the reactor head space for $CO_2$ removal. Molecular oxygen was sparged through same frit for DO control. $CO_2$ was sparged through same frit as used for pH control.

3. Feeding Strategy

At 24 hours post inoculation, a daily minimum of 1% of culture volume of modified eRDF-I feed medium was added into the bioreactor if the glucose concentration was ≧3.0 g/L. In cases in which the glucose concentration was below 3 g/L, the volume of the daily bolus feed was calculated to bring the glucose concentration back up to 3.0 g/L. The daily feed amount was recorded on batch sheets.

4. Sampling

Samples of cells were removed from the reactor on a daily basis. A sample used for cell counting was stained with trypan blue (Sigma, St. Louis, Mo.). Cell count and cell viability determination were performed via hemocytometry using a microscope, or via Cedex automatic cell counter (Innovatis AG, Bielefeld, Germany). For analysis of metabolites, additional sample was centrifuged for 20 minutes at 2000 rpm (4° C.) for cell separation. Supernatant was analyzed for the following parameters: titer, sialic acid, glucose, lactate, glutamine, glutamate, pH, $pO_2$, $pCO_2$, ammonia, and, optionally, lactate dehydrogenase (LDH). Additional back-up samples were frozen at −20° C.

Example 5B

This Example 5B describes the production of L104EA29YIg, shown as −1 to 357 or +1 to 357 in FIG. 4, (encoding DNA deposited with the ATCC as PTA-2104), from cultured CHO cells.

This Example 5B also describes a process of this invention involving addition of polyanionic compound, more specifically dextran sulfate, to a cell culture.

CHO cells used for L104EA29YIg expression were expanded in modified CD-CHO medium (Invitrogen, CA) containing glutamine, sodium bicarbonate, insulin, and methotrexate using T-75 flasks and shake-flasks. T-flasks and shake-flasks were incubated at 37° C. and 6% $CO_2$. After sufficient inoculum was generated, the culture was transferred into 5 or 10 L bioreactors using modified CD-CHO medium as described above, except without methotrexate. Initial seeding density was 200,000 viable cells/mL or $10^6$ cells/mL.

The 5 L and 10 L vessels were glass reactors equipped with one and two marine impellers respectively (Applikon, CA). Gas flows were controlled via rotameters. Air was sparged into the reactor via a submerged frit (5 μm pore size) and through the reactor head space for $CO_2$ removal. Molecular oxygen was sparged through the same frit for DO control. $CO_2$ was sparged through same frit for high side pH control. Low side pH control was realized via addition of 1 N NaOH or $Na_2CO_3$.

The culture in the bioreactor was given a daily bolus feed using modified eRDF medium (Invitrogen, CA) with glucose, galactose, glutamine, insulin, and TC Yeastolate (Becton Dickinson) in the following manner: starting one day post inoculation, a minimum of 1% culture volume was added, or if the glucose level was below 3 g/L, a calculated volume to bring glucose back to 3 g/L.

In all examples except example 11, the temperature was controlled at 37° C. from day 0 to 6; at 34° C. from day 6 to 10; at 32° C. from day 10 on.

The fermentation process had a typical duration of 14-19 days. Samples were taken on a daily basis from the reactor. The sample used for the cell count was stained with trypan blue (Sigma, Mo.). Cell count and cell viability determinations were performed using a Cedex automatic cell counter (Innovatis AG, Bielefeld, Germany). Supernatant was analyzed for: LEA29Y titer, glucose, lactate, glutamine, glutamate, pH, $pO_2$, $pCO_2$, ammonia.

Dextran sulfate (sodium salt, from dextran of average molecular weight 5000 Da, Sigma, Mo.) was dissolved into water or into medium. The solution was sterile-filtered and was added to the reactor to a concentration of 50 mg/L. The volume of the addition constituted at most 2% of the working volume of the reactor at the time the addition took place.

Example 6

This Example describes and presents the results of a comparative study to assess the effect of addition of polyanionic compound, more specifically dextran sulfate, at a time after innoculation. 5 L and 10 L bioreactors were inoculated with $0.2 \times 10^6$ cells/mL of L104EA29Y-producing cells.

Experiments 6-a and 6-b were designed as follows:

Example 6-a: dextran sulfate was not added to the cultures ('control' cultures: 4 cultures in 5 L bioreactors, 4 cultures in 10 L bioreactors).

Example 6-b: dextran sulfate was added to a concentration of 50 mg/L to the cultures on day 6 ('DS day 6' cultures: 2 cultures in 5 L bioreactors, 1 culture in 10 L bioreactor).

The average viability, viable cell density, and total cell density profiles, and their standard deviations for Examples 6-a and 6-b are reported in FIG. 6.

In the control cultures, a plateau in viable cell density was observed between days 6 and 7, corresponding to the stationary phase. A decline in viable cell density and viability was observed after day 7 (on average) for the control cultures, corresponding to the death phase. When dextran sulfate was added to the cultures on day 6, the growth phase was extended until day 11. Viable cell density reached on average $5.2 \times 10^6$ cells/mL, versus $3.5 \times 10^6$ cells/mL for the control. Viability remained above 90% during this extended growth phase. After day 11, viable cell density and total cell density declined in a proportional fashion, indicating cell lysis, and, as a result, the viability index remained above 90% until day 15.

FIG. 7 is a logarithmic representation of the viable cell densities as a function of time for cultures with dextran sulfate addition and for control runs. The death rates (given by the slopes of the viable cell densities in FIG. 2) differed depending on the presence or not of dextran sulfate. In the presence of dextran sulfate, death rate was approximately constant between day 12 and day 19, at a value of $0.0012$ $h^{-1}$. In contrast, death rate in the average of the controls was, between days 8 and 12 where it was at a maximum, $0.0024$ $h^{-1}$. Thus, dextran sulfate added on day 6 slowed down cell death rate during the death phase by a factor of two.

Despite the beneficial effects of dextran sulfate described above, product L104EA29YIg titer was similar with or without dextran sulfate addition (Table 8). Table 8: impact of day 6 dextran sulfate addition on product L104EA29YIg titer on day 14.

| Condition | Number of runs | Average titer day 14 | Standard deviation of titer |
|---|---|---|---|
| Control process | 8 | 1.60 | 0.18 |
| Day 6 dextran sulfate | 3 | 1.57 | 0.13 |

The extent of L104EA29YIg sialylation for different runs is reported in Table 9. Given the relatively large run-to-run variability, L104EA29YIg sialylation can be considered not to be significantly affected by the addition of dextran sulfate on day 6.

TABLE 9 impact of day 6 dextran sulfate addition on product L104EA29YIg sialylation.

| Condition | Run # | NANA molar ratio |
|---|---|---|
| Control process | 1 | 6.8 (14) |
| Control process | 2 | 5.5 (14) |
| Control process | 3 | 5.7 (15) |
| Control process | 4 | 5.5 (15) |
| Control process | 5 | 5.5 (15) |
| Control process | 6 | 6.3 (16) |
| Day 6 dextran sulfate | 7 | 5.4 (14) |
| Day 6 dextran sulfate | 8 | 6.9 (14) |
| Day 6 dextran sulfate | 9 | 6.9 (16) |

Example 7

This example shows the effect of adding dextran sulfate to a cell culture that is in the death phase.

A 5 L bioreactor of L104EA29YIg —producing cells was inoculated at a density of $10^6$ cells/mL, and the death phase started on day 5. Dextran sulfate was added on day 6.

The viability, viable cell density, and total cell density profile is presented in FIG. 8. Addition of dextran sulfate on day 6 of such a culture could prevent the occurrence of a major decline in viable cell density up to day 17. Thus, when dextran sulfate is added during the death phase, cell death can be arrested for several days.

In this run, a titer of 1.9 g/L with a NANA molar ration of 6.6 was obtained on day 14.

Example 8

This example shows the effect of adding dextran sulfate to a cell culture that is in the death phase.

A 10 L bioreactor was inoculated with $0.2 \times 10^6$ cells/mL of L104EA29YIg-producing cells. In this particular example, the daily feed was of a more concentrated formulation, and as a result the onset of the death phase was delayed until day 10 (FIG. 9). Dextran sulfate was not added until day 14.

The viability, viable cell density, and total cell density profile is presented in FIG. 9. Addition of dextran sulfate on day 14 allowed a stabilization of the viable cell density for a period of 4 days, after which the culture was discontinued.

This example is another illustration of the arrest of cell death during the death phase upon dextran sulfate addition to the culture.

Example 9

This example shows the effect of adding dextran sulfate on day 0. The effect of delayed addition of dextran sulfate may be seen by comparing the effect seen in this experiment with the effects seen in other experiments in which addition of dextran sulfate was delayed.

Two repeat 5 L bioreactors were inoculated with $0.2 \times 10^6$ cells/mL of L104EA29YIg-producing cells, and dextran sulfate was added to a concentration of 50 mg/L on the same day as the inoculation (day 0).

The viability, viable cell density, and total cell density profiles are presented in FIG. 10. Neither culture achieved a higher cell density than cultures devoid of dextran sulfate (Compare FIGS. 6 and 10). The cells entered the death phase on day 7 or 8, as opposed to day 11 when dextran sulfate is added on day 6 (Compare FIGS. 6 and 10). The L104EA29YIg titers obtained on day 14 of these runs were 0.57 g/L (run #1) and 0.86 g/L (run #2), which are significantly less than the titers obtained in the control process or in the process with day 6 dextran sulfate addition (see Example 6).

These results demonstrate the importance of the timing of dextran sulfate addition on the outcome of the addition.

Without being bound by theory, we propose that the observed effects of dextran sulfate addition and their dependance on the timing of the addition can be explained by the binding of dextran sulfate to diverse autocrine factors, in a manner similar to the binding of pentosan polysulfate to heparin-binding growth factors (Zugmaier et al., 1992). We propose that dextran sulfate binds to these factors at their heparin-binding domain, which becomes unavailable for binding to cell surface heparan sulfate proteoglycans. As a result, the dextran sufate-bound factors fail to concentrate at the cell surface, which greatly reduces the probability of their binding to their receptors. The net effect is that these factors do no longer exercise their normal action on the cells. In the very first few days after inoculation, the cells produce certain growth factors, whose function is to signal cell growth. Dextran sulfate added on day 0 irreversibly binds to those factors as they are produced. Binding of dextran sulfate to these factors does however not greatly affect cell growth in an adverse manner, possibly because the cells are able to respond by increasing growth factor production. Later during the growth phase, production of growth factors ceases, and the cells start producing autocrine factors of a different type, whose effect at a high concentration is to signal the end of the growth phase and the onset of cell death. These factors accumulate from a low concentration on day 0 to a high concentration at a later time. At that point, these factors effectively signal the cells to stop growing and to enter the stationary and the death phases. We propose that dextran sulfate preferentially binds to these death-signaling factors, thus disabling their signaling function and allowing an extension of the growth phase. Continuous induction by these factors appears to be needed for cell death to proceed, with the result that cells that have entered the death phase can be reset into a stationary phase when death-signalling factors are disabled by dextran sulfate (Examples 7 and 8), even as late as on day 14 in culture. Conversely, dextran sulfate added on day 0, that has bound to growth factors, is still bound to these factors at the end of the growth phase, making it unavailable for binding to death-signaling molecules. Thus, extension of the growth phase and delayed onset of cell death do not occur in the case of cultures where dextran sulfate is added on day 0 (Example 9) in the same way as they do in the case where dextran sulfate is added at the end of the growth phase.

The arrest of cell growth and the onset of cell death on day 11 in cultures supplemented with dextran sulfate on day 6 in Example 6 is hypothesized to result from mechanisms different from induction by dextran sulfate-binding autocrine factors. Possibly, the exhaustion of particular nutrients in the medium following 11 days of growth may be accountable for the end of the growth phase in these cultures.

Example 10

This Example compares the effect of addition of dextran sulfate at three different times during the initial growth phase.

Cultures of L104EA29YIg-producing cells were inoculated at $10^6$ cells/mL in 5-L bioreactors. Dextran sulfate was added to the cultures to a concentration of 50 mg/L at different times. In one culture, dextran sulfate was added on day 3, in another on day 4, and in a third on day 5.

The viability and viable cell density profiles are reported in FIG. 11. High viable cell densities ($>10^7$ cells/mL) were achieved in all three cases of additions (day 3, 4 or 5), but the earlier additions (day 3 or 4) did not prevent a decline in the viable cell density immediately following the growth phase. In contrast, day 5 addition stabilized the viable cell density for 4 days following the growth phase. At time points past 250 h, the viable cell density in the day 5 dextran sulfate addition culture was always higher or equal (within measuring error) than in the day 4 dextran sulfate addition culture, and the viable cell density in the day 4 dextran sulfate addition culture was always higher or equal (within measuring error) than in the day 3 dextran sulfate addition culture. Thus, it appears from this example that the optimal time for dextran sulfate addition is at the end of the initial growth phase (referring to the growth phase that would have been observed in the absence of any dextran sulfate addition). Earlier addition can extend the growth phase but will not be as effective at stabilizing the viable cell density following the dextran sulfate-induced extended growth phase, whereas later addition (during the death phase) will stabilize the viable cell density but may fail to provide a substantial increase in viable cell density (see Examples 7 and 8). Accordingly, on day 14 a titer of 2.7 g/L was obtained with day 5 dextran sulfate addition, whereas day 14 titers of 2.6 g/L were obtained with day 3 or day 4 dextran sulfate addition, and a day 14 titer of 1.9 g/L was obtained with day 6 dextran sulfate addition (in Example 7). The NANA molar ratios were 6.3, 6.6, 6.0, and 6.6 respectively in the runs mentioned above, showing that higher titers obtained with optimal timing of dextran sulfate addition came with a consistent level of sialylation.

Example 11

This example shows the effect of one and two temperature shifts in a culture producing L104EA29YIg. The culture is also subject to delayed addition of dextran sulfate.

5 L reactors were inoculated at a density of 200,000 cells/mL.

Two, one, or no T-shifts were applied. For one temperature shift, the temperature is shifted from 37° C. to 34° C. on day 6. For two temperature shifts, the temperature is shifted from 37° C. to 34° C. on day 6, and from 34° C. to 32° C. on day 10. In all cases dextran sulfate was added on day 6. The two T-shift case is the average of three runs, and standard deviations are shown with bars.

Viable cell density, viability, and titer are reported in FIGS. 12, 13, and 14 respectively.

The results show the benefits of applying at least one temperature shift. In the case where the temperature is maintained at 37° C. throughout the run, the culture enters the death phase on day 10, and the decrease in viable cell density and viability is steep. As a result, there is a clear decrease in L104EA29YIg volumetric productivity after 12 days in culture. For culture times of 14 days and longer, it is clear that cultures that have one or two temperature shifts will outperform the constant temperature culture in terms of titer.

In the case where only one temperature shift is implemented (on day 6, to 34° C.), a steep decrease in viable cell density and viability is observed after day 16. The culture where a second temperature shift (on day 10, to 32° C.) is implemented in addition to the first does not show as steep a decline in viable cell density and viability after day 16. At culture times past 18 days, volumetric productivity in the one T-shift culture is clearly inferior to that in the two T-shifts culture. In contrast, volumetric productivity in the culture with one T-shift is superior to that in the two T-shifts culture at culture times between day 11 and day 15.

In conclusion, the first temperature shift is beneficial independently of the desired harvest time, whereas the benefit of the second temperature shift depends on the intended harvest time and the viability requirements for effective downstream processing. The absence of a second temperature shift will allow to reach at higher product titer until day 20, but for cultures that are run for longer than 20 days, the run with two temperature shifts will outperform the run with one temperature shift in terms of titer. In addition, it must be considered harvests past day 12 will contain higher amount of cell lysis products in the case of one T-shift than in the case of two T-shifts, which can complicate downstream processing. The steep decrease in viable cell density observed after day 12 in the case of the one T-shift profile can be a concern for product quality, as the corresponding cell death may release into the supernatant a significant load of sialidases that can decrease product sialylation.

The contents of all issued and granted patents, patent applications, published PCT and U.S. applications, articles, books, references, reference and instruction manuals, and abstracts as referenced or cited herein are hereby incorporated by reference in their entireties to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

What is claimed is:

1. A cell culturing process comprising:
   a) culturing host cells which produce soluble cytotoxic T-lymphocyte antigen-4 (CTLA4) molecules at a first temperature of 37° C. under cell culture conditions and for a time period that allows for cell growth;
   b) then culturing the cells at a second temperature of 34° C;
   c) then culturing the cells at a third temperature of 32° C. and
   d) then culturing the cells at a fourth temperature of 30° C. and
   wherein the cells are cultured at the second temperature starting about day 5 to day 7 of the culture, and wherein there are approximately four days between the start of the second temperature and the start of the third temperature and wherein the fourth temperature starts on or about two weeks from the start of the culture until the end of the culturing process.

2. The process according to claim 1, wherein the cells are cultured at the second temperature starting about day 6 of the culture, and wherein the cells are cultured at the third temperature starting about day 10 of the culture.

3. The process according to claim 1, wherein the soluble CTLA4 molecule is a CTLA4 fusion protein.

4. The process according to claim 3, wherein the soluble CTLA4 fusion protein is a cytotoxic T-lymphocyte antigen-4 immunoglobulin (CTLA4Ig) molecule.

5. The process according to claim 4, wherein the soluble CTLA4 fusion protein is CTLA4Ig comprising amino acids −1 to 357 or +1 to 357 as shown in SEQ ID NO:2.

6. The process according to claim 1, wherein the soluble CTLA4 molecule is a soluble CTLA4 mutant molecule.

7. The process according to claim 6, wherein the soluble CTLA4 mutant molecule is L104EA29YIg comprising amino acids −1 to 357 or +1 to 357 as shown in SEQ ID NO: 4.

8. The process according to claim 1, wherein the cell culturing process is a fed-batch process or a continuous process.

9. The process according to claim 1, wherein the cells are cultured at 34° C. from day 6 to day 10 and are cultured at 32° C. for 10-14 days.

10. The process according to claim 9, wherein the protein is soluble CTLA4 fusion protein is CTLA4Ig comprising amino acids −1 to 357 or +1 to 357 as shown in SEQ ID NO:2, or soluble CTLA4 mutant molecule L104EA29YIg comprising amino acids −1 to 357 or +1 to 357 as shown in SEQ ID NO: 4.

11. The process according to claim 1, wherein the temperature of the culture is shifted from 37° C. to 34° C. when the cell density in the culture is about $2\text{-}12\times10^6$ cells/mL.

12. The process according to claim 1, wherein the temperature of the culture is shifted from 37° C. to 34° C. when the culture is in the stationary phase.

13. The process according to claim 1, wherein the produced protein comprises enhanced sialylation during cell culturing.

14. The process according to claim 1, wherein the cells are mammalian cells.

15. The process according to claim 14, wherein the mammalian cells are CHO cells.

16. The process according to claim 1, wherein protein production is increased.

17. The process according to claim 1, wherein cell viability is increased.

18. A cell culturing process comprising:
   a) culturing CHO cells which produce a soluble CTLA4 molecule at 37° C. under conditions and for a time period that allow for cell growth;
   b) then culturing the cells at 34° C. starting on day 6 of the culture;
   c) then culturing the cells at 32° C. starting on day 10 of the culture; and
   d) culturing the cells at 30° C. starting on day 14 of the culture.

\* \* \* \* \*

UNITED STATES PATENT AND TRADEMARK OFFICE
CERTIFICATE OF CORRECTION

PATENT NO. : 7,541,164 B2
APPLICATION NO. : 10/742564
DATED : June 2, 2009
INVENTOR(S) : Bernhard M. Schilling et al.

It is certified that error appears in the above-identified patent and that said Letters Patent is hereby corrected as shown below:

On the title page, item: [56]
Column 1 (Inventors)
Line 7 delete "East Syracuse, NY" and insert -- DeWitt, NY --
Line 8 delete "Syracuse, NY" and insert -- Manlius, NY --

Column 2 (Other Publications)
Delete "Kaufmann et al. (1999) Influence of low temperature on productivity, proteome and protein phosphorylation of CHO cells. Biotechnol Bioeng. Vol. 63, No. 5, pp. 573-582"

Column 6
Line 50 "innoculation" should read -- inoculation --
Line 51 "innoculation" should read -- inoculation --

Column 8
Line 39 "viaability" should read -- viability --

Column 15
Line 30 "innoculation" should read -- inoculation --
Line 39 "innoculation" should read -- inoculation --
Line 52 "innoculation" should read -- inoculation --

Column 16
Line 13 "innoculation" should read -- inoculation --
Line 14 "innoculation" should read -- inoculation --
Line 16 "innoculation" should read -- inoculation --
Line 20 "innoculation" should read -- inoculation --
Line 59 "innoculation" should read -- inoculation --
Line 61 "innoculation" should read -- inoculation --

Column 17
Line 10 "innoculation" should read -- inoculation --
Line 12 "innoculation" should read -- inoculation --
Line 19 "innoculation" should read -- inoculation --
Line 33 "innoculation" should read -- inoculation --
Line 40 "innoculation" should read -- inoculation --

UNITED STATES PATENT AND TRADEMARK OFFICE
CERTIFICATE OF CORRECTION

PATENT NO. : 7,541,164 B2
APPLICATION NO. : 10/742564
DATED : June 2, 2009
INVENTOR(S) : Bernhard M. Schilling et al.

It is certified that error appears in the above-identified patent and that said Letters Patent is hereby corrected as shown below:

Column 18
Line 2 "innoculation" should read -- inoculation --
Line 13 "innoculation" should read -- inoculation --
Line 20 "innoculation" should read -- inoculation --
Line 43 "innoculation" should read -- inoculation --

Column 19
Line 34 "innoculation" should read -- inoculation --

Column 27
Line 55 "innoculation" should read -- inoculation --

Column 29
Line 2 "innoculation" should read -- inoculation --

Column 46
Line 62 "innoculation" should read -- inoculation --

Column 48
Lines 59-60 "dependance" should read -- dependence --

Signed and Sealed this

Twenty-seventh Day of October, 2009

David J. Kappos
*Director of the United States Patent and Trademark Office*